US012692294B2

(12) United States Patent
Bates et al.

(10) Patent No.: US 12,692,294 B2
(45) Date of Patent: Jul. 28, 2026

(54) ENGINEERED NRG-1 VARIANTS WITH IMPROVED SELECTIVITY TOWARD ErbB4 BUT NOT AGAINST ErbB3

(71) Applicant: Amgen Inc., Thousand Oaks, CA (US)

(72) Inventors: Darren L. Bates, Oak Park, CA (US); Zhi Liu, Shoreline, WA (US); TaeWeon Lee, Palo Alto, CA (US); Mark L. Michaels, Encino, CA (US); Zhulun Wang, Palo Alto, CA (US)

(73) Assignee: Amgen Inc., Thousand Oaks, CA (US)

( * ) Notice: Subject to any disclaimer, the term of this patent is extended or adjusted under 35 U.S.C. 154(b) by 356 days.

(21) Appl. No.: 17/836,425

(22) Filed: Jun. 9, 2022

(65) Prior Publication Data

US 2022/0402985 A1     Dec. 22, 2022

Related U.S. Application Data

(60) Provisional application No. 63/209,248, filed on Jun. 10, 2021.

(51) Int. Cl.
*C07K 14/485* (2006.01)
*A61P 9/10* (2006.01)
*A61K 38/00* (2006.01)

(52) U.S. Cl.
CPC .............. *C07K 14/485* (2013.01); *A61P 9/10* (2018.01); *A61K 38/00* (2013.01)

(58) Field of Classification Search
CPC .. C07K 14/485; C07K 14/4756; A61K 38/00; A61P 9/10
See application file for complete search history.

(56) References Cited

U.S. PATENT DOCUMENTS

| | | | |
|---|---|---|---|
| 1,104,741 A * | 7/1914 | Li et al. .................... | B65H 3/24 271/131 |
| 5,367,060 A | 11/1994 | Vandlen et al. | |
| 5,530,109 A | 6/1996 | Goodearl et al. | |
| 5,607,342 A * | 3/1997 | Evdokimenko ......... | B05B 7/205 451/75 |
| 5,670,342 A | 9/1997 | Carnahan | |
| 5,686,415 A | 11/1997 | Carnahan | |
| 5,716,930 A | 2/1998 | Goodearl et al. | |
| 5,770,567 A | 6/1998 | Ho | |
| 5,849,705 A | 12/1998 | Carnahan | |
| 5,929,032 A | 7/1999 | Carnahan | |
| 6,136,558 A * | 10/2000 | Ballinger ......... | C07K 14/57509 514/8.4 |
| 6,387,638 B1 | 5/2002 | Ballinger et al. | |
| 6,635,249 B1 | 10/2003 | Marchionni | |
| 7,063,961 B2 | 6/2006 | Ballinger et al. | |
| 7,115,554 B1 | 10/2006 | Sklar et al. | |
| 7,226,907 B1 | 6/2007 | Zhou | |
| 7,557,181 B2 | 7/2009 | Pienkos | |
| 7,612,164 B2 | 11/2009 | Zhou | |
| 7,795,212 B2 | 9/2010 | Zhou | |
| 7,964,555 B2 | 6/2011 | Zhou | |
| 8,394,761 B2 | 3/2013 | Marchionni | |
| 8,476,405 B2 | 7/2013 | Zhou | |
| 8,609,620 B2 * | 12/2013 | Zhou ......................... | A61P 9/10 514/21.3 |
| 8,785,387 B2 | 7/2014 | Zhou | |
| 9,012,400 B2 | 4/2015 | Zhou | |
| 9,089,524 B2 | 7/2015 | Zhou | |
| 9,198,951 B2 | 12/2015 | Caggiano | |
| 9,340,597 B2 | 5/2016 | Zhou | |
| 9,434,777 B2 | 9/2016 | Zhou | |
| 9,555,076 B2 | 1/2017 | Zhou | |
| 9,655,949 B2 | 5/2017 | Zhou | |
| 9,956,266 B2 | 5/2018 | Caggiano | |
| 10,098,834 B2 | 10/2018 | Zhou | |
| 10,112,983 B2 * | 10/2018 | Zhou ......................... | A61P 9/10 |
| 10,232,016 B2 | 3/2019 | Marchionni | |
| 10,441,633 B2 | 10/2019 | Zhou | |
| 10,561,709 B2 | 2/2020 | Zhou | |
| 2007/0213264 A1 | 9/2007 | Zhou | |
| 2011/0229444 A1 | 9/2011 | Zhou | |
| 2015/0284440 A1 | 10/2015 | Zhou | |
| 2018/0303904 A1 | 10/2018 | Caggiano | |

FOREIGN PATENT DOCUMENTS

| | | |
|---|---|---|
| EP | 1981525 B1 | 10/2008 |
| EP | 1890721 B1 | 9/2010 |
| EP | 2528616 B1 | 12/2012 |
| EP | 3135685 B1 | 7/2020 |
| WO | 9709425 A1 | 3/1997 |
| WO | 0064400 A2 | 11/2000 |
| WO | 0149845 A1 | 7/2001 |
| WO | 2006030241 A2 | 3/2006 |
| WO | 2007/062594 A1 | 6/2007 |

(Continued)

OTHER PUBLICATIONS

Carraway et al., "Neuregulin-2, a new ligand of ErbB3/ErbB4-receptor tyrosine kinases", Nature, vol. 387, pp. 512-516 (1997).
Chang et al., Ligands for ErbB-family receptors encoded by a neuregulin-like gene, Nature, 387:509-512 (1997).
De Keulenaer et al., "Mechanisms of the Multitasking Endothelial Protein NRG-1 as a Compensatory Factor During Chronic Heart Failure", Circulation: Heart Failure, vol. 12, Issue 10, 2019.
Higashiyama et al., "A Novel Brain-Derived Member of the Epidermal Growth Factor Family That Interacts with ErbB3 and ErbB4" J. Bio Chem., 122:675-680 (1997).
Hijazi et al., "NRG-3 in human breast cancers: Activation of multiple erbB family proteins", Int. J. Oncol., 13:1061-1067 (1998).
Holmes et al., "Identification of Heregulin, a Specific Activator of p 1 a5erbB2", Science, 256:1205-1210 (1992).

(Continued)

*Primary Examiner* — Sudhakar Katakam
(74) *Attorney, Agent, or Firm* — Randolph N. Mohr

(57) ABSTRACT

The present invention relates to engineered neuregulin-1 variants that selectively activate ErbB4 receptors but do not activate ErbB3 receptors. The invention also provides methods for using such variants to treat heart failure.

4 Claims, 2 Drawing Sheets

Specification includes a Sequence Listing.

(56) References Cited

FOREIGN PATENT DOCUMENTS

| | | |
|---|---|---|
| WO | 2009007332 A2 | 1/2009 |
| WO | 2009033373 A1 | 3/2009 |
| WO | 2010060265 A1 | 6/2010 |
| WO | 20035012 A1 | 2/2020 |
| WO | 2020143548 A1 | 7/2020 |

OTHER PUBLICATIONS

Jay et al., "An Engineered Bivalent Neuregulin Protects Against Doxorubicin-Induced Cardiotoxicity With Reduced Proneoplastic Potential", Circulation, vol. 128, pp. 152-161 (2013).

Jones et al., "Binding specificities and affinities of egf domains for ErbB receptors", FEBS Letters, vol. 447, pp. 227-231 (1999).

Liu et al., "Neuregulin-1/erbB-Activation Improves Cardiac Function and Survival in Models of Ischemic, Dilated, and Viral Cardiomyopathy", J Amer Coll Cardiol, 48:1438-1447 (2006).

Peles et al., "Isolation of the Neu/HER-2 Stimulatory Ligand: A 44 kd Glycoprotein That Induces Differentiation of Mammary Tumor Cells", Cell 69:205-216 (1992).

Wali et al., "Convergent and Divergent Cellular Responses by ErbB4 Isoforms in Mammary Epithelial Cells", Mol Cancer Res, 12:1140-1155 (2014).

Luo C et al: "Computational Analysis of Molecular Basis of 1 :1 Interactions of NRG-1 beta Wild-Type and Variants With ErbB3 and ErbB4", Proteins: Structure, Function, and Bioinformatics, John Wiley & Sons, Inc, US, vol. 59, No. 4, Apr. 8, 2005 (Apr. 8, 2005), pp. 742-756.

Jones J T et al: "Binding Interaction of the Heregulinbeta egf Domain with ErbB3 and ErbB4 Receptors Assessed by Alanine Scanning Mutagenesis", 19980508, vol. 273, No. 19, May 8, 1998 (May 8, 1998), pp. 11667-11674.

* cited by examiner

```
                          SEQUENCE LISTING

<160> NUMBER OF SEQ ID NOS: 231

<210> SEQ ID NO 1
<211> LENGTH: 295
<212> TYPE: PRT
<213> ORGANISM: Artificial Sequence
<220> FEATURE:
<223> OTHER INFORMATION: huNRG1(S177-F229)(NRGE1C)::3x(G4Q)::huFcSEFL2
      (Pb)

<400> SEQUENCE: 1

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gln Gly Gly Gly Gln Gly
    50                  55                  60

Gly Gly Gly Gln Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Cys Glu Glu Gln Tyr
    130                 135                 140

Gly Ser Thr Tyr Arg Cys Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295

<210> SEQ ID NO 2
```

```
<211> LENGTH: 303
<212> TYPE: PRT
<213> ORGANISM: Artificial Sequence
<220> FEATURE:
<223> OTHER INFORMATION: huNRG1(S177-F229)
      (NRGE1C)::1KmodT482V,M493L)::huFcSEFL2 (Pb)

<400> SEQUENCE: 2

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Ser Gly Ser Ala Thr Gly Gly Ser Gly Ser
    50                  55                  60

Val Ala Ser Ser Gly Ser Gly Ser Ala Thr His Leu Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
            115                 120                 125

Val Lys Phe Asn Trp Tyr Val Asp Gly Val Glu Val His Asn Ala Lys
        130                 135                 140

Thr Lys Pro Cys Glu Glu Gln Tyr Gly Ser Thr Tyr Arg Cys Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
            195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 3
<211> LENGTH: 294
<212> TYPE: PRT
<213> ORGANISM: Artificial Sequence
<220> FEATURE:
<223> OTHER INFORMATION: huNRG1(S177-F229)(NRGE1C)::(G4A)2:G4::huFcSEFL2
      (Pb)

<400> SEQUENCE: 3

Ser His Leu Val Lys Cys Gly Glu Lys His Lys Ser Phe Cys Val Asn
1               5                   10                  15
```

```
Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gly Ala Gly Gly Gly Gly Ala Gly
        50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
    290

<210> SEQ ID NO 4
<211> LENGTH: 294
<212> TYPE: PRT
<213> ORGANISM: Artificial Sequence
<220> FEATURE:
<223> OTHER INFORMATION: huNRG1(S177-F229)(NRGE1C)
      ((G4E)2)::G4::huFcSEFL2 (Pb)

<400> SEQUENCE: 4

Ser His Leu Val Lys Cys Gly Glu Lys His Lys Ser Phe Cys Val Asn
1                   5                   10                  15

Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gly Glu Gly Gly Gly Gly Glu Gly
        50                  55                  60

Gly Gly Gly Asp Lys Thr His Thr Cys Pro Pro Cys Pro Ala Pro Glu
```

-continued

```
65                      70                      75                      80
Leu Leu Gly Gly Pro Ser Val Phe Leu Phe Pro Pro Lys Pro Lys Asp
                85                      90                      95

Thr Leu Met Ile Ser Arg Thr Pro Glu Val Thr Cys Val Val Val Asp
            100                     105                     110

Val Ser His Glu Asp Pro Glu Val Lys Phe Asn Trp Tyr Val Asp Gly
        115                     120                     125

Val Glu Val His Asn Ala Lys Thr Lys Pro Cys Glu Glu Gln Tyr Gly
    130                     135                     140

Ser Thr Tyr Arg Cys Val Ser Val Leu Thr Val Leu His Gln Asp Trp
145                     150                     155                     160

Leu Asn Gly Lys Glu Tyr Lys Cys Lys Val Ser Asn Lys Ala Leu Pro
                165                     170                     175

Ala Pro Ile Glu Lys Thr Ile Ser Lys Ala Lys Gly Gln Pro Arg Glu
            180                     185                     190

Pro Gln Val Tyr Thr Leu Pro Pro Ser Arg Glu Glu Met Thr Lys Asn
        195                     200                     205

Gln Val Ser Leu Thr Cys Leu Val Lys Gly Phe Tyr Pro Ser Asp Ile
    210                     215                     220

Ala Val Glu Trp Glu Ser Asn Gly Gln Pro Glu Asn Asn Tyr Lys Thr
225                     230                     235                     240

Thr Pro Pro Val Leu Asp Ser Asp Gly Ser Phe Phe Leu Tyr Ser Lys
                245                     250                     255

Leu Thr Val Asp Lys Ser Arg Trp Gln Gln Gly Asn Val Phe Ser Cys
            260                     265                     270

Ser Val Met His Glu Ala Leu His Asn His Tyr Thr Gln Lys Ser Leu
        275                     280                     285

Ser Leu Ser Pro Gly Lys
    290

<210> SEQ ID NO 5
<211> LENGTH: 294
<212> TYPE: PRT
<213> ORGANISM: Artificial Sequence
<220> FEATURE:
<223> OTHER INFORMATION: huNRG1(S177-F229)
      (NRGE1C)::(G4S)2::G4::huFcSEFL2 (Pb)

<400> SEQUENCE: 5

Ser His Leu Val Lys Cys Gly Glu Lys His Lys Ser Phe Cys Val Asn
1                   5                       10                      15

Gly Gly Glu Cys Phe Met Ile Glu Gly Pro Ser Asn Pro Ser Arg Tyr
                20                      25                      30

Leu Cys Lys Cys Pro Asn Glu Phe Thr Gly Asp Arg Cys Gln Glu Asp
            35                      40                      45

Phe Met Ala Ser Phe Gly Gly Gly Ser Gly Gly Gly Ser Gly
    50                      55                      60

Gly Gly Gly Asp Lys Thr His Thr Cys Pro Pro Cys Pro Ala Pro Glu
65                      70                      75                      80

Leu Leu Gly Gly Pro Ser Val Phe Leu Phe Pro Pro Lys Pro Lys Asp
                85                      90                      95

Thr Leu Met Ile Ser Arg Thr Pro Glu Val Thr Cys Val Val Val Asp
            100                     105                     110

Val Ser His Glu Asp Pro Glu Val Lys Phe Asn Trp Tyr Val Asp Gly
        115                     120                     125
```

```
Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
    275                 280                 285

Ser Leu Ser Pro Gly Lys
    290
```

<210> SEQ ID NO 6
<211> LENGTH: 294
<212> TYPE: PRT
<213> ORGANISM: Artificial Sequence
<220> FEATURE:
<223> OTHER INFORMATION: huNRG1(S177-F229)(NRGE1C)
     (G4E)::G4S::G4::huFcSEFL2 (Pb)

<400> SEQUENCE: 6

```
Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gly Glu Gly Gly Gly Gly Ser Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
            115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190
```

-continued

```
Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
            245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
        290

<210> SEQ ID NO 7
<211> LENGTH: 292
<212> TYPE: PRT
<213> ORGANISM: Artificial Sequence
<220> FEATURE:
<223> OTHER INFORMATION: huNRG1(S177-F229)(NRGE1C)
      (NRGmod)::G4::huFcSEFL2 (Pb)

<400> SEQUENCE: 7

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Ala Ala Ala Glu Glu Leu Tyr Gln Gly Gly Gly
    50                  55                  60

Gly Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
            85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Cys Glu Glu Gln Tyr Gly Ser Thr
        130                 135                 140

Tyr Arg Cys Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
        210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
```

-continued

```
                  245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 8
<211> LENGTH: 295
<212> TYPE: PRT
<213> ORGANISM: Artificial Sequence
<220> FEATURE:
<223> OTHER INFORMATION: huNRG1(S177-F229)
      (NRGE1D)::1KmodT482V,M493L)::huFcSEFL2 (Pb)

<400> SEQUENCE: 8

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gln Gly Gly Gly Gly Gln Gly
    50                  55                  60

Gly Gly Gly Gln Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Cys Glu Glu Gln Tyr
    130                 135                 140

Gly Ser Thr Tyr Arg Cys Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295
```

<210> SEQ ID NO 9
<211> LENGTH: 303
<212> TYPE: PRT
<213> ORGANISM: Artificial Sequence
<220> FEATURE:
<223> OTHER INFORMATION: huNRG1(S177-F229)
      (NRGE1D)::1KmodT482V,M493L)::huFcSEFL2 (Pb)

<400> SEQUENCE: 9

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Ser Gly Ser Ala Thr Gly Gly Ser Gly Ser
    50                  55                  60

Val Ala Ser Ser Gly Ser Gly Ser Ala Thr His Leu Asp Lys Thr His
65                  70                  75                  80

Thr Cys Pro Pro Cys Pro Ala Pro Glu Leu Leu Gly Gly Pro Ser Val
            85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Cys Glu Glu Gln Tyr Gly Ser Thr Tyr Arg Cys Val Ser
145                 150                 155                 160

Val Leu Thr Val Leu His Gln Asp Trp Leu Asn Gly Lys Glu Tyr Lys
            165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
            245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 10
<211> LENGTH: 294
<212> TYPE: PRT
<213> ORGANISM: Artificial Sequence
<220> FEATURE:
<223> OTHER INFORMATION: huNRG1(S177-F229)(NRGE1D)::(G4A)2:G4::huFcSEFL2
      (Pb)

<400> SEQUENCE: 10

```
Ser His Leu Val Lys Cys Gly Glu Ser His Lys Ser Phe Cys Val Asn
1               5               10              15

Gly Gly Glu Cys Tyr Met Val Glu Gly Ser Ser Ile Pro Ser Arg Tyr
            20              25              30

Leu Cys Lys Cys Pro Asn Glu Phe Thr Gly Asp Arg Cys Gln Glu Asp
        35              40              45

Phe Met Ala Ser Phe Gly Gly Gly Gly Ala Gly Gly Gly Gly Ala Gly
    50              55              60

Gly Gly Gly Asp Lys Thr His Thr Cys Pro Pro Cys Pro Ala Pro Glu
65              70              75              80

Leu Leu Gly Gly Pro Ser Val Phe Leu Phe Pro Pro Lys Pro Lys Asp
                85              90              95

Thr Leu Met Ile Ser Arg Thr Pro Glu Val Thr Cys Val Val Val Asp
            100             105             110

Val Ser His Glu Asp Pro Glu Val Lys Phe Asn Trp Tyr Val Asp Gly
        115             120             125

Val Glu Val His Asn Ala Lys Thr Lys Pro Cys Glu Glu Gln Tyr Gly
    130             135             140

Ser Thr Tyr Arg Cys Val Ser Val Leu Thr Val Leu His Gln Asp Trp
145             150             155             160

Leu Asn Gly Lys Glu Tyr Lys Cys Lys Val Ser Asn Lys Ala Leu Pro
                165             170             175

Ala Pro Ile Glu Lys Thr Ile Ser Lys Ala Lys Gly Gln Pro Arg Glu
            180             185             190

Pro Gln Val Tyr Thr Leu Pro Pro Ser Arg Glu Glu Met Thr Lys Asn
            195             200             205

Gln Val Ser Leu Thr Cys Leu Val Lys Gly Phe Tyr Pro Ser Asp Ile
    210             215             220

Ala Val Glu Trp Glu Ser Asn Gly Gln Pro Glu Asn Asn Tyr Lys Thr
225             230             235             240

Thr Pro Pro Val Leu Asp Ser Asp Gly Ser Phe Phe Leu Tyr Ser Lys
                245             250             255

Leu Thr Val Asp Lys Ser Arg Trp Gln Gln Gly Asn Val Phe Ser Cys
            260             265             270

Ser Val Met His Glu Ala Leu His Asn His Tyr Thr Gln Lys Ser Leu
        275             280             285

Ser Leu Ser Pro Gly Lys
    290
```

```
<210> SEQ ID NO 11
<211> LENGTH: 294
<212> TYPE: PRT
<213> ORGANISM: Artificial Sequence
<220> FEATURE:
<223> OTHER INFORMATION: huNRG1(S177-F229)
      (NRGE1D)::(G4S)2::G4::huFcSEFL2 (Pb)

<400> SEQUENCE: 11
```

```
Ser His Leu Val Lys Cys Gly Glu Ser His Lys Ser Phe Cys Val Asn
1               5               10              15

Gly Gly Glu Cys Tyr Met Val Glu Gly Ser Ser Ile Pro Ser Arg Tyr
            20              25              30

Leu Cys Lys Cys Pro Asn Glu Phe Thr Gly Asp Arg Cys Gln Glu Asp
        35              40              45

Phe Met Ala Ser Phe Gly Gly Gly Gly Glu Gly Gly Gly Gly Glu Gly
    50              55              60
```

```
Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                    85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
            115                 120                 125

Val Glu Val His Asn Ala Lys Thr Lys Pro Cys Glu Glu Gln Tyr Gly
        130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
        210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
        290
```

```
<210> SEQ ID NO 12
<211> LENGTH: 294
<212> TYPE: PRT
<213> ORGANISM: Artificial Sequence
<220> FEATURE:
<223> OTHER INFORMATION: huNRG1(S177-F229)(NRGE1D)
      (G4E)::G4S::G4::huFcSEFL2 (Pb)

<400> SEQUENCE: 12
```

```
Ser His Leu Val Lys Cys Gly Glu Ser His Lys Ser Phe Cys Val Asn
1                   5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
            35                  40                  45

Phe Met Ala Ser Phe Gly Gly Gly Ser Gly Gly Gly Gly Ser Gly
        50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                    85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
```

-continued

```
              115                 120                 125
Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
                195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
                275                 280                 285

Ser Leu Ser Pro Gly Lys
    290

<210> SEQ ID NO 13
<211> LENGTH: 294
<212> TYPE: PRT
<213> ORGANISM: Artificial Sequence
<220> FEATURE:
<223> OTHER INFORMATION: huNRG1(S177-F229)(NRGE1D)
      (NRGmod)::G4::huFcSEFL2 (Pb)

<400> SEQUENCE: 13

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
            35                  40                  45

Phe Met Ala Ser Phe Gly Gly Gly Glu Gly Gly Gly Gly Ser Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
    115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175
```

-continued

```
Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
            210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
            245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
            275                 280                 285

Ser Leu Ser Pro Gly Lys
            290
```

```
<210> SEQ ID NO 14
<211> LENGTH: 292
<212> TYPE: PRT
<213> ORGANISM: Artificial Sequence
<220> FEATURE:
<223> OTHER INFORMATION: huNRG1(S177-F229)(NRGE1D)
      (NRGmod)::G4::huFcSEFL2 (Pb)

<400> SEQUENCE: 14
```

```
Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
            35                  40                  45

Phe Met Ala Ser Phe Ala Ala Ala Glu Glu Leu Tyr Gln Gly Gly Gly
            50                  55                  60

Gly Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
            85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
            115                 120                 125

Val His Asn Ala Lys Thr Lys Pro Cys Glu Glu Gln Tyr Gly Ser Thr
            130                 135                 140

Tyr Arg Cys Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
            165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
            195                 200                 205

Ser Leu Thr Cys Leu Val Lys Gly Phe Tyr Pro Ser Asp Ile Ala Val
            210                 215                 220

Glu Trp Glu Ser Asn Gly Gln Pro Glu Asn Asn Tyr Lys Thr Thr Pro
225                 230                 235                 240
```

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 15
<211> LENGTH: 303
<212> TYPE: PRT
<213> ORGANISM: Artificial Sequence
<220> FEATURE:
<223> OTHER INFORMATION: huNRG1(S177-Q237)(3H8)::3xG4S::huFcSEFL2 (Pb)

<400> SEQUENCE: 15

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Gly
    50                  55                  60

Gly Ser Gly Gly Gly Gly Ser Gly Gly Gly Ser Asp Lys Thr His
65                  70                  75                  80

Thr Cys Pro Pro Cys Pro Ala Pro Glu Leu Leu Gly Gly Pro Ser Val
            85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
    130                 135                 140

Thr Lys Pro Cys Glu Glu Gln Tyr Gly Ser Thr Tyr Arg Cys Val Ser
145                 150                 155                 160

Val Leu Thr Val Leu His Gln Asp Trp Leu Asn Gly Lys Glu Tyr Lys
            165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
            245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

-continued

```
<210> SEQ ID NO 16
<211> LENGTH: 295
<212> TYPE: PRT
<213> ORGANISM: Artificial Sequence
<220> FEATURE:
<223> OTHER INFORMATION: huNRG1(S177-Q237)(3H8)::3x(G4Q)::huFcSEFL2 (Pb)

<400> SEQUENCE: 16

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gln Gly Gly Gly Gln Gly
        50                  55                  60

Gly Gly Gly Gln Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Cys Glu Glu Gln Tyr
    130                 135                 140

Gly Ser Thr Tyr Arg Cys Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
            195                 200                 205

Asn Gln Val Ser Leu Thr Cys Leu Val Lys Gly Phe Tyr Pro Ser Asp
        210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
            245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295

<210> SEQ ID NO 17
<211> LENGTH: 303
<212> TYPE: PRT
<213> ORGANISM: Artificial Sequence
<220> FEATURE:
<223> OTHER INFORMATION: huNRG1(S177-Q237)(3H8)::3x(G4Q)::huFcSEFL2 (Pb)

<400> SEQUENCE: 17

Ser His Leu Val Lys Cys Gly Glu Lys His Lys Ser Phe Cys Val Asn
```

-continued

```
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
                35                  40                  45

Phe Met Ala Ser Phe Tyr Lys Ala Glu Glu Leu Tyr Gln Gly Gly Gly
                50                  55                  60

Gly Gln Gly Gly Gly Gly Gln Gly Gly Gly Gln Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
                100                 105                 110

Pro Glu Val Thr Cys Val Val Val Asp Val Ser His Glu Asp Pro Glu
                115                 120                 125

Val Lys Phe Asn Trp Tyr Val Asp Gly Val Glu Val His Asn Ala Lys
                130                 135                 140

Thr Lys Pro Cys Glu Glu Gln Tyr Gly Ser Thr Tyr Arg Cys Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Ala Leu Pro Ala Pro Ile Glu Lys Thr Ile
                180                 185                 190

Ser Lys Ala Lys Gly Gln Pro Arg Glu Pro Gln Val Tyr Thr Leu Pro
                195                 200                 205

Pro Ser Arg Glu Glu Met Thr Lys Asn Gln Val Ser Leu Thr Cys Leu
                210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Lys Leu Thr Val Asp Lys Ser Arg
                260                 265                 270

Trp Gln Gln Gly Asn Val Phe Ser Cys Ser Val Met His Glu Ala Leu
                275                 280                 285

His Asn His Tyr Thr Gln Lys Ser Leu Ser Leu Ser Pro Gly Lys
    290                 295                 300
```

```
<210> SEQ ID NO 18
<211> LENGTH: 294
<212> TYPE: PRT
<213> ORGANISM: Artificial Sequence
<220> FEATURE:
<223> OTHER INFORMATION: huNRG1(S177-S228)(3H8)::3x(G4Q)::huFcSEFL2 (Pb)

<400> SEQUENCE: 18

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
                35                  40                  45

Phe Met Ala Ser Gly Gly Gly Gly Gln Gly Gly Gly Gln Gly Gly
                50                  55                  60

Gly Gly Gln Asp Lys Thr His Thr Cys Pro Pro Cys Pro Ala Pro Glu
```

-continued

```
65                    70                   75                   80

Leu Leu Gly Gly Pro Ser Val Phe Leu Phe Pro Pro Lys Pro Lys Asp
            85                   90                   95

Thr Leu Met Ile Ser Arg Thr Pro Glu Val Thr Cys Val Val Val Asp
            100                  105                  110

Val Ser His Glu Asp Pro Glu Val Lys Phe Asn Trp Tyr Val Asp Gly
            115                  120                  125

Val Glu Val His Asn Ala Lys Thr Lys Pro Cys Glu Glu Gln Tyr Gly
        130                  135                  140

Ser Thr Tyr Arg Cys Val Ser Val Leu Thr Val Leu His Gln Asp Trp
145                  150                  155                  160

Leu Asn Gly Lys Glu Tyr Lys Cys Lys Val Ser Asn Lys Ala Leu Pro
            165                  170                  175

Ala Pro Ile Glu Lys Thr Ile Ser Lys Ala Lys Gly Gln Pro Arg Glu
            180                  185                  190

Pro Gln Val Tyr Thr Leu Pro Pro Ser Arg Glu Glu Met Thr Lys Asn
            195                  200                  205

Gln Val Ser Leu Thr Cys Leu Val Lys Gly Phe Tyr Pro Ser Asp Ile
        210                  215                  220

Ala Val Glu Trp Glu Ser Asn Gly Gln Pro Glu Asn Asn Tyr Lys Thr
225                  230                  235                  240

Thr Pro Pro Val Leu Asp Ser Asp Gly Ser Phe Phe Leu Tyr Ser Lys
            245                  250                  255

Leu Thr Val Asp Lys Ser Arg Trp Gln Gln Gly Asn Val Phe Ser Cys
            260                  265                  270

Ser Val Met His Glu Ala Leu His Asn His Tyr Thr Gln Lys Ser Leu
        275                  280                  285

Ser Leu Ser Pro Gly Lys
        290

<210> SEQ ID NO 19
<211> LENGTH: 290
<212> TYPE: PRT
<213> ORGANISM: Artificial Sequence
<220> FEATURE:
<223> OTHER INFORMATION: huNRG1(S177-Q237)(NRGE1C)::GG::huFcSEFL2 (Pb)

<400> SEQUENCE: 19

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
```

```
        130              135              140
Cys Val Ser Val Leu Thr Val Leu His Gln Asp Trp Leu Asn Gly Lys
145              150              155              160

Glu Tyr Lys Cys Lys Val Ser Asn Lys Ala Leu Pro Ala Pro Ile Glu
              165              170              175

Lys Thr Ile Ser Lys Ala Lys Gly Gln Pro Arg Glu Pro Gln Val Tyr
              180              185              190

Thr Leu Pro Pro Ser Arg Glu Glu Met Thr Lys Asn Gln Val Ser Leu
              195              200              205

Thr Cys Leu Val Lys Gly Phe Tyr Pro Ser Asp Ile Ala Val Glu Trp
              210              215              220

Glu Ser Asn Gly Gln Pro Glu Asn Asn Tyr Lys Thr Thr Pro Pro Val
225              230              235              240

Leu Asp Ser Asp Gly Ser Phe Phe Leu Tyr Ser Lys Leu Thr Val Asp
              245              250              255

Lys Ser Arg Trp Gln Gln Gly Asn Val Phe Ser Cys Ser Val Met His
              260              265              270

Glu Ala Leu His Asn His Tyr Thr Gln Lys Ser Leu Ser Leu Ser Pro
              275              280              285

Gly Lys
    290

<210> SEQ ID NO 20
<211> LENGTH: 231
<212> TYPE: PRT
<213> ORGANISM: Artificial Sequence
<220> FEATURE:
<223> OTHER INFORMATION: huNRG1(S177-S228)(NRGE1C)::3x(G4Q)::huFcSEFL2
     (Pb)

<400> SEQUENCE: 20

Gly Gly Gly Gln Asp Lys Thr His Thr Cys Pro Pro Cys Pro Ala Pro
1               5               10              15

Glu Leu Leu Gly Gly Pro Ser Val Phe Leu Phe Pro Pro Lys Pro Lys
              20              25              30

Asp Thr Leu Met Ile Ser Arg Thr Pro Glu Val Thr Cys Val Val Val
              35              40              45

Asp Val Ser His Glu Asp Pro Glu Val Lys Phe Asn Trp Tyr Val Asp
              50              55              60

Gly Val Glu Val His Asn Ala Lys Thr Lys Pro Cys Glu Glu Gln Tyr
65              70              75              80

Gly Ser Thr Tyr Arg Cys Val Ser Val Leu Thr Val Leu His Gln Asp
              85              90              95

Trp Leu Asn Gly Lys Glu Tyr Lys Cys Lys Val Ser Asn Lys Ala Leu
              100             105             110

Pro Ala Pro Ile Glu Lys Thr Ile Ser Lys Ala Lys Gly Gln Pro Arg
              115             120             125

Glu Pro Gln Val Tyr Thr Leu Pro Pro Ser Arg Glu Glu Met Thr Lys
              130             135             140

Asn Gln Val Ser Leu Thr Cys Leu Val Lys Gly Phe Tyr Pro Ser Asp
145             150             155             160

Ile Ala Val Glu Trp Glu Ser Asn Gly Gln Pro Glu Asn Asn Tyr Lys
              165             170             175

Thr Thr Pro Pro Val Leu Asp Ser Asp Gly Ser Phe Phe Leu Tyr Ser
              180             185             190
```

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 21
<211> LENGTH: 150
<212> TYPE: PRT
<213> ORGANISM: Artificial Sequence
<220> FEATURE:
<223> OTHER INFORMATION: huNRG1(S177-S228)(NRGE1C)::3x(G4Q)::huFcSEFL2
      (Pb)

<400> SEQUENCE: 21

Ser Thr Tyr Arg Cys Val Ser Val Leu Thr Val Leu His Gln Asp Trp
1               5                   10                  15

Leu Asn Gly Lys Glu Tyr Lys Cys Lys Val Ser Asn Lys Ala Leu Pro
            20                  25                  30

Ala Pro Ile Glu Lys Thr Ile Ser Lys Ala Lys Gly Gln Pro Arg Glu
        35                  40                  45

Pro Gln Val Tyr Thr Leu Pro Pro Ser Arg Glu Glu Met Thr Lys Asn
    50                  55                  60

Gln Val Ser Leu Thr Cys Leu Val Lys Gly Phe Tyr Pro Ser Asp Ile
65                  70                  75                  80

Ala Val Glu Trp Glu Ser Asn Gly Gln Pro Glu Asn Asn Tyr Lys Thr
                85                  90                  95

Thr Pro Pro Val Leu Asp Ser Asp Gly Ser Phe Phe Leu Tyr Ser Lys
            100                 105                 110

Leu Thr Val Asp Lys Ser Arg Trp Gln Gln Gly Asn Val Phe Ser Cys
        115                 120                 125

Ser Val Met His Glu Ala Leu His Asn His Tyr Thr Gln Lys Ser Leu
    130                 135                 140

Ser Leu Ser Pro Gly Lys
145                 150

<210> SEQ ID NO 22
<211> LENGTH: 290
<212> TYPE: PRT
<213> ORGANISM: Artificial Sequence
<220> FEATURE:
<223> OTHER INFORMATION: huNRG1(S177-Q237)(NRGE1D)::GG::huFcSEFL2 (Pb)

<400> SEQUENCE: 22

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu

```
                    100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290

<210> SEQ ID NO 23
<211> LENGTH: 303
<212> TYPE: PRT
<213> ORGANISM: Artificial Sequence
<220> FEATURE:
<223> OTHER INFORMATION: huNRG1(S177-Q237)(NRGE1D)::3x(G4Q)::huFcSEFL2
      (Pb)

<400> SEQUENCE: 23

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Gly
    50                  55                  60

Gly Gln Gly Gly Gly Gly Gln Gly Gly Gly Gln Asp Lys Thr His
65                  70                  75                  80

Thr Cys Pro Pro Cys Pro Ala Pro Glu Leu Leu Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser His Glu Asp Pro Glu
        115                 120                 125

Val Lys Phe Asn Trp Tyr Val Asp Gly Val Glu Val His Asn Ala Lys
        130                 135                 140

Thr Lys Pro Cys Glu Glu Gln Tyr Gly Ser Thr Tyr Arg Cys Val Ser
145                 150                 155                 160
```

```
Val Leu Thr Val Leu His Gln Asp Trp Leu Asn Gly Lys Glu Tyr Lys
            165                 170                 175

Cys Lys Val Ser Asn Lys Ala Leu Pro Ala Pro Ile Glu Lys Thr Ile
            180                 185                 190

Ser Lys Ala Lys Gly Gln Pro Arg Glu Pro Gln Val Tyr Thr Leu Pro
            195                 200                 205

Pro Ser Arg Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
            245                 250                 255

Asp Gly Ser Phe Phe Leu Tyr Ser Lys Leu Thr Val Asp Lys Ser Arg
            260                 265                 270

Trp Gln Gln Gly Asn Val Phe Ser Cys Ser Val Met His Glu Ala Leu
        275                 280                 285

His Asn His Tyr Thr Gln Lys Ser Leu Ser Leu Ser Pro Gly Lys
    290                 295                 300

<210> SEQ ID NO 24
<211> LENGTH: 294
<212> TYPE: PRT
<213> ORGANISM: Artificial Sequence
<220> FEATURE:
<223> OTHER INFORMATION: huNRG1(S177-S228)(NRGE1D)::3x(G4Q)::huFcSEFL2
      (Pb)

<400> SEQUENCE: 24

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Gly Gly Gly Gln Gly Gly Gly Gln Gly Gly
    50                  55                  60

Gly Gly Gln Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
            85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
            115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
            165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220
```

-continued

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
        290

<210> SEQ ID NO 25
<211> LENGTH: 290
<212> TYPE: PRT
<213> ORGANISM: Artificial Sequence
<220> FEATURE:
<223> OTHER INFORMATION: huNRG1(S177-Q237)(wt)::GG::huFcSEFL2 (Pb)

<400> SEQUENCE: 25

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
                20                  25                  30

Leu Cys Lys Cys Pro Asn Glu Phe Thr Gly Asp Arg Cys Gln Asn Tyr
            35                  40                  45

Val Met Ala Ser Phe Tyr Lys Ala Glu Glu Leu Tyr Gln Gly Gly Asp
        50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290

<210> SEQ ID NO 26
<211> LENGTH: 295
<212> TYPE: PRT
<213> ORGANISM: Artificial Sequence
<220> FEATURE:
<223> OTHER INFORMATION: huNRG1(S177-F229)(wt)::3x(G4Q)::huFcSEFL2 (Pb)

<400> SEQUENCE: 26

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
            35                  40                  45

Val Met Ala Ser Phe Gly Gly Gly Gln Gly Gly Gly Gly Gln Gly
    50                  55                  60

Gly Gly Gly Gln Asp Lys Thr His Thr Cys Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
            115                 120                 125

Gly Val Glu Val His Asn Ala Lys Thr Lys Pro Cys Glu Glu Gln Tyr
            130                 135                 140

Gly Ser Thr Tyr Arg Cys Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
                180                 185                 190

Glu Pro Gln Val Tyr Thr Leu Pro Pro Ser Arg Glu Glu Met Thr Lys
            195                 200                 205

Asn Gln Val Ser Leu Thr Cys Leu Val Lys Gly Phe Tyr Pro Ser Asp
            210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
                260                 265                 270

Cys Ser Val Met His Glu Ala Leu His Asn His Tyr Thr Gln Lys Ser
                275                 280                 285

Leu Ser Leu Ser Pro Gly Lys
    290                 295

<210> SEQ ID NO 27
<211> LENGTH: 231
<212> TYPE: PRT
<213> ORGANISM: Artificial Sequence
<220> FEATURE:
<223> OTHER INFORMATION: huNRG1(S177-Q237)(wt)::3x(G4Q)::huFcSEFL2 (Pb)

```
<400> SEQUENCE: 27

Gly Gly Gly Gln Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Cys Glu Glu Gln Tyr
65                  70                  75                  80

Gly Ser Thr Tyr Arg Cys Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 28
<211> LENGTH: 150
<212> TYPE: PRT
<213> ORGANISM: Artificial Sequence
<220> FEATURE:
<223> OTHER INFORMATION: huNRG1(S177-S228)(wt)::3x(G4Q)::huFcSEFL2 (Pb)

<400> SEQUENCE: 28

Ser Thr Tyr Arg Cys Val Ser Val Leu Thr Val Leu His Gln Asp Trp
1               5                   10                  15

Leu Asn Gly Lys Glu Tyr Lys Cys Lys Val Ser Asn Lys Ala Leu Pro
            20                  25                  30

Ala Pro Ile Glu Lys Thr Ile Ser Lys Ala Lys Gly Gln Pro Arg Glu
        35                  40                  45

Pro Gln Val Tyr Thr Leu Pro Pro Ser Arg Glu Glu Met Thr Lys Asn
    50                  55                  60

Gln Val Ser Leu Thr Cys Leu Val Lys Gly Phe Tyr Pro Ser Asp Ile
65                  70                  75                  80

Ala Val Glu Trp Glu Ser Asn Gly Gln Pro Glu Asn Asn Tyr Lys Thr
                85                  90                  95

Thr Pro Pro Val Leu Asp Ser Asp Gly Ser Phe Phe Leu Tyr Ser Lys
                100                 105                 110

Leu Thr Val Asp Lys Ser Arg Trp Gln Gln Gly Asn Val Phe Ser Cys
```

-continued

```
            115                 120                 125

Ser Val Met His Glu Ala Leu His Asn His Tyr Thr Gln Lys Ser Leu
    130                 135                 140

Ser Leu Ser Pro Gly Lys
145                 150

<210> SEQ ID NO 29
<211> LENGTH: 290
<212> TYPE: PRT
<213> ORGANISM: Artificial Sequence
<220> FEATURE:
<223> OTHER INFORMATION: huNRG1(S177-Q237)(NRGE1A)::GG::huFcSEFL2 (Pb)

<400> SEQUENCE: 29

Ser His Leu Val Lys Cys Ala Glu Asn Asp Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
            165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
            245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290

<210> SEQ ID NO 30
<211> LENGTH: 290
<212> TYPE: PRT
```

```
<213> ORGANISM: Artificial Sequence
<220> FEATURE:
<223> OTHER INFORMATION: huNRG1(S177-Q237)(NRGE1B)::GG::huFcSEFL2 (Pb)

<400> SEQUENCE: 30

Ser His Leu Val Lys Cys Gly Glu Asn Asp Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
            245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
    275                 280                 285

Gly Lys
    290

<210> SEQ ID NO 31
<211> LENGTH: 290
<212> TYPE: PRT
<213> ORGANISM: Artificial Sequence
<220> FEATURE:
<223> OTHER INFORMATION: huNRG1(S177-Q237)(NRGE1E)::GG::huFcSEFL2 (Pb)

<400> SEQUENCE: 31

Ser His Leu Val Lys Cys Gly Glu Asn Asp Lys Ser Phe Cys Val Asn
1               5                   10                  15

Gly Gly Glu Cys Phe Met Ile Glu Gly Pro Ser Asn Pro Ser Arg Tyr
                20                  25                  30
```

```
Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290
```

```
<210> SEQ ID NO 32
<211> LENGTH: 290
<212> TYPE: PRT
<213> ORGANISM: Artificial Sequence
<220> FEATURE:
<223> OTHER INFORMATION: huNRG1(S177-Q237)(NRGE1F)::GG::huFcSEFL2 (Pb)

<400> SEQUENCE: 32
```

```
Ser His Leu Val Lys Cys Ala Glu Asn Asp Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95
```

-continued

```
Ser Arg Thr Pro Glu Val Thr Cys Val Val Val Asp Val Ser His Glu
            100             105              110

Asp Pro Glu Val Lys Phe Asn Trp Tyr Val Asp Gly Val Glu Val His
            115             120          125

Asn Ala Lys Thr Lys Pro Cys Glu Glu Gln Tyr Gly Ser Thr Tyr Arg
    130              135             140

Cys Val Ser Val Leu Thr Val Leu His Gln Asp Trp Leu Asn Gly Lys
145                150             155              160

Glu Tyr Lys Cys Lys Val Ser Asn Lys Ala Leu Pro Ala Pro Ile Glu
                165             170              175

Lys Thr Ile Ser Lys Ala Lys Gly Gln Pro Arg Glu Pro Gln Val Tyr
                180             185          190

Thr Leu Pro Pro Ser Arg Glu Glu Met Thr Lys Asn Gln Val Ser Leu
            195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235              240

Leu Asp Ser Asp Gly Ser Phe Phe Leu Tyr Ser Lys Leu Thr Val Asp
                245             250             255

Lys Ser Arg Trp Gln Gln Gly Asn Val Phe Ser Cys Ser Val Met His
                260             265             270

Glu Ala Leu His Asn His Tyr Thr Gln Lys Ser Leu Ser Leu Ser Pro
            275             280             285

Gly Lys
    290
```

```
<210> SEQ ID NO 33
<211> LENGTH: 290
<212> TYPE: PRT
<213> ORGANISM: Artificial Sequence
<220> FEATURE:
<223> OTHER INFORMATION: huNRG1(S177-Q237)(NRGE1G)::GG::huFcSEFL2 (Pb)

<400> SEQUENCE: 33
```

```
Ser His Leu Val Lys Cys Gly Glu Lys His Lys Ser Phe Cys Val Asn
1                5               10              15

Gly Gly Glu Cys Tyr Met Val Glu Gly Ser Ser Ile Pro Ser Arg Tyr
            20              25              30

Leu Cys Lys Cys Pro Asn Glu Phe Thr Gly Asp Arg Cys Gln Asn Asp
        35              40              45

Phe Met Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
                85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
            115             120          125

Asn Ala Lys Thr Lys Pro Cys Glu Glu Gln Tyr Gly Ser Thr Tyr Arg
    130             135             140

Cys Val Ser Val Leu Thr Val Leu His Gln Asp Trp Leu Asn Gly Lys
145             150             155              160
```

```
Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
                195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
                275                 280                 285

Gly Lys
    290
```

```
<210> SEQ ID NO 34
<211> LENGTH: 290
<212> TYPE: PRT
<213> ORGANISM: Artificial Sequence
<220> FEATURE:
<223> OTHER INFORMATION: huNRG1(S177-Q237)(NRGE1H)::GG::huFcSEFL2 (Pb)

<400> SEQUENCE: 34
```

```
Ser His Leu Val Lys Cys Gly Glu Ser His Lys Ser Phe Cys Val Asn
1                   5                   10                  15

Gly Gly Glu Cys Phe Met Ile Glu Gly Pro Ser Asn Pro Ser Arg Tyr
                20                  25                  30

Leu Cys Lys Cys Pro Asn Glu Phe Thr Gly Asp Arg Cys Gln Asn Asp
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
                195                 200                 205

Thr Cys Leu Val Lys Gly Phe Tyr Pro Ser Asp Ile Ala Val Glu Trp
    210                 215                 220
```

```
Glu Ser Asn Gly Gln Pro Glu Asn Asn Tyr Lys Thr Thr Pro Pro Val
225             230             235             240

Leu Asp Ser Asp Gly Ser Phe Phe Leu Tyr Ser Lys Leu Thr Val Asp
                245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
        275             280             285

Gly Lys
    290

<210> SEQ ID NO 35
<211> LENGTH: 290
<212> TYPE: PRT
<213> ORGANISM: Artificial Sequence
<220> FEATURE:
<223> OTHER INFORMATION: huNRG1(S177-Q237)(NRGE1J)::GG::huFcSEFL2 (Pb)

<400> SEQUENCE: 35

Ser His Leu Val Lys Cys Gly Glu Asn Asp Lys Ser Phe Cys Val Asn
1               5               10              15

Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Asp Asp
        35              40              45

Phe Met Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
            85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
        115             120             125

Asn Ala Lys Thr Lys Pro Cys Glu Glu Gln Tyr Gly Ser Thr Tyr Arg
        130             135             140

Cys Val Ser Val Leu Thr Val Leu His Gln Asp Trp Leu Asn Gly Lys
145             150             155             160

Glu Tyr Lys Cys Lys Val Ser Asn Lys Ala Leu Pro Ala Pro Ile Glu
            165             170             175

Lys Thr Ile Ser Lys Ala Lys Gly Gln Pro Arg Glu Pro Gln Val Tyr
            180             185             190

Thr Leu Pro Pro Ser Arg Glu Glu Met Thr Lys Asn Gln Val Ser Leu
            195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235             240

Leu Asp Ser Asp Gly Ser Phe Phe Leu Tyr Ser Lys Leu Thr Val Asp
                245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
        275             280             285
```

-continued

```
Gly Lys
    290

<210> SEQ ID NO 36
<211> LENGTH: 290
<212> TYPE: PRT
<213> ORGANISM: Artificial Sequence
<220> FEATURE:
<223> OTHER INFORMATION: huNRG1(S177-Q237)(NRGE1J)::GG::huFcSEFL2 (Pb)

<400> SEQUENCE: 36

Ser His Leu Val Lys Cys Gly Glu Asn Asp Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 37
<211> LENGTH: 290
<212> TYPE: PRT
<213> ORGANISM: Artificial Sequence
<220> FEATURE:
<223> OTHER INFORMATION: huNRG1(S177-Q237)(NRGE1K)::GG::huFcSEFL2 (Pb)

<400> SEQUENCE: 37
```

-continued

```
Ser His Leu Val Lys Cys Ala Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290
```

```
<210> SEQ ID NO 38
<211> LENGTH: 290
<212> TYPE: PRT
<213> ORGANISM: Artificial Sequence
<220> FEATURE:
<223> OTHER INFORMATION: huNRG1(S177-Q237)(NRGE1L)::GG::huFcSEFL2 (Pb)

<400> SEQUENCE: 38
```

```
Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln Gly Gly Asp
    50                  55                  60
```

```
Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
            210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290
```

```
<210> SEQ ID NO 39
<211> LENGTH: 290
<212> TYPE: PRT
<213> ORGANISM: Artificial Sequence
<220> FEATURE:
<223> OTHER INFORMATION: huNRG1(S177-Q237)(NRGE1M)::GG::huFcSEFL2 (Pb)

<400> SEQUENCE: 39
```

```
Ser His Leu Val Lys Cys Gly Glu Asn Asp Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Phe
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
            115                 120                 125
```

-continued

```
Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
                195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
    275                 280                 285

Gly Lys
    290

<210> SEQ ID NO 40
<211> LENGTH: 290
<212> TYPE: PRT
<213> ORGANISM: Artificial Sequence
<220> FEATURE:
<223> OTHER INFORMATION: huNRG1(S177-Q237)(NRGE1N)::GG::huFcSEFL2 (Pb)

<400> SEQUENCE: 40

Ser His Leu Val Lys Cys Gly Glu Asn Asp Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Asp Phe
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
    115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190
```

```
Thr Leu Pro Pro Ser Arg Glu Glu Met Thr Lys Asn Gln Val Ser Leu
    195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
    275                 280                 285

Gly Lys
    290

<210> SEQ ID NO 41
<211> LENGTH: 290
<212> TYPE: PRT
<213> ORGANISM: Artificial Sequence
<220> FEATURE:
<223> OTHER INFORMATION: huNRG1(S177-Q237)(NRGE1O)::GG::huFcSEFL2 (Pb)

<400> SEQUENCE: 41

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Asp Phe
    35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
    115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
    195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255
```

-continued

```
Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 42
<211> LENGTH: 290
<212> TYPE: PRT
<213> ORGANISM: Artificial Sequence
<220> FEATURE:
<223> OTHER INFORMATION: huNRG1(S177-Q237)(1D3)::GG::huFcSEFL2 (Pb)

<400> SEQUENCE: 42

Ser His Leu Val Lys Cys Ala Glu Ser His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Phe
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
            165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
            245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 43
```

```
<211> LENGTH: 290
<212> TYPE: PRT
<213> ORGANISM: Artificial Sequence
<220> FEATURE:
<223> OTHER INFORMATION: huNRG1(S177-Q237)(1D3)::GG::huFcSEFL2 (Pb)

<400> SEQUENCE: 43

Ser His Leu Val Lys Cys Gly Glu Asn Asp Lys Ser Phe Cys Val Asn
1               5                   10                  15

Gly Gly Glu Cys Phe Val Ile Glu Asp Pro Ser Ile Pro Ser Arg Tyr
            20                  25                  30

Leu Cys Lys Cys Pro Asn Glu Phe Thr Gly Asp Arg Cys Gln Asn Asp
        35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
                115                 120                 125

Asn Ala Lys Thr Lys Pro Cys Glu Glu Gln Tyr Gly Ser Thr Tyr Arg
            130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
                195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
        275                 280                 285

Gly Lys
    290

<210> SEQ ID NO 44
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47A_D48P_F49H_M50I)
      huIgG1z SELF2 Fc

<400> SEQUENCE: 44

Ser His Leu Val Lys Cys Gly Glu Lys His Lys Ser Phe Cys Val Asn
1               5                   10                  15
```

```
Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Ala Pro
        35              40              45

His Ile Ala Ser Phe Gly Gly Gly Gly Glu Gly Gly Gly Gly Ala Gly
    50              55              60

Gly Gly Gly Asp Lys Thr His Thr Cys Pro Pro Cys Pro Ala Pro Glu
65              70              75              80

Leu Leu Gly Gly Pro Ser Val Phe Leu Phe Pro Pro Lys Pro Lys Asp
            85              90              95

Thr Leu Met Ile Ser Arg Thr Pro Glu Val Thr Cys Val Val Val Asp
            100             105             110

Val Ser His Glu Asp Pro Glu Val Lys Phe Asn Trp Tyr Val Asp Gly
        115             120             125

Val Glu Val His Asn Ala Lys Thr Lys Pro Cys Glu Glu Gln Tyr Gly
    130             135             140

Ser Thr Tyr Arg Cys Val Ser Val Leu Thr Val Leu His Gln Asp Trp
145             150             155             160

Leu Asn Gly Lys Glu Tyr Lys Cys Lys Val Ser Asn Lys Ala Leu Pro
            165             170             175

Ala Pro Ile Glu Lys Thr Ile Ser Lys Ala Lys Gly Gln Pro Arg Glu
            180             185             190

Pro Gln Val Tyr Thr Leu Pro Pro Ser Arg Glu Glu Met Thr Lys Asn
            195             200             205

Gln Val Ser Leu Thr Cys Leu Val Lys Gly Phe Tyr Pro Ser Asp Ile
    210             215             220

Ala Val Glu Trp Glu Ser Asn Gly Gln Pro Glu Asn Asn Tyr Lys Thr
225             230             235             240

Thr Pro Pro Val Leu Asp Ser Asp Gly Ser Phe Phe Leu Tyr Ser Lys
            245             250             255

Leu Thr Val Asp Lys Ser Arg Trp Gln Gln Gly Asn Val Phe Ser Cys
            260             265             270

Ser Val Met His Glu Ala Leu His Asn His Tyr Thr Gln Lys Ser Leu
            275             280             285

Ser Leu Ser Pro Gly Lys
            290

<210> SEQ ID NO 45
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47A_D48P_F49H_M50I)
      huIgG1z SELF2 Fc

<400> SEQUENCE: 45

Ser His Leu Val Lys Cys Gly Glu Lys His Lys Ser Phe Cys Val Asn
1               5               10              15

Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Ala Pro
        35              40              45

His Ile Ala Ser Phe Gly Gly Gly Gly Glu Gly Gly Gly Gly Ala Gly
    50              55              60

Gly Gly Gly Asp Lys Thr His Thr Cys Pro Pro Cys Pro Ala Pro Glu
65              70              75              80
```

-continued

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
            275                 280                 285

Ser Leu Ser Pro Gly Lys
        290

<210> SEQ ID NO 46
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47K_D48T_F49S_M50L)
      huIgG1z SELF2 Fc

<400> SEQUENCE: 46

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
                20                  25                  30

Leu Cys Lys Cys Pro Asn Glu Phe Thr Gly Asp Arg Cys Gln Lys Thr
            35                  40                  45

Ser Leu Ala Ser Phe Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly

-continued

```
           130              135              140

Ser Thr Tyr Arg Cys Val Ser Val Leu Thr Val Leu His Gln Asp Trp
145               150              155              160

Leu Asn Gly Lys Glu Tyr Lys Cys Lys Val Ser Asn Lys Ala Leu Pro
                165              170              175

Ala Pro Ile Glu Lys Thr Ile Ser Lys Ala Lys Gly Gln Pro Arg Glu
                180              185              190

Pro Gln Val Tyr Thr Leu Pro Pro Ser Arg Glu Glu Met Thr Lys Asn
            195              200              205

Gln Val Ser Leu Thr Cys Leu Val Lys Gly Phe Tyr Pro Ser Asp Ile
        210              215              220

Ala Val Glu Trp Glu Ser Asn Gly Gln Pro Glu Asn Asn Tyr Lys Thr
225               230              235              240

Thr Pro Pro Val Leu Asp Ser Asp Gly Ser Phe Phe Leu Tyr Ser Lys
                245              250              255

Leu Thr Val Asp Lys Ser Arg Trp Gln Gln Gly Asn Val Phe Ser Cys
                260              265              270

Ser Val Met His Glu Ala Leu His Asn His Tyr Thr Gln Lys Ser Leu
            275              280              285

Ser Leu Ser Pro Gly Lys
        290
```

```
<210> SEQ ID NO 47
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47Q_D48S_M50P)
      huIgG1z SELF2 Fc

<400> SEQUENCE: 47
```

```
Ser His Leu Val Lys Cys Gly Glu Lys His Lys Ser Phe Cys Val Asn
1               5               10               15

Gly Gly Glu Cys Phe Met Ile Glu Gly Pro Ser Asn Pro Ser Arg Tyr
            20               25               30

Leu Cys Lys Cys Pro Asn Glu Phe Thr Gly Asp Arg Cys Gln Gln Ser
        35               40               45

Phe Pro Ala Ser Phe Gly Gly Gly Gly Glu Gly Gly Gly Gly Ala Gly
    50               55               60

Gly Gly Gly Asp Lys Thr His Thr Cys Pro Pro Cys Pro Ala Pro Glu
65               70               75               80

Leu Leu Gly Gly Pro Ser Val Phe Leu Phe Pro Pro Lys Pro Lys Asp
                85               90               95

Thr Leu Met Ile Ser Arg Thr Pro Glu Val Thr Cys Val Val Val Asp
            100              105              110

Val Ser His Glu Asp Pro Glu Val Lys Phe Asn Trp Tyr Val Asp Gly
        115              120              125

Val Glu Val His Asn Ala Lys Thr Lys Pro Cys Glu Glu Gln Tyr Gly
        130              135              140

Ser Thr Tyr Arg Cys Val Ser Val Leu Thr Val Leu His Gln Asp Trp
145               150              155              160

Leu Asn Gly Lys Glu Tyr Lys Cys Lys Val Ser Asn Lys Ala Leu Pro
                165              170              175

Ala Pro Ile Glu Lys Thr Ile Ser Lys Ala Lys Gly Gln Pro Arg Glu
                180              185              190
```

```
Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
                275                 280                 285

Ser Leu Ser Pro Gly Lys
        290

<210> SEQ ID NO 48
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47S_D48A_F49L_M50T)
      huIgG1z SELF2 Fc

<400> SEQUENCE: 48

Ser His Leu Val Lys Cys Gly Glu Lys His Lys Ser Phe Cys Val Asn
1                   5                   10                  15

Gly Gly Glu Cys Phe Met Ile Glu Gly Pro Ser Asn Pro Ser Arg Tyr
                20                  25                  30

Leu Cys Lys Cys Pro Asn Glu Phe Thr Gly Asp Arg Cys Gln Ser Ala
        35                  40                  45

Leu Thr Ala Ser Phe Gly Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255
```

-continued

```
Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 49
<211> LENGTH: 294
<212> TYPE: PRT
<213> ORGANISM: Artificial Sequence
<220> FEATURE:
<223> OTHER INFORMATION: huNRG1(S177-F229)(NRGE1C) (E47S_D48T_F49R_M50V)
      huIgG1z SELF2 Fc

<400> SEQUENCE: 49

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Ser Thr
        35                  40                  45

Arg Val Ala Ser Phe Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290
```

-continued

<210> SEQ ID NO 50
<211> LENGTH: 294
<212> TYPE: PRT
<213> ORGANISM: Artificial Sequence
<220> FEATURE:
<223> OTHER INFORMATION: huNRG1(S177-F229)(NRGE1C) huIgG1z SELF2 Fc

<400> SEQUENCE: 50

```
Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290
```

<210> SEQ ID NO 51
<211> LENGTH: 294
<212> TYPE: PRT
<213> ORGANISM: Artificial Sequence
<220> FEATURE:
<223> OTHER INFORMATION: huNRG1(S177-F229)(NRGE1D) (E47K_D48L_F49D_M50I)
      huIgG1z SELF2 Fc

<400> SEQUENCE: 51

```
Ser His Leu Val Lys Cys Gly Glu Ser His Lys Ser Phe Cys Val Asn
1               5                   10                  15
```

-continued

```
Gly Gly Glu Cys Tyr Met Val Glu Gly Ser Ser Ile Pro Ser Arg Tyr
          20                  25                  30

Leu Cys Lys Cys Pro Asn Glu Phe Thr Gly Asp Arg Cys Gln Lys Leu
          35                  40                  45

Asp Ile Ala Ser Phe Gly Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                  85                  90                  95

Thr Leu Met Ile Ser Arg Thr Pro Glu Val Thr Cys Val Val Val Asp
          100                 105                 110

Val Ser His Glu Asp Pro Glu Val Lys Phe Asn Trp Tyr Val Asp Gly
          115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                  165                 170                 175

Ala Pro Ile Glu Lys Thr Ile Ser Lys Ala Lys Gly Gln Pro Arg Glu
          180                 185                 190

Pro Gln Val Tyr Thr Leu Pro Pro Ser Arg Glu Glu Met Thr Lys Asn
          195                 200                 205

Gln Val Ser Leu Thr Cys Leu Val Lys Gly Phe Tyr Pro Ser Asp Ile
          210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                  245                 250                 255

Leu Thr Val Asp Lys Ser Arg Trp Gln Gln Gly Asn Val Phe Ser Cys
                  260                 265                 270

Ser Val Met His Glu Ala Leu His Asn His Tyr Thr Gln Lys Ser Leu
                  275                 280                 285

Ser Leu Ser Pro Gly Lys
    290
```

```
<210> SEQ ID NO 52
<211> LENGTH: 294
<212> TYPE: PRT
<213> ORGANISM: Artificial Sequence
<220> FEATURE:
<223> OTHER INFORMATION: huNRG1(S177-F229)(NRGE1D) (E47S_D48S_F49E_M50L)
      huIgG1z SELF2 Fc

<400> SEQUENCE: 52
```

```
Ser His Leu Val Lys Cys Gly Glu Ser His Lys Ser Phe Cys Val Asn
1                   5                   10                  15

Gly Gly Glu Cys Tyr Met Val Glu Gly Ser Ser Ile Pro Ser Arg Tyr
          20                  25                  30

Leu Cys Lys Cys Pro Asn Glu Phe Thr Gly Asp Arg Cys Gln Ser Ser
          35                  40                  45

Glu Leu Ala Ser Phe Gly Gly Gly Gly Glu Gly Gly Gly Gly Ala Gly
    50                  55                  60

Gly Gly Gly Asp Lys Thr His Thr Cys Pro Pro Cys Pro Ala Pro Glu
```

-continued

```
65                70                75                80

Leu Leu Gly Gly Pro Ser Val Phe Leu Phe Pro Pro Lys Pro Lys Asp
                85                90                95

Thr Leu Met Ile Ser Arg Thr Pro Glu Val Thr Cys Val Val Val Asp
                100               105               110

Val Ser His Glu Asp Pro Glu Val Lys Phe Asn Trp Tyr Val Asp Gly
            115               120               125

Val Glu Val His Asn Ala Lys Thr Lys Pro Cys Glu Glu Gln Tyr Gly
        130               135               140

Ser Thr Tyr Arg Cys Val Ser Val Leu Thr Val Leu His Gln Asp Trp
145               150               155               160

Leu Asn Gly Lys Glu Tyr Lys Cys Lys Val Ser Asn Lys Ala Leu Pro
                165               170               175

Ala Pro Ile Glu Lys Thr Ile Ser Lys Ala Lys Gly Gln Pro Arg Glu
                180               185               190

Pro Gln Val Tyr Thr Leu Pro Pro Ser Arg Glu Glu Met Thr Lys Asn
            195               200               205

Gln Val Ser Leu Thr Cys Leu Val Lys Gly Phe Tyr Pro Ser Asp Ile
        210               215               220

Ala Val Glu Trp Glu Ser Asn Gly Gln Pro Glu Asn Asn Tyr Lys Thr
225               230               235               240

Thr Pro Pro Val Leu Asp Ser Asp Gly Ser Phe Phe Leu Tyr Ser Lys
                245               250               255

Leu Thr Val Asp Lys Ser Arg Trp Gln Gln Gly Asn Val Phe Ser Cys
                260               265               270

Ser Val Met His Glu Ala Leu His Asn His Tyr Thr Gln Lys Ser Leu
            275               280               285

Ser Leu Ser Pro Gly Lys
        290

<210> SEQ ID NO 53
<211> LENGTH: 294
<212> TYPE: PRT
<213> ORGANISM: Artificial Sequence
<220> FEATURE:
<223> OTHER INFORMATION: huNRG1(S177-F229)(NRGE1D) (E47T_D48S_F49L_M50L)
      huIgG1z SELF2 Fc

<400> SEQUENCE: 53

Ser His Leu Val Lys Cys Gly Glu Ser His Lys Ser Phe Cys Val Asn
1                 5                 10                15

Gly Gly Glu Cys Tyr Met Val Glu Gly Ser Ser Ile Pro Ser Arg Tyr
                20                25                30

Leu Cys Lys Cys Pro Asn Glu Phe Thr Gly Asp Arg Cys Gln Thr Ser
            35                40                45

Leu Leu Ala Ser Phe Gly Gly Gly Glu Gly Gly Gly Gly Ala Gly
        50                55                60

Gly Gly Gly Asp Lys Thr His Thr Cys Pro Pro Cys Pro Ala Pro Glu
65                70                75                80

Leu Leu Gly Gly Pro Ser Val Phe Leu Phe Pro Pro Lys Pro Lys Asp
                85                90                95

Thr Leu Met Ile Ser Arg Thr Pro Glu Val Thr Cys Val Val Val Asp
                100               105               110

Val Ser His Glu Asp Pro Glu Val Lys Phe Asn Trp Tyr Val Asp Gly
            115               120               125
```

-continued

```
Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
                195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
                275                 280                 285

Ser Leu Ser Pro Gly Lys
    290

<210> SEQ ID NO 54
<211> LENGTH: 294
<212> TYPE: PRT
<213> ORGANISM: Artificial Sequence
<220> FEATURE:
<223> OTHER INFORMATION: huNRG1(S177-F229) huIgG1z SELF2 Fc

<400> SEQUENCE: 54

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
                35                  40                  45

Phe Met Ala Ser Phe Gly Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
                115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190
```

-continued

```
Pro Gln Val Tyr Thr Leu Pro Pro Ser Arg Glu Glu Met Thr Lys Asn
    195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
                275                 280                 285

Ser Leu Ser Pro Gly Lys
    290

<210> SEQ ID NO 55
<211> LENGTH: 294
<212> TYPE: PRT
<213> ORGANISM: Artificial Sequence
<220> FEATURE:
<223> OTHER INFORMATION: huNRG1(S177-F229) huIgG1z SELF2 Fc

<400> SEQUENCE: 55

Ser His Leu Val Lys Cys Ala Glu Lys Glu Lys Thr Phe Cys Val Asn
1                   5                   10                  15

Gly Gly Glu Cys Phe Met Val Lys Asp Leu Ser Asn Pro Ser Arg Tyr
                20                  25                  30

Leu Cys Lys Cys Pro Asn Glu Phe Thr Gly Asp Arg Cys Gln Asn Tyr
                35                  40                  45

Val Met Ala Ser Phe Gly Gly Gly Gly Glu Gly Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110

Val Ser His Glu Asp Pro Glu Val Lys Phe Asn Trp Tyr Val Asp Gly
                115                 120                 125

Val Glu Val His Asn Ala Lys Thr Lys Pro Cys Glu Glu Gln Tyr Gly
                130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
                180                 185                 190

Pro Gln Val Tyr Thr Leu Pro Pro Ser Arg Glu Glu Met Thr Lys Asn
                195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255
```

```
Leu Thr Val Asp Lys Ser Arg Trp Gln Gln Gly Asn Val Phe Ser Cys
        260                 265                 270

Ser Val Met His Glu Ala Leu His Asn His Tyr Thr Gln Lys Ser Leu
        275                 280                 285

Ser Leu Ser Pro Gly Lys
    290

<210> SEQ ID NO 56
<211> LENGTH: 73
<212> TYPE: PRT
<213> ORGANISM: Artificial Sequence
<220> FEATURE:
<223> OTHER INFORMATION: huNRG1(S177-F229)(NRGE1C) 6xHis

<400> SEQUENCE: 56

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gly Glu Gly Gly Gly Gly Ala Gly
    50                  55                  60

Gly Gly Gly His His His His His His
65                  70

<210> SEQ ID NO 57
<211> LENGTH: 73
<212> TYPE: PRT
<213> ORGANISM: Artificial Sequence
<220> FEATURE:
<223> OTHER INFORMATION: huNRG1(S177-F229)(NRGE1C) (D48T_F49Q_M50I)
      6xHis

<400> SEQUENCE: 57

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Glu Thr
        35                  40                  45

Gln Ile Ala Ser Phe Gly Gly Gly Gly Glu Gly Gly Gly Gly Ala Gly
    50                  55                  60

Gly Gly Gly His His His His His His
65                  70

<210> SEQ ID NO 58
<211> LENGTH: 73
<212> TYPE: PRT
<213> ORGANISM: Artificial Sequence
<220> FEATURE:
<223> OTHER INFORMATION: huNRG1(S177-F229)(NRGE1C) (E47A_D48P_F49H_M50I)
      6xHis

<400> SEQUENCE: 58

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Ala Pro
        35                  40                  45
```

-continued

```
His Ile Ala Ser Phe Gly Gly Gly Glu Gly Gly Gly Ala Gly
    50              55              60

Gly Gly Gly His His His His His His
65                  70

<210> SEQ ID NO 59
<211> LENGTH: 73
<212> TYPE: PRT
<213> ORGANISM: Artificial Sequence
<220> FEATURE:
<223> OTHER INFORMATION: huNRG1(S177-F229)(NRGE1C) (E47K_D48T_F49S_M50L)
      6xHis

<400> SEQUENCE: 59

Ser His Leu Val Lys Cys Gly Glu Lys His Lys Ser Phe Cys Val Asn
1               5               10              15

Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Lys Thr
        35              40              45

Ser Leu Ala Ser Phe Gly Gly Gly Gly Glu Gly Gly Gly Gly Ala Gly
    50              55              60

Gly Gly Gly His His His His His His
65                  70

<210> SEQ ID NO 60
<211> LENGTH: 73
<212> TYPE: PRT
<213> ORGANISM: Artificial Sequence
<220> FEATURE:
<223> OTHER INFORMATION: huNRG1(S177-F229)(NRGE1C) (E47Q_D48S_M50P)
      6xHis

<400> SEQUENCE: 60

Ser His Leu Val Lys Cys Gly Glu Lys His Lys Ser Phe Cys Val Asn
1               5               10              15

Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Gln Ser
        35              40              45

Phe Pro Ala Ser Phe Gly Gly Gly Gly Glu Gly Gly Gly Gly Ala Gly
    50              55              60

Gly Gly Gly His His His His His His
65                  70

<210> SEQ ID NO 61
<211> LENGTH: 73
<212> TYPE: PRT
<213> ORGANISM: Artificial Sequence
<220> FEATURE:
<223> OTHER INFORMATION: huNRG1(S177-F229)(NRGE1C) (E47S_D48A_F49L_M50T)
      6xHis

<400> SEQUENCE: 61

Ser His Leu Val Lys Cys Gly Glu Lys His Lys Ser Phe Cys Val Asn
1               5               10              15

Gly Gly Glu Cys Phe Met Ile Glu Gly Pro Ser Asn Pro Ser Arg Tyr
            20              25              30

Leu Cys Lys Cys Pro Asn Glu Phe Thr Gly Asp Arg Cys Gln Ser Ala
        35              40              45
```

-continued

Leu Thr Ala Ser Phe Gly Gly Gly Gly Glu Gly Gly Gly Gly Ala Gly
        50                  55                  60

Gly Gly Gly His His His His His His
65                  70

<210> SEQ ID NO 62
<211> LENGTH: 73
<212> TYPE: PRT
<213> ORGANISM: Artificial Sequence
<220> FEATURE:
<223> OTHER INFORMATION: huNRG1(S177-F229)(NRGE1C) (E47S_D48T_F49R_M50V)
      6xHis

<400> SEQUENCE: 62

Ser His Leu Val Lys Cys Gly Glu Lys His Lys Ser Phe Cys Val Asn
1                   5                   10                  15

Gly Gly Glu Cys Phe Met Ile Glu Gly Pro Ser Asn Pro Ser Arg Tyr
                20                  25                  30

Leu Cys Lys Cys Pro Asn Glu Phe Thr Gly Asp Arg Cys Gln Ser Thr
        35                  40                  45

Arg Val Ala Ser Phe Gly Gly Gly Gly Glu Gly Gly Gly Gly Ala Gly
    50                  55                  60

Gly Gly Gly His His His His His His
65                  70

<210> SEQ ID NO 63
<211> LENGTH: 73
<212> TYPE: PRT
<213> ORGANISM: Artificial Sequence
<220> FEATURE:
<223> OTHER INFORMATION: huNRG1(S177-F229)(NRGE1D) 6xHis

<400> SEQUENCE: 63

Ser His Leu Val Lys Cys Gly Glu Ser His Lys Ser Phe Cys Val Asn
1                   5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Gly Glu Gly Gly Gly Gly Ala Gly
    50                  55                  60

Gly Gly Gly His His His His His His
65                  70

<210> SEQ ID NO 64
<211> LENGTH: 73
<212> TYPE: PRT
<213> ORGANISM: Artificial Sequence
<220> FEATURE:
<223> OTHER INFORMATION: huNRG1(S177-F229)(NRGE1D) (E47K_D48L_F49D_M50I)
      6xHis

<400> SEQUENCE: 64

Ser His Leu Val Lys Cys Gly Glu Ser His Lys Ser Phe Cys Val Asn
1                   5                   10                  15

Gly Gly Glu Cys Tyr Met Val Glu Gly Ser Ser Ile Pro Ser Arg Tyr
                20                  25                  30

Leu Cys Lys Cys Pro Asn Glu Phe Thr Gly Asp Arg Cys Gln Lys Leu
        35                  40                  45

Asp Ile Ala Ser Phe Gly Gly Gly Gly Glu Gly Gly Gly Gly Ala Gly
    50                  55                  60

-continued

```
Gly Gly Gly His His His His His His
65              70

<210> SEQ ID NO 65
<211> LENGTH: 73
<212> TYPE: PRT
<213> ORGANISM: Artificial Sequence
<220> FEATURE:
<223> OTHER INFORMATION: huNRG1(S177-F229)(NRGE1D) (E47S_D48S_F49E_M50L)
      6xHis

<400> SEQUENCE: 65

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Ser Ser
        35                  40                  45

Glu Leu Ala Ser Phe Gly Gly Gly Gly Glu Gly Gly Gly Gly Ala Gly
    50                  55                  60

Gly Gly Gly His His His His His His
65              70

<210> SEQ ID NO 66
<211> LENGTH: 73
<212> TYPE: PRT
<213> ORGANISM: Artificial Sequence
<220> FEATURE:
<223> OTHER INFORMATION: huNRG1(S177-F229)(NRGE1D) (E47T_D48S_F49L_M50L)
      6xHis

<400> SEQUENCE: 66

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Thr Ser
        35                  40                  45

Leu Leu Ala Ser Phe Gly Gly Gly Gly Glu Gly Gly Gly Gly Ala Gly
    50                  55                  60

Gly Gly Gly His His His His His His
65              70

<210> SEQ ID NO 67
<211> LENGTH: 73
<212> TYPE: PRT
<213> ORGANISM: Artificial Sequence
<220> FEATURE:
<223> OTHER INFORMATION: huNRG1(S177-F229)(NRGE1D) (E47V_D48T_F49R_M50L)
      6xHis

<400> SEQUENCE: 67

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Val Thr
        35                  40                  45

Arg Leu Ala Ser Phe Gly Gly Gly Gly Glu Gly Gly Gly Gly Ala Gly
    50                  55                  60
```

```
Gly Gly Gly His His His His His His
65                  70

<210> SEQ ID NO 68
<211> LENGTH: 73
<212> TYPE: PRT
<213> ORGANISM: Artificial Sequence
<220> FEATURE:
<223> OTHER INFORMATION: huNRG1(S177-F229) 6xHis

<400> SEQUENCE: 68

Ser His Leu Val Lys Cys Ala Glu Lys Glu Lys Thr Phe Cys Val Asn
1               5                  10                 15

Gly Gly Glu Cys Phe Met Val Lys Asp Leu Ser Asn Pro Ser Arg Tyr
            20                 25                 30

Leu Cys Lys Cys Pro Asn Glu Phe Thr Gly Asp Arg Cys Gln Asn Tyr
        35                 40                 45

Val Met Ala Ser Phe Gly Gly Gly Glu Gly Gly Gly Gly Ala Gly
    50                 55                 60

Gly Gly Gly His His His His His His
65                  70

<210> SEQ ID NO 69
<211> LENGTH: 576
<212> TYPE: PRT
<213> ORGANISM: Artificial Sequence
<220> FEATURE:
<223> OTHER INFORMATION: :huFcSEFL2(desK):G4SG4:huNRG1(S177-F229)
      (NRGE1C)

<400> SEQUENCE: 69

Asp Lys Thr His Thr Cys Pro Pro Cys Pro Ala Pro Glu Leu Leu Gly
1               5                  10                 15

Gly Pro Ser Val Phe Leu Phe Pro Pro Lys Pro Lys Asp Thr Leu Met
            20                 25                 30

Ile Ser Arg Thr Pro Glu Val Thr Cys Val Val Val Asp Val Ser His
        35                 40                 45

Glu Asp Pro Glu Val Lys Phe Asn Trp Tyr Val Asp Gly Val Glu Val
    50                 55                 60

His Asn Ala Lys Thr Lys Pro Cys Glu Glu Gln Tyr Gly Ser Thr Tyr
65                  70                 75                 80

Arg Cys Val Ser Val Leu Thr Val Leu His Gln Asp Trp Leu Asn Gly
                85                 90                 95

Lys Glu Tyr Lys Cys Lys Val Ser Asn Lys Ala Leu Pro Ala Pro Ile
            100                105                110

Glu Lys Thr Ile Ser Lys Ala Lys Gly Gln Pro Arg Glu Pro Gln Val
        115                120                125

Tyr Thr Leu Pro Pro Ser Arg Glu Glu Met Thr Lys Asn Gln Val Ser
    130                135                140

Leu Thr Cys Leu Val Lys Gly Phe Tyr Pro Ser Asp Ile Ala Val Glu
145                150                155                160

Trp Glu Ser Asn Gly Gln Pro Glu Asn Asn Tyr Lys Thr Thr Pro Pro
                165                170                175

Val Leu Asp Ser Asp Gly Ser Phe Phe Leu Tyr Ser Lys Leu Thr Val
            180                185                190

Asp Lys Ser Arg Trp Gln Gln Gly Asn Val Phe Ser Cys Ser Val Met
        195                200                205

His Glu Ala Leu His Asn His Tyr Thr Gln Lys Ser Leu Ser Leu Ser
```

-continued

```
          210                   215                   220

Pro Gly Gly Gly Gly Ser Gly Gly Gly Gly Ser His Leu Val Lys
225                   230                   235                   240

Cys Gly Glu Lys His Lys Ser Phe Cys Val Asn Gly Gly Glu Cys Phe
                  245                   250                   255

Met Ile Glu Gly Pro Ser Asn Pro Ser Arg Tyr Leu Cys Lys Cys Pro
                  260                   265                   270

Asn Glu Phe Thr Gly Asp Arg Cys Gln Glu Asp Phe Met Ala Ser Phe
                  275                   280                   285

Asp Lys Thr His Thr Cys Pro Pro Cys Pro Ala Pro Glu Leu Leu Gly
                  290                   295                   300

Gly Pro Ser Val Phe Leu Phe Pro Pro Lys Pro Lys Asp Thr Leu Met
305                   310                   315                   320

Ile Ser Arg Thr Pro Glu Val Thr Cys Val Val Val Asp Val Ser His
                  325                   330                   335

Glu Asp Pro Glu Val Lys Phe Asn Trp Tyr Val Asp Gly Val Glu Val
                  340                   345                   350

His Asn Ala Lys Thr Lys Pro Cys Glu Glu Gln Tyr Gly Ser Thr Tyr
                  355                   360                   365

Arg Cys Val Ser Val Leu Thr Val Leu His Gln Asp Trp Leu Asn Gly
                  370                   375                   380

Lys Glu Tyr Lys Cys Lys Val Ser Asn Lys Ala Leu Pro Ala Pro Ile
385                   390                   395                   400

Glu Lys Thr Ile Ser Lys Ala Lys Gly Gln Pro Arg Glu Pro Gln Val
                  405                   410                   415

Tyr Thr Leu Pro Pro Ser Arg Glu Glu Met Thr Lys Asn Gln Val Ser
                  420                   425                   430

Leu Thr Cys Leu Val Lys Gly Phe Tyr Pro Ser Asp Ile Ala Val Glu
                  435                   440                   445

Trp Glu Ser Asn Gly Gln Pro Glu Asn Asn Tyr Lys Thr Thr Pro Pro
                  450                   455                   460

Val Leu Asp Ser Asp Gly Ser Phe Phe Leu Tyr Ser Lys Leu Thr Val
465                   470                   475                   480

Asp Lys Ser Arg Trp Gln Gln Gly Asn Val Phe Ser Cys Ser Val Met
                  485                   490                   495

His Glu Ala Leu His Asn His Tyr Thr Gln Lys Ser Leu Ser Leu Ser
                  500                   505                   510

Pro Gly Gly Gly Gly Gly Ser Gly Gly Gly Gly Ser His Leu Val Lys
                  515                   520                   525

Cys Gly Glu Lys His Lys Ser Phe Cys Val Asn Gly Gly Glu Cys Phe
                  530                   535                   540

Met Ile Glu Gly Pro Ser Asn Pro Ser Arg Tyr Leu Cys Lys Cys Pro
545                   550                   555                   560

Asn Glu Phe Thr Gly Asp Arg Cys Gln Glu Asp Phe Met Ala Ser Phe
                  565                   570                   575
```

<210> SEQ ID NO 70
<211> LENGTH: 576
<212> TYPE: PRT
<213> ORGANISM: Artificial Sequence
<220> FEATURE:
<223> OTHER INFORMATION: :huFcSEFL2(desK):G4SG4:huNRG1(S177-F229)
      (NRGE1D)

<400> SEQUENCE: 70

```
Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Cys Glu Glu Gln Tyr Gly Ser Thr Tyr
65              70              75              80

Arg Cys Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Tyr Thr Leu Pro Pro Ser Arg Glu Glu Met Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
            195             200             205

His Glu Ala Leu His Asn His Tyr Thr Gln Lys Ser Leu Ser Leu Ser
    210             215             220

Pro Gly Gly Gly Gly Ser Gly Gly Gly Gly Ser His Leu Val Lys
225             230             235             240

Cys Gly Glu Ser His Lys Ser Phe Cys Val Asn Gly Gly Glu Cys Tyr
            245             250             255

Met Val Glu Gly Ser Ser Ile Pro Ser Arg Tyr Leu Cys Lys Cys Pro
            260             265             270

Asn Glu Phe Thr Gly Asp Arg Cys Gln Glu Asp Phe Met Ala Ser Phe
    275             280             285

Asp Lys Thr His Thr Cys Pro Pro Cys Pro Ala Pro Glu Leu Leu Gly
    290             295             300

Gly Pro Ser Val Phe Leu Phe Pro Pro Lys Pro Lys Asp Thr Leu Met
305             310             315             320

Ile Ser Arg Thr Pro Glu Val Thr Cys Val Val Val Asp Val Ser His
            325             330             335

Glu Asp Pro Glu Val Lys Phe Asn Trp Tyr Val Asp Gly Val Glu Val
            340             345             350

His Asn Ala Lys Thr Lys Pro Cys Glu Glu Gln Tyr Gly Ser Thr Tyr
            355             360             365

Arg Cys Val Ser Val Leu Thr Val Leu His Gln Asp Trp Leu Asn Gly
    370             375             380

Lys Glu Tyr Lys Cys Lys Val Ser Asn Lys Ala Leu Pro Ala Pro Ile
385             390             395             400

Glu Lys Thr Ile Ser Lys Ala Lys Gly Gln Pro Arg Glu Pro Gln Val
            405             410             415

Tyr Thr Leu Pro Pro Ser Arg Glu Glu Met Thr Lys Asn Gln Val Ser
```

-continued

```
                420              425              430

Leu Thr Cys Leu Val Lys Gly Phe Tyr Pro Ser Asp Ile Ala Val Glu
        435              440              445

Trp Glu Ser Asn Gly Gln Pro Glu Asn Asn Tyr Lys Thr Thr Pro Pro
    450              455              460

Val Leu Asp Ser Asp Gly Ser Phe Phe Leu Tyr Ser Lys Leu Thr Val
465              470              475              480

Asp Lys Ser Arg Trp Gln Gln Gly Asn Val Phe Ser Cys Ser Val Met
            485              490              495

His Glu Ala Leu His Asn His Tyr Thr Gln Lys Ser Leu Ser Leu Ser
            500              505              510

Pro Gly Gly Gly Gly Ser Gly Gly Gly Ser His Leu Val Lys
        515              520              525

Cys Gly Glu Ser His Lys Ser Phe Cys Val Asn Gly Gly Glu Cys Tyr
        530              535              540

Met Val Glu Gly Ser Ser Ile Pro Ser Arg Tyr Leu Cys Lys Cys Pro
545              550              555              560

Asn Glu Phe Thr Gly Asp Arg Cys Gln Glu Asp Phe Met Ala Ser Phe
                565              570              575
```

<210> SEQ ID NO 71
<211> LENGTH: 592
<212> TYPE: PRT
<213> ORGANISM: Artificial Sequence
<220> FEATURE:
<223> OTHER INFORMATION: :huFcSEFL2(desK):G4SG4:huNRG1(S177-Q237)
      (NRGE1C)

<400> SEQUENCE: 71

```
Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Cys Glu Glu Gln Tyr Gly Ser Thr Tyr
65              70              75              80

Arg Cys Val Ser Val Leu Thr Val Leu His Gln Asp Trp Leu Asn Gly
            85              90              95

Lys Glu Tyr Lys Cys Lys Val Ser Asn Lys Ala Leu Pro Ala Pro Ile
            100             105             110

Glu Lys Thr Ile Ser Lys Ala Lys Gly Gln Pro Arg Glu Pro Gln Val
        115             120             125

Tyr Thr Leu Pro Pro Ser Arg Glu Glu Met Thr Lys Asn Gln Val Ser
    130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
            165             170             175

Val Leu Asp Ser Asp Gly Ser Phe Phe Leu Tyr Ser Lys Leu Thr Val
            180             185             190

Asp Lys Ser Arg Trp Gln Gln Gly Asn Val Phe Ser Cys Ser Val Met
        195             200             205
```

-continued

```
His Glu Ala Leu His Asn His Tyr Thr Gln Lys Ser Leu Ser Leu Ser
    210             215                 220
Pro Gly Gly Gly Gly Gly Ser Gly Gly Gly Gly Ser His Leu Val Lys
225             230                 235                 240
Cys Gly Glu Lys His Lys Ser Phe Cys Val Asn Gly Gly Glu Cys Phe
                245                 250                 255
Met Ile Glu Gly Pro Ser Asn Pro Ser Arg Tyr Leu Cys Lys Cys Pro
                260                 265                 270
Asn Glu Phe Thr Gly Asp Arg Cys Gln Glu Asp Phe Met Ala Ser Phe
            275                 280                 285
Tyr Lys Ala Glu Glu Leu Tyr Gln Asp Lys Thr His Thr Cys Pro Pro
        290                 295                 300
Cys Pro Ala Pro Glu Leu Leu Gly Gly Pro Ser Val Phe Leu Phe Pro
305                 310                 315                 320
Pro Lys Pro Lys Asp Thr Leu Met Ile Ser Arg Thr Pro Glu Val Thr
                325                 330                 335
Cys Val Val Val Asp Val Ser His Glu Asp Pro Glu Val Lys Phe Asn
            340                 345                 350
Trp Tyr Val Asp Gly Val Glu Val His Asn Ala Lys Thr Lys Pro Cys
        355                 360                 365
Glu Glu Gln Tyr Gly Ser Thr Tyr Arg Cys Val Ser Val Leu Thr Val
    370                 375                 380
Leu His Gln Asp Trp Leu Asn Gly Lys Glu Tyr Lys Cys Lys Val Ser
385                 390                 395                 400
Asn Lys Ala Leu Pro Ala Pro Ile Glu Lys Thr Ile Ser Lys Ala Lys
                405                 410                 415
Gly Gln Pro Arg Glu Pro Gln Val Tyr Thr Leu Pro Pro Ser Arg Glu
                420                 425                 430
Glu Met Thr Lys Asn Gln Val Ser Leu Thr Cys Leu Val Lys Gly Phe
            435                 440                 445
Tyr Pro Ser Asp Ile Ala Val Glu Trp Glu Ser Asn Gly Gln Pro Glu
        450                 455                 460
Asn Asn Tyr Lys Thr Thr Pro Pro Val Leu Asp Ser Asp Gly Ser Phe
465                 470                 475                 480
Phe Leu Tyr Ser Lys Leu Thr Val Asp Lys Ser Arg Trp Gln Gln Gly
                485                 490                 495
Asn Val Phe Ser Cys Ser Val Met His Glu Ala Leu His Asn His Tyr
                500                 505                 510
Thr Gln Lys Ser Leu Ser Leu Ser Pro Gly Gly Gly Gly Ser Gly
            515                 520                 525
Gly Gly Gly Ser His Leu Val Lys Cys Gly Glu Lys His Lys Ser Phe
        530                 535                 540
Cys Val Asn Gly Gly Glu Cys Phe Met Ile Glu Gly Pro Ser Asn Pro
545                 550                 555                 560
Ser Arg Tyr Leu Cys Lys Cys Pro Asn Glu Phe Thr Gly Asp Arg Cys
                565                 570                 575
Gln Glu Asp Phe Met Ala Ser Phe Tyr Lys Ala Glu Glu Leu Tyr Gln
                580                 585                 590
```

<210> SEQ ID NO 72
<211> LENGTH: 592
<212> TYPE: PRT
<213> ORGANISM: Artificial Sequence
<220> FEATURE:
<223> OTHER INFORMATION: :huFcSEFL2(desK):G4SG4:huNRG1(S177-Q237)

```
      (NRGE1D)

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Cys Glu Glu Gln Tyr Gly Ser Thr Tyr
65                  70                  75                  80

Arg Cys Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser His Leu Val Lys
225                 230                 235                 240

Cys Gly Glu Ser His Lys Ser Phe Cys Val Asn Gly Gly Glu Cys Tyr
                245                 250                 255

Met Val Glu Gly Ser Ser Ile Pro Ser Arg Tyr Leu Cys Lys Cys Pro
            260                 265                 270

Asn Glu Phe Thr Gly Asp Arg Cys Gln Glu Asp Phe Met Ala Ser Phe
            275                 280                 285

Tyr Lys Ala Glu Glu Leu Tyr Gln Asp Lys Thr His Thr Cys Pro Pro
    290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Cys
            355                 360                 365

Glu Glu Gln Tyr Gly Ser Thr Tyr Arg Cys Val Ser Val Leu Thr Val
    370                 375                 380

Leu His Gln Asp Trp Leu Asn Gly Lys Glu Tyr Lys Cys Lys Val Ser
385                 390                 395                 400
```

-continued

```
Asn Lys Ala Leu Pro Ala Pro Ile Glu Lys Thr Ile Ser Lys Ala Lys
              405             410             415

Gly Gln Pro Arg Glu Pro Gln Val Tyr Thr Leu Pro Pro Ser Arg Glu
              420             425             430

Glu Met Thr Lys Asn Gln Val Ser Leu Thr Cys Leu Val Lys Gly Phe
              435             440             445

Tyr Pro Ser Asp Ile Ala Val Glu Trp Glu Ser Asn Gly Gln Pro Glu
          450             455             460

Asn Asn Tyr Lys Thr Thr Pro Pro Val Leu Asp Ser Asp Gly Ser Phe
465             470             475             480

Phe Leu Tyr Ser Lys Leu Thr Val Asp Lys Ser Arg Trp Gln Gln Gly
              485             490             495

Asn Val Phe Ser Cys Ser Val Met His Glu Ala Leu His Asn His Tyr
              500             505             510

Thr Gln Lys Ser Leu Ser Leu Ser Pro Gly Gly Gly Gly Ser Gly
              515             520             525

Gly Gly Gly Ser His Leu Val Lys Cys Gly Glu Ser His Lys Ser Phe
          530             535             540

Cys Val Asn Gly Gly Glu Cys Tyr Met Val Glu Gly Ser Ser Ile Pro
545             550             555             560

Ser Arg Tyr Leu Cys Lys Cys Pro Asn Glu Phe Thr Gly Asp Arg Cys
              565             570             575

Gln Glu Asp Phe Met Ala Ser Phe Tyr Lys Ala Glu Glu Leu Tyr Gln
              580             585             590
```

```
<210> SEQ ID NO 73
<211> LENGTH: 515
<212> TYPE: PRT
<213> ORGANISM: Artificial Sequence
<220> FEATURE:
<223> OTHER INFORMATION: :huFcSEFL2(desK)v131(+):G4SG4:huNRG1(S177-F229)
       (NRGE1C)

<400> SEQUENCE: 73
```

```
Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
              20              25              30

Ile Ser Arg Thr Pro Glu Val Thr Cys Val Val Val Asp Val Ser His
          35              40              45

Glu Asp Pro Glu Val Lys Phe Asn Trp Tyr Val Asp Gly Val Glu Val
      50              55              60

His Asn Ala Lys Thr Lys Pro Cys Glu Glu Gln Tyr Gly Ser Thr Tyr
65              70              75              80

Arg Cys Val Ser Val Leu Thr Val Leu His Gln Asp Trp Leu Asn Gly
              85              90              95

Lys Glu Tyr Lys Cys Lys Val Ser Asn Lys Ala Leu Pro Ala Pro Ile
              100             105             110

Glu Lys Thr Ile Ser Lys Ala Lys Gly Gln Pro Arg Glu Pro Gln Val
              115             120             125

Tyr Thr Leu Pro Pro Ser Arg Glu Lys Met Thr Lys Asn Gln Val Ser
          130             135             140

Leu Thr Cys Leu Val Lys Gly Phe Tyr Pro Ser Asp Ile Ala Val Glu
145             150             155             160

Trp Glu Ser Asn Gly Gln Pro Glu Asn Asn Tyr Lys Thr Thr Pro Pro
              165             170             175
```

-continued

```
Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Gly Gly Gly Ser Gly Gly Gly Gly Ser His Leu Val Lys
225                 230                 235                 240

Cys Gly Glu Lys His Lys Ser Phe Cys Val Asn Gly Gly Glu Cys Phe
            245                 250                 255

Met Ile Glu Gly Pro Ser Asn Pro Ser Arg Tyr Leu Cys Lys Cys Pro
            260                 265                 270

Asn Glu Phe Thr Gly Asp Arg Cys Gln Glu Asp Phe Met Ala Ser Phe
            275                 280                 285

Asp Lys Thr His Thr Cys Pro Pro Cys Pro Ala Pro Glu Leu Leu Gly
            290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
            325                 330                 335

Glu Asp Pro Glu Val Lys Phe Asn Trp Tyr Val Asp Gly Val Glu Val
            340                 345                 350

His Asn Ala Lys Thr Lys Pro Cys Glu Glu Gln Tyr Gly Ser Thr Tyr
            355                 360                 365

Arg Cys Val Ser Val Leu Thr Val Leu His Gln Asp Trp Leu Asn Gly
            370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
            405                 410                 415

Tyr Thr Leu Pro Pro Ser Arg Glu Glu Met Thr Glu Asn Gln Val Ser
            420                 425                 430

Leu Thr Cys Leu Val Glu Gly Phe Tyr Pro Ser Asp Ile Ala Val Glu
            435                 440                 445

Trp Glu Ser Asn Gly Gln Pro Glu Asn Asn Tyr Glu Thr Thr Pro Pro
            450                 455                 460

Val Leu Asp Ser Asp Gly Ser Phe Phe Leu Tyr Ser Asp Leu Thr Val
465                 470                 475                 480

Asp Lys Ser Arg Trp Gln Gln Gly Asn Val Phe Ser Cys Ser Val Met
            485                 490                 495

His Glu Ala Leu His Asn His Tyr Thr Gln Lys Ser Leu Ser Leu Ser
            500                 505                 510

Pro Gly Lys
        515
```

<210> SEQ ID NO 74
<211> LENGTH: 515
<212> TYPE: PRT
<213> ORGANISM: Artificial Sequence
<220> FEATURE:
<223> OTHER INFORMATION: :huFcSEFL2(desK)v131(+):G4SG4:huNRG1(S177-F229)
        (NRGE1D)

<400> SEQUENCE: 74

Asp Lys Thr His Thr Cys Pro Pro Cys Pro Ala Pro Glu Leu Leu Gly

-continued

```
1                   5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
            50                  55                  60

His Asn Ala Lys Thr Lys Pro Cys Glu Glu Gln Tyr Gly Ser Thr Tyr
65                  70                  75                  80

Arg Cys Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Ser Arg Glu Lys Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser His Leu Val Lys
225                 230                 235                 240

Cys Gly Glu Ser His Lys Ser Phe Cys Val Asn Gly Gly Glu Cys Tyr
                245                 250                 255

Met Val Glu Gly Ser Ser Ile Pro Ser Arg Tyr Leu Cys Lys Cys Pro
                260                 265                 270

Asn Glu Phe Thr Gly Asp Arg Cys Gln Glu Asp Phe Met Ala Ser Phe
                275                 280                 285

Asp Lys Thr His Thr Cys Pro Pro Cys Pro Ala Pro Glu Leu Leu Gly
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
                340                 345                 350

His Asn Ala Lys Thr Lys Pro Cys Glu Glu Gln Tyr Gly Ser Thr Tyr
                355                 360                 365

Arg Cys Val Ser Val Leu Thr Val Leu His Gln Asp Trp Leu Asn Gly
            370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Glu Glu Met Thr Glu Asn Gln Val Ser
                420                 425                 430
```

```
Leu Thr Cys Leu Val Glu Gly Phe Tyr Pro Ser Asp Ile Ala Val Glu
        435                 440                 445

Trp Glu Ser Asn Gly Gln Pro Glu Asn Asn Tyr Glu Thr Thr Pro Pro
    450                 455                 460

Val Leu Asp Ser Asp Gly Ser Phe Phe Leu Tyr Ser Asp Leu Thr Val
465                 470                 475                 480

Asp Lys Ser Arg Trp Gln Gln Gly Asn Val Phe Ser Cys Ser Val Met
            485                 490                 495

His Glu Ala Leu His Asn His Tyr Thr Gln Lys Ser Leu Ser Leu Ser
        500                 505                 510

Pro Gly Lys
        515

<210> SEQ ID NO 75
<211> LENGTH: 523
<212> TYPE: PRT
<213> ORGANISM: Artificial Sequence
<220> FEATURE:
<223> OTHER INFORMATION: :huFcSEFL2(desK)v131(+):G4SG4:huNRG1(S177-Q237)
      (NRGE1C)

<400> SEQUENCE: 75

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Cys Glu Glu Gln Tyr Gly Ser Thr Tyr
65                  70                  75                  80

Arg Cys Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Lys Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser His Leu Val Lys
225                 230                 235                 240

Cys Gly Glu Lys His Lys Ser Phe Cys Val Asn Gly Gly Glu Cys Phe
            245                 250                 255

Met Ile Glu Gly Pro Ser Asn Pro Ser Arg Tyr Leu Cys Lys Cys Pro
```

-continued

```
              260              265              270

Asn Glu Phe Thr Gly Asp Arg Cys Gln Glu Asp Phe Met Ala Ser Phe
        275              280              285

Tyr Lys Ala Glu Glu Leu Tyr Gln Asp Lys Thr His Thr Cys Pro Pro
    290              295              300

Cys Pro Ala Pro Glu Leu Leu Gly Gly Pro Ser Val Phe Leu Phe Pro
305              310              315              320

Pro Lys Pro Lys Asp Thr Leu Met Ile Ser Arg Thr Pro Glu Val Thr
            325              330              335

Cys Val Val Val Asp Val Ser His Glu Asp Pro Glu Val Lys Phe Asn
        340              345              350

Trp Tyr Val Asp Gly Val Glu Val His Asn Ala Lys Thr Lys Pro Cys
        355              360              365

Glu Glu Gln Tyr Gly Ser Thr Tyr Arg Cys Val Ser Val Leu Thr Val
    370              375              380

Leu His Gln Asp Trp Leu Asn Gly Lys Glu Tyr Lys Cys Lys Val Ser
385              390              395              400

Asn Lys Ala Leu Pro Ala Pro Ile Glu Lys Thr Ile Ser Lys Ala Lys
            405              410              415

Gly Gln Pro Arg Glu Pro Gln Val Tyr Thr Leu Pro Pro Ser Arg Glu
            420              425              430

Glu Met Thr Glu Asn Gln Val Ser Leu Thr Cys Leu Val Glu Gly Phe
            435              440              445

Tyr Pro Ser Asp Ile Ala Val Glu Trp Glu Ser Asn Gly Gln Pro Glu
    450              455              460

Asn Asn Tyr Glu Thr Thr Pro Pro Val Leu Asp Ser Asp Gly Ser Phe
465              470              475              480

Phe Leu Tyr Ser Asp Leu Thr Val Asp Lys Ser Arg Trp Gln Gln Gly
            485              490              495

Asn Val Phe Ser Cys Ser Val Met His Glu Ala Leu His Asn His Tyr
            500              505              510

Thr Gln Lys Ser Leu Ser Leu Ser Pro Gly Lys
        515              520
```

```
<210> SEQ ID NO 76
<211> LENGTH: 523
<212> TYPE: PRT
<213> ORGANISM: Artificial Sequence
<220> FEATURE:
<223> OTHER INFORMATION: :huFcSEFL2(desK)v131(+):G4SG4:huNRG1(S177-Q237)
      (NRGE1D)

<400> SEQUENCE: 76

Asp Lys Thr His Thr Cys Pro Pro Cys Pro Ala Pro Glu Leu Leu Gly
1               5               10              15

Gly Pro Ser Val Phe Leu Phe Pro Pro Lys Pro Lys Asp Thr Leu Met
            20              25              30

Ile Ser Arg Thr Pro Glu Val Thr Cys Val Val Val Asp Val Ser His
        35              40              45

Glu Asp Pro Glu Val Lys Phe Asn Trp Tyr Val Asp Gly Val Glu Val
    50              55              60

His Asn Ala Lys Thr Lys Pro Cys Glu Glu Gln Tyr Gly Ser Thr Tyr
65              70              75              80

Arg Cys Val Ser Val Leu Thr Val Leu His Gln Asp Trp Leu Asn Gly
            85              90              95
```

-continued

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Lys Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Gly Gly Gly Ser Gly Gly Gly Gly Ser His Leu Val Lys
225                 230                 235                 240

Cys Gly Glu Ser His Lys Ser Phe Cys Val Asn Gly Gly Glu Cys Tyr
                245                 250                 255

Met Val Glu Gly Ser Ser Ile Pro Ser Arg Tyr Leu Cys Lys Cys Pro
            260                 265                 270

Asn Glu Phe Thr Gly Asp Arg Cys Gln Glu Asp Phe Met Ala Ser Phe
            275                 280                 285

Tyr Lys Ala Glu Glu Leu Tyr Gln Asp Lys Thr His Thr Cys Pro Pro
    290                 295                 300

Cys Pro Ala Pro Glu Leu Leu Gly Gly Pro Ser Val Phe Leu Phe Pro
305                 310                 315                 320

Pro Lys Pro Lys Asp Thr Leu Met Ile Ser Arg Thr Pro Glu Val Thr
            325                 330                 335

Cys Val Val Val Asp Val Ser His Glu Asp Pro Glu Val Lys Phe Asn
            340                 345                 350

Trp Tyr Val Asp Gly Val Glu Val His Asn Ala Lys Thr Lys Pro Cys
            355                 360                 365

Glu Glu Gln Tyr Gly Ser Thr Tyr Arg Cys Val Ser Val Leu Thr Val
    370                 375                 380

Leu His Gln Asp Trp Leu Asn Gly Lys Glu Tyr Lys Cys Lys Val Ser
385                 390                 395                 400

Asn Lys Ala Leu Pro Ala Pro Ile Glu Lys Thr Ile Ser Lys Ala Lys
            405                 410                 415

Gly Gln Pro Arg Glu Pro Gln Val Tyr Thr Leu Pro Pro Ser Arg Glu
            420                 425                 430

Glu Met Thr Glu Asn Gln Val Ser Leu Thr Cys Leu Val Glu Gly Phe
    435                 440                 445

Tyr Pro Ser Asp Ile Ala Val Glu Trp Glu Ser Asn Gly Gln Pro Glu
    450                 455                 460

Asn Asn Tyr Glu Thr Thr Pro Pro Val Leu Asp Ser Asp Gly Ser Phe
465                 470                 475                 480

Phe Leu Tyr Ser Asp Leu Thr Val Asp Lys Ser Arg Trp Gln Gln Gly
                485                 490                 495

Asn Val Phe Ser Cys Ser Val Met His Glu Ala Leu His Asn His Tyr
            500                 505                 510

Thr Gln Lys Ser Leu Ser Leu Ser Pro Gly Lys
```

-continued

```
          515                 520

<210> SEQ ID NO 77
<211> LENGTH: 521
<212> TYPE: PRT
<213> ORGANISM: Artificial Sequence
<220> FEATURE:
<223> OTHER INFORMATION: :huNRG1(S177-F229)(NRGE1C)
      ::2X(G4A)G4::huFcSEFL2v131(+)

<400> SEQUENCE: 77

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Gly Gly Gly Ala Gly Gly Gly Ala Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
            100                 105                 110

Val Ser His Glu Asp Pro Glu Val Lys Phe Asn Trp Tyr Val Asp Gly
        115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Lys Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Lys Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
            340                 345                 350
```

-continued

```
Val Asp Gly Val Glu Val His Asn Ala Lys Thr Lys Pro Cys Glu Glu
        355             360             365

Gln Tyr Gly Ser Thr Tyr Arg Cys Val Ser Val Leu Thr Val Leu His
        370             375             380

Gln Asp Trp Leu Asn Gly Lys Glu Tyr Lys Cys Lys Val Ser Asn Lys
385             390             395             400

Ala Leu Pro Ala Pro Ile Glu Lys Thr Ile Ser Lys Ala Lys Gly Gln
                405             410             415

Pro Arg Glu Pro Gln Val Tyr Thr Leu Pro Pro Ser Arg Glu Glu Met
                420             425             430

Thr Glu Asn Gln Val Ser Leu Thr Cys Leu Val Glu Gly Phe Tyr Pro
        435             440             445

Ser Asp Ile Ala Val Glu Trp Glu Ser Asn Gly Gln Pro Glu Asn Asn
        450             455             460

Tyr Glu Thr Thr Pro Pro Val Leu Asp Ser Asp Gly Ser Phe Phe Leu
465             470             475             480

Tyr Ser Asp Leu Thr Val Asp Lys Ser Arg Trp Gln Gln Gly Asn Val
                485             490             495

Phe Ser Cys Ser Val Met His Glu Ala Leu His Asn His Tyr Thr Gln
                500             505             510

Lys Ser Leu Ser Leu Ser Pro Gly Lys
        515             520
```

```
<210> SEQ ID NO 78
<211> LENGTH: 521
<212> TYPE: PRT
<213> ORGANISM: Artificial Sequence
<220> FEATURE:
<223> OTHER INFORMATION: :huNRG1(S177-F229)(NRGE1C)
      ::2X(G4E)G4::huFcSEFL2v131(+)

<400> SEQUENCE: 78
```

```
Ser His Leu Val Lys Cys Gly Glu Lys His Lys Ser Phe Cys Val Asn
1               5               10              15

Gly Gly Glu Cys Phe Met Ile Glu Gly Pro Ser Asn Pro Ser Arg Tyr
        20              25              30

Leu Cys Lys Cys Pro Asn Glu Phe Thr Gly Asp Arg Cys Gln Glu Asp
        35              40              45

Phe Met Ala Ser Phe Gly Gly Gly Gly Glu Gly Gly Gly Gly Glu Gly
        50              55              60

Gly Gly Gly Asp Lys Thr His Thr Cys Pro Pro Cys Pro Ala Pro Glu
65              70              75              80

Leu Leu Gly Gly Pro Ser Val Phe Leu Phe Pro Pro Lys Pro Lys Asp
                85              90              95

Thr Leu Met Ile Ser Arg Thr Pro Glu Val Thr Cys Val Val Val Asp
        100             105             110

Val Ser His Glu Asp Pro Glu Val Lys Phe Asn Trp Tyr Val Asp Gly
        115             120             125

Val Glu Val His Asn Ala Lys Thr Lys Pro Cys Glu Glu Gln Tyr Gly
        130             135             140

Ser Thr Tyr Arg Cys Val Ser Val Leu Thr Val Leu His Gln Asp Trp
145             150             155             160

Leu Asn Gly Lys Glu Tyr Lys Cys Lys Val Ser Asn Lys Ala Leu Pro
                165             170             175

Ala Pro Ile Glu Lys Thr Ile Ser Lys Ala Lys Gly Gln Pro Arg Glu
                180             185             190
```

```
Pro Gln Val Tyr Thr Leu Pro Pro Ser Arg Glu Lys Met Thr Lys Asn
        195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Lys Ser Asp Gly Ser Phe Phe Leu Tyr Ser Lys
                245                 250                 255

Leu Thr Val Asp Lys Ser Arg Trp Gln Gln Gly Asn Val Phe Ser Cys
                260                 265                 270

Ser Val Met His Glu Ala Leu His Asn His Tyr Thr Gln Lys Ser Leu
        275                 280                 285

Ser Leu Ser Pro Gly Lys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Cys Glu Glu
        355                 360                 365

Gln Tyr Gly Ser Thr Tyr Arg Cys Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Glu Asn Gln Val Ser Leu Thr Cys Leu Val Glu Gly Phe Tyr Pro
        435                 440                 445

Ser Asp Ile Ala Val Glu Trp Glu Ser Asn Gly Gln Pro Glu Asn Asn
    450                 455                 460

Tyr Glu Thr Thr Pro Pro Val Leu Asp Ser Asp Gly Ser Phe Phe Leu
465                 470                 475                 480

Tyr Ser Asp Leu Thr Val Asp Lys Ser Arg Trp Gln Gln Gly Asn Val
                485                 490                 495

Phe Ser Cys Ser Val Met His Glu Ala Leu His Asn His Tyr Thr Gln
        500                 505                 510

Lys Ser Leu Ser Leu Ser Pro Gly Lys
        515                 520
```

<210> SEQ ID NO 79
<211> LENGTH: 521
<212> TYPE: PRT
<213> ORGANISM: Artificial Sequence
<220> FEATURE:
<223> OTHER INFORMATION: :huNRG1(S177-F229)(NRGE1D)
      ::2X(G4A)G4::huFcSEFL2v131(+)

<400> SEQUENCE: 79

```
Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
```

```
                    20              25              30

Leu Cys Lys Cys Pro Asn Glu Phe Thr Gly Asp Arg Cys Gln Glu Asp
        35              40              45

Phe Met Ala Ser Phe Gly Gly Gly Ala Gly Gly Gly Ala Gly
    50              55              60

Gly Gly Gly Asp Lys Thr His Thr Cys Pro Pro Cys Pro Ala Pro Glu
65              70              75              80

Leu Leu Gly Gly Pro Ser Val Phe Leu Phe Pro Pro Lys Pro Lys Asp
                85              90              95

Thr Leu Met Ile Ser Arg Thr Pro Glu Val Thr Cys Val Val Val Asp
                100             105             110

Val Ser His Glu Asp Pro Glu Val Lys Phe Asn Trp Tyr Val Asp Gly
        115             120             125

Val Glu Val His Asn Ala Lys Thr Lys Pro Cys Glu Glu Gln Tyr Gly
        130             135             140

Ser Thr Tyr Arg Cys Val Ser Val Leu Thr Val Leu His Gln Asp Trp
145             150             155             160

Leu Asn Gly Lys Glu Tyr Lys Cys Lys Val Ser Asn Lys Ala Leu Pro
                165             170             175

Ala Pro Ile Glu Lys Thr Ile Ser Lys Ala Lys Gly Gln Pro Arg Glu
                180             185             190

Pro Gln Val Tyr Thr Leu Pro Pro Ser Arg Glu Lys Met Thr Lys Asn
        195             200             205

Gln Val Ser Leu Thr Cys Leu Val Lys Gly Phe Tyr Pro Ser Asp Ile
        210             215             220

Ala Val Glu Trp Glu Ser Asn Gly Gln Pro Glu Asn Asn Tyr Lys Thr
225             230             235             240

Thr Pro Pro Val Leu Lys Ser Asp Gly Ser Phe Phe Leu Tyr Ser Lys
                245             250             255

Leu Thr Val Asp Lys Ser Arg Trp Gln Gln Gly Asn Val Phe Ser Cys
                260             265             270

Ser Val Met His Glu Ala Leu His Asn His Tyr Thr Gln Lys Ser Leu
        275             280             285

Ser Leu Ser Pro Gly Lys Asp Lys Thr His Thr Cys Pro Pro Cys Pro
        290             295             300

Ala Pro Glu Leu Leu Gly Gly Pro Ser Val Phe Leu Phe Pro Pro Lys
305             310             315             320

Pro Lys Asp Thr Leu Met Ile Ser Arg Thr Pro Glu Val Thr Cys Val
                325             330             335

Val Val Asp Val Ser His Glu Asp Pro Glu Val Lys Phe Asn Trp Tyr
                340             345             350

Val Asp Gly Val Glu Val His Asn Ala Lys Thr Lys Pro Cys Glu Glu
                355             360             365

Gln Tyr Gly Ser Thr Tyr Arg Cys Val Ser Val Leu Thr Val Leu His
        370             375             380

Gln Asp Trp Leu Asn Gly Lys Glu Tyr Lys Cys Lys Val Ser Asn Lys
385             390             395             400

Ala Leu Pro Ala Pro Ile Glu Lys Thr Ile Ser Lys Ala Lys Gly Gln
                405             410             415

Pro Arg Glu Pro Gln Val Tyr Thr Leu Pro Pro Ser Arg Glu Glu Met
                420             425             430

Thr Glu Asn Gln Val Ser Leu Thr Cys Leu Val Glu Gly Phe Tyr Pro
        435             440             445
```

-continued

```
Ser Asp Ile Ala Val Glu Trp Glu Ser Asn Gly Gln Pro Glu Asn Asn
    450             455         460

Tyr Glu Thr Thr Pro Pro Val Leu Asp Ser Asp Gly Ser Phe Phe Leu
465             470             475                 480

Tyr Ser Asp Leu Thr Val Asp Lys Ser Arg Trp Gln Gln Gly Asn Val
            485             490                 495

Phe Ser Cys Ser Val Met His Glu Ala Leu His Asn His Tyr Thr Gln
            500             505                 510

Lys Ser Leu Ser Leu Ser Pro Gly Lys
        515             520

<210> SEQ ID NO 80
<211> LENGTH: 521
<212> TYPE: PRT
<213> ORGANISM: Artificial Sequence
<220> FEATURE:
<223> OTHER INFORMATION: :huNRG1(S177-F229)(NRGE1D)
      ::2X(G4E)G4::huFcSEFL2v131(+)

<400> SEQUENCE: 80

Ser His Leu Val Lys Cys Gly Glu Ser His Lys Ser Phe Cys Val Asn
1               5               10              15

Gly Gly Glu Cys Tyr Met Val Glu Gly Ser Ser Ile Pro Ser Arg Tyr
            20              25              30

Leu Cys Lys Cys Pro Asn Glu Phe Thr Gly Asp Arg Cys Gln Glu Asp
        35              40                  45

Phe Met Ala Ser Phe Gly Gly Gly Gly Glu Gly Gly Gly Gly Glu Gly
    50              55                  60

Gly Gly Gly Asp Lys Thr His Thr Cys Pro Pro Cys Pro Ala Pro Glu
65              70              75                  80

Leu Leu Gly Gly Pro Ser Val Phe Leu Phe Pro Pro Lys Pro Lys Asp
            85              90              95

Thr Leu Met Ile Ser Arg Thr Pro Glu Val Thr Cys Val Val Val Asp
            100             105             110

Val Ser His Glu Asp Pro Glu Val Lys Phe Asn Trp Tyr Val Asp Gly
            115             120             125

Val Glu Val His Asn Ala Lys Thr Lys Pro Cys Glu Glu Gln Tyr Gly
    130             135             140

Ser Thr Tyr Arg Cys Val Ser Val Leu Thr Val Leu His Gln Asp Trp
145             150             155                 160

Leu Asn Gly Lys Glu Tyr Lys Cys Lys Val Ser Asn Lys Ala Leu Pro
            165             170             175

Ala Pro Ile Glu Lys Thr Ile Ser Lys Ala Lys Gly Gln Pro Arg Glu
            180             185             190

Pro Gln Val Tyr Thr Leu Pro Pro Ser Arg Glu Lys Met Thr Lys Asn
            195             200             205

Gln Val Ser Leu Thr Cys Leu Val Lys Gly Phe Tyr Pro Ser Asp Ile
    210             215             220

Ala Val Glu Trp Glu Ser Asn Gly Gln Pro Glu Asn Asn Tyr Lys Thr
225             230             235                 240

Thr Pro Pro Val Leu Lys Ser Asp Gly Ser Phe Phe Leu Tyr Ser Lys
            245             250             255

Leu Thr Val Asp Lys Ser Arg Trp Gln Gln Gly Asn Val Phe Ser Cys
            260             265             270

Ser Val Met His Glu Ala Leu His Asn His Tyr Thr Gln Lys Ser Leu
```

-continued

```
            275                 280                 285
Ser Leu Ser Pro Gly Lys Asp Lys Thr His Thr Cys Pro Pro Cys Pro
    290                 295                 300

Ala Pro Glu Leu Leu Gly Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Lys Phe Asn Trp Tyr
                340                 345                 350

Val Asp Gly Val Glu Val His Asn Ala Lys Thr Lys Pro Cys Glu Glu
            355                 360                 365

Gln Tyr Gly Ser Thr Tyr Arg Cys Val Ser Val Leu Thr Val Leu His
    370                 375                 380

Gln Asp Trp Leu Asn Gly Lys Glu Tyr Lys Cys Lys Val Ser Asn Lys
385                 390                 395                 400

Ala Leu Pro Ala Pro Ile Glu Lys Thr Ile Ser Lys Ala Lys Gly Gln
                405                 410                 415

Pro Arg Glu Pro Gln Val Tyr Thr Leu Pro Pro Ser Arg Glu Glu Met
                420                 425                 430

Thr Glu Asn Gln Val Ser Leu Thr Cys Leu Val Glu Gly Phe Tyr Pro
            435                 440                 445

Ser Asp Ile Ala Val Glu Trp Glu Ser Asn Gly Gln Pro Glu Asn Asn
    450                 455                 460

Tyr Glu Thr Thr Pro Pro Val Leu Asp Ser Asp Gly Ser Phe Phe Leu
465                 470                 475                 480

Tyr Ser Asp Leu Thr Val Asp Lys Ser Arg Trp Gln Gln Gly Asn Val
                485                 490                 495

Phe Ser Cys Ser Val Met His Glu Ala Leu His Asn His Tyr Thr Gln
            500                 505                 510

Lys Ser Leu Ser Leu Ser Pro Gly Lys
        515                 520
```

<210> SEQ ID NO 81
<211> LENGTH: 294
<212> TYPE: PRT
<213> ORGANISM: Artificial Sequence
<220> FEATURE:
<223> OTHER INFORMATION: huNRG1(S177-S228)(wt)((G4E)2:G4)::huFcSEFL2
    (Pb)

<400> SEQUENCE: 81

```
Ser His Leu Val Lys Cys Ala Glu Lys Glu Lys Thr Phe Cys Val Asn
1                   5                   10                  15

Gly Gly Glu Cys Phe Met Val Lys Asp Leu Ser Asn Pro Ser Arg Tyr
                20                  25                  30

Leu Cys Lys Cys Pro Asn Glu Phe Thr Gly Asp Arg Cys Gln Asn Tyr
            35                  40                  45

Val Met Ala Ser Phe Gly Gly Gly Glu Gly Gly Gly Glu Gly
    50                  55                  60

Gly Gly Gly Asp Lys Thr His Thr Cys Pro Pro Cys Pro Ala Pro Glu
65                  70                  75                  80

Leu Leu Gly Gly Pro Ser Val Phe Leu Phe Pro Pro Lys Pro Lys Asp
                85                  90                  95

Thr Leu Met Ile Ser Arg Thr Pro Glu Val Thr Cys Val Val Val Asp
                100                 105                 110
```

-continued

```
Val Ser His Glu Asp Pro Glu Val Lys Phe Asn Trp Tyr Val Asp Gly
    115                 120                 125

Val Glu Val His Asn Ala Lys Thr Lys Pro Cys Glu Glu Gln Tyr Gly
    130                 135                 140

Ser Thr Tyr Arg Cys Val Ser Val Leu Thr Val Leu His Gln Asp Trp
145                 150                 155                 160

Leu Asn Gly Lys Glu Tyr Lys Cys Lys Val Ser Asn Lys Ala Leu Pro
                165                 170                 175

Ala Pro Ile Glu Lys Thr Ile Ser Lys Ala Lys Gly Gln Pro Arg Glu
            180                 185                 190

Pro Gln Val Tyr Thr Leu Pro Pro Ser Arg Glu Glu Met Thr Lys Asn
            195                 200                 205

Gln Val Ser Leu Thr Cys Leu Val Lys Gly Phe Tyr Pro Ser Asp Ile
    210                 215                 220

Ala Val Glu Trp Glu Ser Asn Gly Gln Pro Glu Asn Asn Tyr Lys Thr
225                 230                 235                 240

Thr Pro Pro Val Leu Asp Ser Asp Gly Ser Phe Phe Leu Tyr Ser Lys
                245                 250                 255

Leu Thr Val Asp Lys Ser Arg Trp Gln Gln Gly Asn Val Phe Ser Cys
            260                 265                 270

Ser Val Met His Glu Ala Leu His Asn His Tyr Thr Gln Lys Ser Leu
        275                 280                 285

Ser Leu Ser Pro Gly Lys
    290
```

```
<210> SEQ ID NO 82
<211> LENGTH: 290
<212> TYPE: PRT
<213> ORGANISM: Artificial Sequence
<220> FEATURE:
<223> OTHER INFORMATION: huNRG1(S177-Q237)(1A1)::GG::huFcSEFL2 (Pb)

<400> SEQUENCE: 82

Ser His Leu Val Lys Cys Gly Glu Ser Glu Lys Ser Phe Cys Val Asn
1               5                   10                  15

Gly Gly Glu Cys Tyr Val Ile Glu Asp Ser Ser Ile Pro Ser Arg Phe
            20                  25                  30

Leu Cys Lys Cys Pro Asn Glu Phe Thr Gly Asp Arg Cys Gln Asn Val
        35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175
```

-continued

```
Lys Thr Ile Ser Lys Ala Lys Gly Gln Pro Arg Glu Pro Gln Val Tyr
            180             185             190

Thr Leu Pro Pro Ser Arg Glu Glu Met Thr Lys Asn Gln Val Ser Leu
            195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235             240

Leu Asp Ser Asp Gly Ser Phe Phe Leu Tyr Ser Lys Leu Thr Val Asp
            245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
    275             280             285

Gly Lys
    290
```

```
<210> SEQ ID NO 83
<211> LENGTH: 290
<212> TYPE: PRT
<213> ORGANISM: Artificial Sequence
<220> FEATURE:
<223> OTHER INFORMATION: huNRG1(S177-Q237)(1A12)::GG::huFcSEFL2 (Pb)

<400> SEQUENCE: 83
```

```
Ser His Leu Val Lys Cys Ala Glu Lys His Lys Ser Phe Cys Val Asn
1               5               10              15

Gly Gly Glu Cys Tyr Val Val Glu Arg Pro Ser Ile Pro Ser Arg Tyr
            20              25              30

Leu Cys Lys Cys Pro Asn Glu Phe Thr Gly Asp Arg Cys Gln Lys Phe
            35              40              45

Phe Met Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
            85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
            115             120             125

Asn Ala Lys Thr Lys Pro Cys Glu Glu Gln Tyr Gly Ser Thr Tyr Arg
    130             135             140

Cys Val Ser Val Leu Thr Val Leu His Gln Asp Trp Leu Asn Gly Lys
145             150             155             160

Glu Tyr Lys Cys Lys Val Ser Asn Lys Ala Leu Pro Ala Pro Ile Glu
            165             170             175

Lys Thr Ile Ser Lys Ala Lys Gly Gln Pro Arg Glu Pro Gln Val Tyr
            180             185             190

Thr Leu Pro Pro Ser Arg Glu Glu Met Thr Lys Asn Gln Val Ser Leu
            195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235             240
```

-continued

```
Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
                275                 280                 285

Gly Lys
    290

<210> SEQ ID NO 84
<211> LENGTH: 290
<212> TYPE: PRT
<213> ORGANISM: Artificial Sequence
<220> FEATURE:
<223> OTHER INFORMATION: huNRG1(S177-Q237)(1B4)::GG::huFcSEFL2 (Pb)

<400> SEQUENCE: 84

Ser His Leu Val Lys Cys Ala Glu Arg Asp Lys Ser Phe Cys Val Asn
1               5                   10                  15

Gly Gly Glu Cys Tyr Val Ile Glu His Leu Ser Asn Pro Ser Arg Phe
                20                  25                  30

Leu Cys Lys Cys Pro Asn Glu Phe Thr Gly Asp Arg Cys Gln Lys Asp
                35                  40                  45

Phe Met Ala Ser Phe Tyr Lys Ala Glu Glu Leu Tyr Gln Gly Gly Asp
        50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
                115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
                195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
                275                 280                 285

Gly Lys
    290
```

-continued

<210> SEQ ID NO 85
<211> LENGTH: 290
<212> TYPE: PRT
<213> ORGANISM: Artificial Sequence
<220> FEATURE:
<223> OTHER INFORMATION: huNRG1(S177-Q237)(1B4)::GG::huFcSEFL2 (Pb)

<400> SEQUENCE: 85

```
Ser His Leu Val Lys Cys Gly Glu Arg Asp Lys Thr Phe Cys Val Asn
1               5                   10                  15

Gly Gly Glu Cys Phe Met Ile Glu Asp Ser Ser Asn Pro Ser Arg Tyr
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
        275                 280                 285

Gly Lys
    290
```

<210> SEQ ID NO 86
<211> LENGTH: 290
<212> TYPE: PRT
<213> ORGANISM: Artificial Sequence
<220> FEATURE:
<223> OTHER INFORMATION: huNRG1(S177-Q237)(1B9)::GG::huFcSEFL2 (Pb)

<400> SEQUENCE: 86

```
Ser His Leu Val Lys Cys Ala Glu Lys His Lys Ser Phe Cys Val Asn
1               5                   10                  15
```

```
Gly Gly Glu Cys Phe Met Val Glu Asp Leu Ser Ile Pro Ser Arg Tyr
          20                  25                  30

Leu Cys Lys Cys Pro Asn Glu Phe Thr Gly Asp Arg Cys Gln Asp Val
          35                  40                  45

Phe Met Ala Ser Phe Tyr Lys Ala Glu Glu Leu Tyr Gln Gly Gly Asp
      50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
              85                  90                  95

Ser Arg Thr Pro Glu Val Thr Cys Val Val Val Asp Val Ser His Glu
          100                 105                 110

Asp Pro Glu Val Lys Phe Asn Trp Tyr Val Asp Gly Val Glu Val His
          115                 120                 125

Asn Ala Lys Thr Lys Pro Cys Glu Glu Gln Tyr Gly Ser Thr Tyr Arg
      130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
              165                 170                 175

Lys Thr Ile Ser Lys Ala Lys Gly Gln Pro Arg Glu Pro Gln Val Tyr
              180                 185                 190

Thr Leu Pro Pro Ser Arg Glu Glu Met Thr Lys Asn Gln Val Ser Leu
          195                 200                 205

Thr Cys Leu Val Lys Gly Phe Tyr Pro Ser Asp Ile Ala Val Glu Trp
      210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
              245                 250                 255

Lys Ser Arg Trp Gln Gln Gly Asn Val Phe Ser Cys Ser Val Met His
              260                 265                 270

Glu Ala Leu His Asn His Tyr Thr Gln Lys Ser Leu Ser Leu Ser Pro
          275                 280                 285

Gly Lys
    290
```

```
<210> SEQ ID NO 87
<211> LENGTH: 290
<212> TYPE: PRT
<213> ORGANISM: Artificial Sequence
<220> FEATURE:
<223> OTHER INFORMATION: huNRG1(S177-Q237)(1C11)::GG::huFcSEFL2 (Pb)

<400> SEQUENCE: 87
```

```
Ser His Leu Val Lys Cys Gly Glu Lys Glu Lys Thr Phe Cys Val Asn
1               5                   10                  15

Gly Gly Glu Cys Tyr Met Val Glu Arg Pro Ser Ile Pro Ser Arg Phe
          20                  25                  30

Leu Cys Lys Cys Pro Asn Glu Phe Thr Gly Asp Arg Cys Gln Lys Phe
          35                  40                  45

Phe Met Ala Ser Phe Tyr Lys Ala Glu Glu Leu Tyr Gln Gly Gly Asp
      50                  55                  60

Lys Thr His Thr Cys Pro Pro Cys Pro Ala Pro Glu Leu Leu Gly Gly
65                  70                  75                  80
```

-continued

```
Pro Ser Val Phe Leu Phe Pro Pro Lys Pro Lys Asp Thr Leu Met Ile
            85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
            115             120             125

Asn Ala Lys Thr Lys Pro Cys Glu Glu Gln Tyr Gly Ser Thr Tyr Arg
    130             135             140

Cys Val Ser Val Leu Thr Val Leu His Gln Asp Trp Leu Asn Gly Lys
145             150             155             160

Glu Tyr Lys Cys Lys Val Ser Asn Lys Ala Leu Pro Ala Pro Ile Glu
            165             170             175

Lys Thr Ile Ser Lys Ala Lys Gly Gln Pro Arg Glu Pro Gln Val Tyr
            180             185             190

Thr Leu Pro Pro Ser Arg Glu Glu Met Thr Lys Asn Gln Val Ser Leu
            195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235             240

Leu Asp Ser Asp Gly Ser Phe Phe Leu Tyr Ser Lys Leu Thr Val Asp
            245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
            275             280             285

Gly Lys
    290
```

<210> SEQ ID NO 88
<211> LENGTH: 290
<212> TYPE: PRT
<213> ORGANISM: Artificial Sequence
<220> FEATURE:
<223> OTHER INFORMATION: huNRG1(S177-Q237)(1D10)::GG::huFcSEFL2 (Pb)

<400> SEQUENCE: 88

```
Ser His Leu Val Lys Cys Ala Glu Arg Asp Lys Thr Phe Cys Val Asn
1               5               10              15

Gly Gly Glu Cys Tyr Met Ile Glu Asp Leu Ser Ile Pro Ser Arg Tyr
            20              25              30

Leu Cys Lys Cys Pro Asn Glu Phe Thr Gly Asp Arg Cys Gln Lys Asp
            35              40              45

Phe Met Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
            85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
            115             120             125

Asn Ala Lys Thr Lys Pro Cys Glu Glu Gln Tyr Gly Ser Thr Tyr Arg
    130             135             140
```

```
Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290

<210> SEQ ID NO 89
<211> LENGTH: 290
<212> TYPE: PRT
<213> ORGANISM: Artificial Sequence
<220> FEATURE:
<223> OTHER INFORMATION: huNRG1(S177-Q237)(1D4)::GG::huFcSEFL2 (Pb)

<400> SEQUENCE: 89

Ser His Leu Val Lys Cys Gly Glu Arg Asp Lys Thr Phe Cys Val Asn
1               5                   10                  15

Gly Gly Glu Cys Tyr Val Val Glu His Ser Ser Asn Pro Ser Arg Tyr
                20                  25                  30

Leu Cys Lys Cys Pro Asn Glu Phe Thr Gly Asp Arg Cys Gln Lys Phe
            35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205
```

-continued

```
Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290
```

```
<210> SEQ ID NO 90
<211> LENGTH: 290
<212> TYPE: PRT
<213> ORGANISM: Artificial Sequence
<220> FEATURE:
<223> OTHER INFORMATION: huNRG1(S177-Q237)(2E3)::GG::huFcSEFL2 (Pb)

<400> SEQUENCE: 90
```

```
Ser His Leu Val Lys Cys Gly Glu Lys Glu Lys Ser Phe Cys Val Asn
1                   5                   10                  15

Gly Gly Glu Cys Tyr Met Ile Glu Gly Leu Ser Ile Pro Ser Arg Phe
                20                  25                  30

Leu Cys Lys Cys Pro Asn Glu Phe Thr Gly Asp Arg Cys Gln Asp Val
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
                100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270
```

```
Glu Ala Leu His Asn His Tyr Thr Gln Lys Ser Leu Ser Leu Ser Pro
        275                 280                 285

Gly Lys
    290

<210> SEQ ID NO 91
<211> LENGTH: 290
<212> TYPE: PRT
<213> ORGANISM: Artificial Sequence
<220> FEATURE:
<223> OTHER INFORMATION: huNRG1(S177-Q237)(2E4)::GG::huFcSEFL2 (Pb)

<400> SEQUENCE: 91

Ser His Leu Val Lys Cys Gly Glu Ser Asp Lys Ser Phe Cys Val Asn
1                 5                 10                  15

Gly Gly Glu Cys Phe Met Val Lys Arg Pro Ser Asn Pro Ser Arg Tyr
            20                  25                  30

Leu Cys Lys Cys Pro Asn Glu Phe Thr Gly Asp Arg Cys Gln Lys Val
        35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 92
<211> LENGTH: 290
<212> TYPE: PRT
<213> ORGANISM: Artificial Sequence
```

```
<220> FEATURE:
<223> OTHER INFORMATION: huNRG1(S177-Q237)(2F2)::GG::huFcSEFL2 (Pb)

<400> SEQUENCE: 92

Ser His Leu Val Lys Cys Ala Glu Ser Glu Lys Thr Phe Cys Val Asn
1               5                   10                  15

Gly Gly Glu Cys Tyr Met Ile Glu His Pro Ser Asn Pro Ser Arg Phe
            20                  25                  30

Leu Cys Lys Cys Pro Asn Glu Phe Thr Gly Asp Arg Cys Gln Asn Val
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290

<210> SEQ ID NO 93
<211> LENGTH: 290
<212> TYPE: PRT
<213> ORGANISM: Artificial Sequence
<220> FEATURE:
<223> OTHER INFORMATION: huNRG1(S177-Q237)(2G3)::GG::huFcSEFL2 (Pb)

<400> SEQUENCE: 93

Ser His Leu Val Lys Cys Gly Glu Arg Gln Lys Ser Phe Cys Val Asn
1               5                   10                  15

Gly Gly Glu Cys Tyr Met Val Glu Asp Leu Ser Ile Pro Ser Arg Tyr
            20                  25                  30

Leu Cys Lys Cys Pro Asn Glu Phe Thr Gly Asp Arg Cys Gln Lys Val
```

-continued

```
          35                    40                    45
Phe Met Ala Ser Phe Tyr Lys Ala Glu Glu Leu Tyr Gln Gly Gly Asp
    50                    55                    60
Lys Thr His Thr Cys Pro Pro Cys Pro Ala Pro Glu Leu Leu Gly Gly
65                    70                    75                    80
Pro Ser Val Phe Leu Phe Pro Pro Lys Pro Lys Asp Thr Leu Met Ile
                  85                    90                    95
Ser Arg Thr Pro Glu Val Thr Cys Val Val Val Asp Val Ser His Glu
                  100                   105                   110
Asp Pro Glu Val Lys Phe Asn Trp Tyr Val Asp Gly Val Glu Val His
                  115                   120                   125
Asn Ala Lys Thr Lys Pro Cys Glu Glu Gln Tyr Gly Ser Thr Tyr Arg
    130                   135                   140
Cys Val Ser Val Leu Thr Val Leu His Gln Asp Trp Leu Asn Gly Lys
145                   150                   155                   160
Glu Tyr Lys Cys Lys Val Ser Asn Lys Ala Leu Pro Ala Pro Ile Glu
                  165                   170                   175
Lys Thr Ile Ser Lys Ala Lys Gly Gln Pro Arg Glu Pro Gln Val Tyr
                  180                   185                   190
Thr Leu Pro Pro Ser Arg Glu Glu Met Thr Lys Asn Gln Val Ser Leu
                  195                   200                   205
Thr Cys Leu Val Lys Gly Phe Tyr Pro Ser Asp Ile Ala Val Glu Trp
    210                   215                   220
Glu Ser Asn Gly Gln Pro Glu Asn Asn Tyr Lys Thr Thr Pro Pro Val
225                   230                   235                   240
Leu Asp Ser Asp Gly Ser Phe Phe Leu Tyr Ser Lys Leu Thr Val Asp
                  245                   250                   255
Lys Ser Arg Trp Gln Gln Gly Asn Val Phe Ser Cys Ser Val Met His
                  260                   265                   270
Glu Ala Leu His Asn His Tyr Thr Gln Lys Ser Leu Ser Leu Ser Pro
    275                   280                   285
Gly Lys
    290
```

```
<210> SEQ ID NO 94
<211> LENGTH: 290
<212> TYPE: PRT
<213> ORGANISM: Artificial Sequence
<220> FEATURE:
<223> OTHER INFORMATION: huNRG1(S177-Q237)(2G4)::GG::huFcSEFL2 (Pb)

<400> SEQUENCE: 94
```

```
Ser His Leu Val Lys Cys Ala Glu Asn Glu Lys Thr Phe Cys Val Asn
1                 5                     10                    15
Gly Gly Glu Cys Phe Val Val Glu Gly Leu Ser Ile Pro Ser Arg Tyr
                  20                    25                    30
Leu Cys Lys Cys Pro Asn Glu Phe Thr Gly Asp Arg Cys Gln Asp Val
          35                    40                    45
Phe Met Ala Ser Phe Tyr Lys Ala Glu Glu Leu Tyr Gln Gly Gly Asp
    50                    55                    60
Lys Thr His Thr Cys Pro Pro Cys Pro Ala Pro Glu Leu Leu Gly Gly
65                    70                    75                    80
Pro Ser Val Phe Leu Phe Pro Pro Lys Pro Lys Asp Thr Leu Met Ile
                  85                    90                    95
Ser Arg Thr Pro Glu Val Thr Cys Val Val Val Asp Val Ser His Glu
```

-continued

```
                100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
        275                 280                 285

Gly Lys
    290
```

```
<210> SEQ ID NO 95
<211> LENGTH: 290
<212> TYPE: PRT
<213> ORGANISM: Artificial Sequence
<220> FEATURE:
<223> OTHER INFORMATION: huNRG1(S177-Q237)(2H7)::GG::huFcSEFL2 (Pb)

<400> SEQUENCE: 95

Ser His Leu Val Lys Cys Gly Glu Lys Glu Lys Ser Phe Cys Val Asn
1               5                   10                  15

Gly Gly Glu Cys Tyr Val Val Glu Asp Leu Ser Ile Pro Ser Arg Phe
            20                  25                  30

Leu Cys Lys Cys Pro Asn Glu Phe Thr Gly Asp Arg Cys Gln Lys Val
        35                  40                  45

Val Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
```

-continued

```
                    165                  170                  175
Lys Thr Ile Ser Lys Ala Lys Gly Gln Pro Arg Glu Pro Gln Val Tyr
                180                  185                  190
Thr Leu Pro Pro Ser Arg Glu Glu Met Thr Lys Asn Gln Val Ser Leu
                195                  200                  205
Thr Cys Leu Val Lys Gly Phe Tyr Pro Ser Asp Ile Ala Val Glu Trp
        210                  215                  220
Glu Ser Asn Gly Gln Pro Glu Asn Asn Tyr Lys Thr Thr Pro Pro Val
225                  230                  235                  240
Leu Asp Ser Asp Gly Ser Phe Phe Leu Tyr Ser Lys Leu Thr Val Asp
                245                  250                  255
Lys Ser Arg Trp Gln Gln Gly Asn Val Phe Ser Cys Ser Val Met His
                260                  265                  270
Glu Ala Leu His Asn His Tyr Thr Gln Lys Ser Leu Ser Leu Ser Pro
        275                  280                  285
Gly Lys
    290

<210> SEQ ID NO 96
<211> LENGTH: 290
<212> TYPE: PRT
<213> ORGANISM: Artificial Sequence
<220> FEATURE:
<223> OTHER INFORMATION: huNRG1(S177-Q237)(3A7)::GG::huFcSEFL2 (Pb)

<400> SEQUENCE: 96

Ser His Leu Val Lys Cys Ala Glu Lys Glu Lys Ser Phe Cys Val Asn
1                   5                   10                  15
Gly Gly Glu Cys Phe Val Ile Glu Gly Ser Ser Ile Pro Ser Arg Phe
                20                  25                  30
Leu Cys Lys Cys Pro Asn Glu Phe Thr Gly Asp Arg Cys Gln Lys Val
            35                  40                  45
Val Met Ala Ser Phe Tyr Lys Ala Glu Glu Leu Tyr Gln Gly Gly Asp
        50                  55                  60
Lys Thr His Thr Cys Pro Pro Cys Pro Ala Pro Glu Leu Leu Gly Gly
65                  70                  75                  80
Pro Ser Val Phe Leu Phe Pro Pro Lys Pro Lys Asp Thr Leu Met Ile
                85                  90                  95
Ser Arg Thr Pro Glu Val Thr Cys Val Val Val Asp Val Ser His Glu
                100                 105                 110
Asp Pro Glu Val Lys Phe Asn Trp Tyr Val Asp Gly Val Glu Val His
        115                 120                 125
Asn Ala Lys Thr Lys Pro Cys Glu Glu Gln Tyr Gly Ser Thr Tyr Arg
        130                 135                 140
Cys Val Ser Val Leu Thr Val Leu His Gln Asp Trp Leu Asn Gly Lys
145                 150                 155                 160
Glu Tyr Lys Cys Lys Val Ser Asn Lys Ala Leu Pro Ala Pro Ile Glu
                165                 170                 175
Lys Thr Ile Ser Lys Ala Lys Gly Gln Pro Arg Glu Pro Gln Val Tyr
                180                 185                 190
Thr Leu Pro Pro Ser Arg Glu Glu Met Thr Lys Asn Gln Val Ser Leu
                195                 200                 205
Thr Cys Leu Val Lys Gly Phe Tyr Pro Ser Asp Ile Ala Val Glu Trp
        210                 215                 220
Glu Ser Asn Gly Gln Pro Glu Asn Asn Tyr Lys Thr Thr Pro Pro Val
```

```
225             230             235             240

Leu Asp Ser Asp Gly Ser Phe Phe Leu Tyr Ser Lys Leu Thr Val Asp
                245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
        275             280             285

Gly Lys
    290

<210> SEQ ID NO 97
<211> LENGTH: 290
<212> TYPE: PRT
<213> ORGANISM: Artificial Sequence
<220> FEATURE:
<223> OTHER INFORMATION: huNRG1(S177-Q237)(3B8)::GG::huFcSEFL2 (Pb)

<400> SEQUENCE: 97

Ser His Leu Val Lys Cys Gly Glu Arg Asp Lys Ser Phe Cys Val Asn
1               5               10              15

Gly Gly Glu Cys Phe Met Val Glu Arg Ser Ser Ile Pro Ser Arg Tyr
            20              25              30

Leu Cys Lys Cys Pro Asn Glu Phe Thr Gly Asp Arg Cys Gln Asp Phe
        35              40              45

Phe Leu Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
            85              90              95

Ser Arg Thr Pro Glu Val Thr Cys Val Val Val Asp Val Ser His Glu
            100             105             110

Asp Pro Glu Val Lys Phe Asn Trp Tyr Val Asp Gly Val Glu Val His
        115             120             125

Asn Ala Lys Thr Lys Pro Cys Glu Glu Gln Tyr Gly Ser Thr Tyr Arg
    130             135             140

Cys Val Ser Val Leu Thr Val Leu His Gln Asp Trp Leu Asn Gly Lys
145             150             155             160

Glu Tyr Lys Cys Lys Val Ser Asn Lys Ala Leu Pro Ala Pro Ile Glu
            165             170             175

Lys Thr Ile Ser Lys Ala Lys Gly Gln Pro Arg Glu Pro Gln Val Tyr
            180             185             190

Thr Leu Pro Pro Ser Arg Glu Glu Met Thr Lys Asn Gln Val Ser Leu
        195             200             205

Thr Cys Leu Val Lys Gly Phe Tyr Pro Ser Asp Ile Ala Val Glu Trp
    210             215             220

Glu Ser Asn Gly Gln Pro Glu Asn Asn Tyr Lys Thr Thr Pro Pro Val
225             230             235             240

Leu Asp Ser Asp Gly Ser Phe Phe Leu Tyr Ser Lys Leu Thr Val Asp
                245             250             255

Lys Ser Arg Trp Gln Gln Gly Asn Val Phe Ser Cys Ser Val Met His
            260             265             270

Glu Ala Leu His Asn His Tyr Thr Gln Lys Ser Leu Ser Leu Ser Pro
        275             280             285

Gly Lys
```

-continued

290

```
<210> SEQ ID NO 98
<211> LENGTH: 290
<212> TYPE: PRT
<213> ORGANISM: Artificial Sequence
<220> FEATURE:
<223> OTHER INFORMATION: huNRG1(S177-Q237)(3D6)::GG::huFcSEFL2 (Pb)

<400> SEQUENCE: 98

Ser His Leu Val Lys Cys Gly Glu Ser Asp Lys Ser Phe Cys Val Asn
1               5                   10                  15

Gly Gly Glu Cys Phe Val Ile Glu Gly Ser Ser Ile Pro Ser Arg Phe
            20                  25                  30

Leu Cys Lys Cys Pro Asn Glu Phe Thr Gly Asp Arg Cys Gln Asp Phe
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290

<210> SEQ ID NO 99
<211> LENGTH: 290
<212> TYPE: PRT
<213> ORGANISM: Artificial Sequence
<220> FEATURE:
<223> OTHER INFORMATION: huNRG1(S177-Q237)(3E6)::GG::huFcSEFL2 (Pb)

<400> SEQUENCE: 99
```

```
Ser His Leu Val Lys Cys Gly Glu Lys Asp Lys Thr Phe Cys Val Asn
1               5                   10                  15

Gly Gly Glu Cys Phe Met Val Glu Asp Leu Ser Ile Pro Ser Arg Phe
            20                  25                  30

Leu Cys Lys Cys Pro Asn Glu Phe Thr Gly Asp Arg Cys Gln Asp Phe
            35                  40                  45

Phe Met Ala Ser Phe Tyr Lys Ala Glu Glu Leu Tyr Gln Gly Gly Asp
        50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290
```

```
<210> SEQ ID NO 100
<211> LENGTH: 290
<212> TYPE: PRT
<213> ORGANISM: Artificial Sequence
<220> FEATURE:
<223> OTHER INFORMATION: huNRG1(S177-Q237)(3E6)::GG::huFcSEFL2 (Pb)

<400> SEQUENCE: 100
```

```
Ser His Leu Val Lys Cys Ala Glu Lys His Lys Ser Phe Cys Val Asn
1               5                   10                  15

Gly Gly Glu Cys Tyr Val Ile Glu Gly Ser Ser Ile Pro Ser Arg Phe
            20                  25                  30

Leu Cys Lys Cys Pro Asn Glu Phe Thr Gly Asp Arg Cys Gln Lys Asp
            35                  40                  45

Phe Met Ala Ser Phe Tyr Lys Ala Glu Glu Leu Tyr Gln Gly Gly Asp
        50                  55                  60
```

```
Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
            130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290
```

```
<210> SEQ ID NO 101
<211> LENGTH: 290
<212> TYPE: PRT
<213> ORGANISM: Artificial Sequence
<220> FEATURE:
<223> OTHER INFORMATION: huNRG1(S177-Q237)(3F2)::GG::huFcSEFL2 (Pb)

<400> SEQUENCE: 101
```

```
Ser His Leu Val Lys Cys Ala Glu Asn His Lys Thr Phe Cys Val Asn
1               5                   10                  15

Gly Gly Glu Cys Phe Val Ile Glu Gly Ser Ser Asn Pro Ser Arg Tyr
            20                  25                  30

Leu Cys Lys Cys Pro Asn Glu Phe Thr Gly Asp Arg Cys Gln Asp Val
            35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125
```

-continued

```
Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
    275                 280                 285

Gly Lys
    290
```

```
<210> SEQ ID NO 102
<211> LENGTH: 290
<212> TYPE: PRT
<213> ORGANISM: Artificial Sequence
<220> FEATURE:
<223> OTHER INFORMATION: huNRG1(S177-Q237)(3F2)::GG::huFcSEFL2 (Pb)

<400> SEQUENCE: 102
```

```
Ser His Leu Val Lys Cys Gly Glu Ser His Lys Ser Phe Cys Val Asn
1               5                   10                  15

Gly Gly Glu Cys Phe Met Ile Glu Gly Pro Ser Asn Pro Ser Arg Tyr
                20                  25                  30

Leu Cys Lys Cys Pro Asn Glu Phe Thr Gly Asp Arg Cys Gln Asp Asp
            35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190
```

-continued

```
Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
            275                 280                 285

Gly Lys
    290
```

```
<210> SEQ ID NO 103
<211> LENGTH: 290
<212> TYPE: PRT
<213> ORGANISM: Artificial Sequence
<220> FEATURE:
<223> OTHER INFORMATION: huNRG1(S177-Q237)(3G3)::GG::huFcSEFL2 (Pb)

<400> SEQUENCE: 103
```

```
Ser His Leu Val Lys Cys Gly Glu Arg Glu Lys Thr Phe Cys Val Asn
1               5                   10                  15

Gly Gly Glu Cys Phe Met Ile Glu His Leu Ser Ile Pro Ser Arg Phe
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255
```

-continued

```
Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 104
<211> LENGTH: 290
<212> TYPE: PRT
<213> ORGANISM: Artificial Sequence
<220> FEATURE:
<223> OTHER INFORMATION: huNRG1(S177-Q237)(3G9)::GG::huFcSEFL2 (Pb)

<400> SEQUENCE: 104

Ser His Leu Val Lys Cys Gly Glu Ser His Lys Ser Phe Cys Val Asn
1               5                   10                  15

Gly Gly Glu Cys Phe Met Val Glu Asp Leu Ser Asn Pro Ser Arg Phe
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 105
<211> LENGTH: 290
```

-continued

```
<212> TYPE: PRT
<213> ORGANISM: Artificial Sequence
<220> FEATURE:
<223> OTHER INFORMATION: huNRG1(S177-Q237)(3H5)::GG::huFcSEFL2 (Pb)

<400> SEQUENCE: 105

Ser His Leu Val Lys Cys Gly Glu Arg His Lys Ser Phe Cys Val Asn
1               5                   10                  15

Gly Gly Glu Cys Tyr Val Val Glu Arg Pro Ser Ile Pro Ser Arg Phe
            20                  25                  30

Leu Cys Lys Cys Pro Asn Glu Phe Thr Gly Asp Arg Cys Gln Lys Asp
        35                  40                  45

Phe Leu Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
        210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
            245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 106
<211> LENGTH: 290
<212> TYPE: PRT
<213> ORGANISM: Artificial Sequence
<220> FEATURE:
<223> OTHER INFORMATION: huNRG1(S177-Q237)(3H8)::GG::huFcSEFL2 (Pb)

<400> SEQUENCE: 106

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30
```

```
Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
            275                 280                 285

Gly Lys
    290
```

<210> SEQ ID NO 107
<211> LENGTH: 290
<212> TYPE: PRT
<213> ORGANISM: Artificial Sequence
<220> FEATURE:
<223> OTHER INFORMATION: huNRG1(S177-Q237)(_200E)::GG::huFcSEFL2 (Pb)

<400> SEQUENCE: 107

```
Ser His Leu Val Lys Cys Ala Glu Lys Glu Lys Thr Phe Cys Val Asn
1               5                   10                  15

Gly Gly Glu Cys Phe Met Val Glu Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95
```

```
Ser Arg Thr Pro Glu Val Thr Cys Val Val Val Asp Val Ser His Glu
        100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
        275                 280                 285

Gly Lys
    290
```

<210> SEQ ID NO 108
<211> LENGTH: 290
<212> TYPE: PRT
<213> ORGANISM: Artificial Sequence
<220> FEATURE:
<223> OTHER INFORMATION: huNRG1(S177-Q237)(_200E_KDF)::GG::huFcSEFL2
      (Pb)

<400> SEQUENCE: 108

```
Ser His Leu Val Lys Cys Ala Glu Lys Glu Lys Thr Phe Cys Val Asn
1               5                   10                  15

Gly Gly Glu Cys Phe Met Val Glu Asp Leu Ser Asn Pro Ser Arg Tyr
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
        100                 105                 110

Asp Pro Glu Val Lys Phe Asn Trp Tyr Val Asp Gly Val Glu Val His
        115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
```

-continued

```
145              150              155              160

Glu Tyr Lys Cys Lys Val Ser Asn Lys Ala Leu Pro Ala Pro Ile Glu
                165              170              175

Lys Thr Ile Ser Lys Ala Lys Gly Gln Pro Arg Glu Pro Gln Val Tyr
                180              185              190

Thr Leu Pro Pro Ser Arg Glu Glu Met Thr Lys Asn Gln Val Ser Leu
                195              200              205

Thr Cys Leu Val Lys Gly Phe Tyr Pro Ser Asp Ile Ala Val Glu Trp
    210              215              220

Glu Ser Asn Gly Gln Pro Glu Asn Asn Tyr Lys Thr Thr Pro Pro Val
225              230              235              240

Leu Asp Ser Asp Gly Ser Phe Phe Leu Tyr Ser Lys Leu Thr Val Asp
                245              250              255

Lys Ser Arg Trp Gln Gln Gly Asn Val Phe Ser Cys Ser Val Met His
                260              265              270

Glu Ala Leu His Asn His Tyr Thr Gln Lys Ser Leu Ser Leu Ser Pro
                275              280              285

Gly Lys
    290

<210> SEQ ID NO 109
<211> LENGTH: 290
<212> TYPE: PRT
<213> ORGANISM: Artificial Sequence
<220> FEATURE:
<223> OTHER INFORMATION: huNRG1(S177-Q237)(_FVIEDPSI)::GG::huFcSEFL2
      (Pb)

<400> SEQUENCE: 109

Ser His Leu Val Lys Cys Ala Glu Lys Glu Lys Thr Phe Cys Val Asn
1               5               10              15

Gly Gly Glu Cys Phe Val Ile Glu Asp Pro Ser Ile Pro Ser Arg Tyr
                20              25              30

Leu Cys Lys Cys Pro Asn Glu Phe Thr Gly Asp Arg Cys Gln Asn Tyr
                35              40              45

Val Met Ala Ser Phe Tyr Lys Ala Glu Glu Leu Tyr Gln Gly Gly Asp
    50              55              60

Lys Thr His Thr Cys Pro Pro Cys Pro Ala Pro Glu Leu Leu Gly Gly
65              70              75              80

Pro Ser Val Phe Leu Phe Pro Pro Lys Pro Lys Asp Thr Leu Met Ile
                85              90              95

Ser Arg Thr Pro Glu Val Thr Cys Val Val Val Asp Val Ser His Glu
                100             105             110

Asp Pro Glu Val Lys Phe Asn Trp Tyr Val Asp Gly Val Glu Val His
                115             120             125

Asn Ala Lys Thr Lys Pro Cys Glu Glu Gln Tyr Gly Ser Thr Tyr Arg
    130             135             140

Cys Val Ser Val Leu Thr Val Leu His Gln Asp Trp Leu Asn Gly Lys
145             150             155             160

Glu Tyr Lys Cys Lys Val Ser Asn Lys Ala Leu Pro Ala Pro Ile Glu
                165             170             175

Lys Thr Ile Ser Lys Ala Lys Gly Gln Pro Arg Glu Pro Gln Val Tyr
                180             185             190

Thr Leu Pro Pro Ser Arg Glu Glu Met Thr Lys Asn Gln Val Ser Leu
                195             200             205
```

```
Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270

Glu Ala Leu His Asn His Tyr Thr Gln Lys Ser Leu Ser Leu Ser Pro
                275                 280                 285

Gly Lys
    290
```

```
<210> SEQ ID NO 110
<211> LENGTH: 290
<212> TYPE: PRT
<213> ORGANISM: Artificial Sequence
<220> FEATURE:
<223> OTHER INFORMATION: huNRG1(S177-Q237)(v80)::GG::huFcSEFL2 (Pb)

<400> SEQUENCE: 110
```

```
Ser His Leu Val Lys Cys Ala Glu Ser His Lys Ser Phe Cys Val Asn
1               5                   10                  15

Gly Gly Glu Cys Phe Val Ile Glu Gly Ser Ser Ile Pro Ser Arg Tyr
            20                  25                  30

Leu Cys Lys Cys Pro Asn Glu Phe Thr Gly Asp Arg Cys Gln Lys Asp
            35                  40                  45

Val Met Ala Ser Phe Tyr Lys Ala Glu Glu Leu Tyr Gln Gly Gly Asp
        50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
        130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
                180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
                260                 265                 270
```

-continued

```
Glu Ala Leu His Asn His Tyr Thr Gln Lys Ser Leu Ser Leu Ser Pro
    275                 280                 285

Gly Lys
    290

<210> SEQ ID NO 111
<211> LENGTH: 290
<212> TYPE: PRT
<213> ORGANISM: Artificial Sequence
<220> FEATURE:
<223> OTHER INFORMATION: huNRG1(S177-Q237)(v80.3)::GG::huFcSEFL2 (Pb)

<400> SEQUENCE: 111

Ser His Leu Val Lys Cys Ala Glu Arg His Lys Ser Phe Cys Val Asn
1               5                   10                  15

Gly Gly Glu Cys Phe Val Ile Glu Gly Ser Ser Ile Pro Ser Arg Tyr
            20                  25                  30

Leu Cys Lys Cys Pro Asn Glu Phe Thr Gly Asp Arg Cys Glu Lys Asp
        35                  40                  45

Val Met Ala Ser Phe Tyr Lys Ala Glu Glu Leu Tyr Gln Gly Gly Asp
    50                  55                  60

Lys Thr His Thr Cys Pro Pro Cys Pro Ala Pro Glu Leu Leu Gly Gly
65                  70                  75                  80

Pro Ser Val Phe Leu Phe Pro Pro Lys Pro Lys Asp Thr Leu Met Ile
            85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
            115                 120                 125

Asn Ala Lys Thr Lys Pro Cys Glu Glu Gln Tyr Gly Ser Thr Tyr Arg
    130                 135                 140

Cys Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
            165                 170                 175

Lys Thr Ile Ser Lys Ala Lys Gly Gln Pro Arg Glu Pro Gln Val Tyr
            180                 185                 190

Thr Leu Pro Pro Ser Arg Glu Glu Met Thr Lys Asn Gln Val Ser Leu
            195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
            245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
    275                 280                 285

Gly Lys
    290

<210> SEQ ID NO 112
<211> LENGTH: 61
<212> TYPE: PRT
<213> ORGANISM: Homo sapiens
```

-continued

<400> SEQUENCE: 112

```
Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60
```

<210> SEQ ID NO 113
<211> LENGTH: 10
<212> TYPE: PRT
<213> ORGANISM: Artificial Sequence
<220> FEATURE:
<223> OTHER INFORMATION: G4S Linker

<400> SEQUENCE: 113

```
Gly Gly Gly Gly Ser Gly Gly Gly Gly Ser
1               5                   10
```

<210> SEQ ID NO 114
<211> LENGTH: 61
<212> TYPE: PRT
<213> ORGANISM: Artificial Sequence
<220> FEATURE:
<223> OTHER INFORMATION: NRG1(S177-Q237) (NRGE1A)

<400> SEQUENCE: 114

```
Ser His Leu Val Lys Cys Ala Glu Asn Asp Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln
    50                  55                  60
```

<210> SEQ ID NO 115
<211> LENGTH: 61
<212> TYPE: PRT
<213> ORGANISM: Artificial Sequence
<220> FEATURE:
<223> OTHER INFORMATION: NRG1(S177-Q237) (NRGE1B)

<400> SEQUENCE: 115

```
Ser His Leu Val Lys Cys Gly Glu Asn Asp Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln
    50                  55                  60
```

<210> SEQ ID NO 116
<211> LENGTH: 52
<212> TYPE: PRT
<213> ORGANISM: Artificial Sequence
<220> FEATURE:
<223> OTHER INFORMATION: NRG1(S177-S228) (NRGE1C)

-continued

<400> SEQUENCE: 116

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser
    50

<210> SEQ ID NO 117
<211> LENGTH: 53
<212> TYPE: PRT
<213> ORGANISM: Artificial Sequence
<220> FEATURE:
<223> OTHER INFORMATION: NRG1(S177-F229) (NRGE1C)

<400> SEQUENCE: 117

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe
    50

<210> SEQ ID NO 118
<211> LENGTH: 53
<212> TYPE: PRT
<213> ORGANISM: Artificial Sequence
<220> FEATURE:
<223> OTHER INFORMATION: NRG1(S177-F229) (NRGE1C TQI)

<400> SEQUENCE: 118

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Thr
        35                  40                  45

Gln Ile Ala Ser Phe
    50

<210> SEQ ID NO 119
<211> LENGTH: 53
<212> TYPE: PRT
<213> ORGANISM: Artificial Sequence
<220> FEATURE:
<223> OTHER INFORMATION: NRG1(S177-F229) (NRGE1C APHI)

<400> SEQUENCE: 119

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Ala Pro
        35                  40                  45

His Ile Ala Ser Phe
    50

<210> SEQ ID NO 120
<211> LENGTH: 53
<212> TYPE: PRT
<213> ORGANISM: Artificial Sequence
<220> FEATURE:
<223> OTHER INFORMATION: NRG1(S177-F229) (NRGE1C KTSL)

<400> SEQUENCE: 120

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Lys Thr
        35                  40                  45

Ser Leu Ala Ser Phe
    50

<210> SEQ ID NO 121
<211> LENGTH: 53
<212> TYPE: PRT
<213> ORGANISM: Artificial Sequence
<220> FEATURE:
<223> OTHER INFORMATION: NRG1(S177-F229) (NRGE1C QSP)

<400> SEQUENCE: 121

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Gln Ser
        35                  40                  45

Phe Pro Ala Ser Phe
    50

<210> SEQ ID NO 122
<211> LENGTH: 53
<212> TYPE: PRT
<213> ORGANISM: Artificial Sequence
<220> FEATURE:
<223> OTHER INFORMATION: NRG1(S177-F229) (NRGE1C SALT)

<400> SEQUENCE: 122

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Ser Ala
        35                  40                  45

Leu Thr Ala Ser Phe
    50

<210> SEQ ID NO 123
<211> LENGTH: 53
<212> TYPE: PRT
<213> ORGANISM: Artificial Sequence
<220> FEATURE:
<223> OTHER INFORMATION: NRG1(S177-F229) (NRGE1C STRV)

<400> SEQUENCE: 123

Ser His Leu Val Lys Cys Gly Glu Lys His Lys Ser Phe Cys Val Asn
1               5                   10                  15

-continued

```
Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Ser Thr
        35                  40                  45

Arg Val Ala Ser Phe
    50

<210> SEQ ID NO 124
<211> LENGTH: 61
<212> TYPE: PRT
<213> ORGANISM: Artificial Sequence
<220> FEATURE:
<223> OTHER INFORMATION: NRG1(S177-Q237) (NRGE1C)

<400> SEQUENCE: 124

Ser His Leu Val Lys Cys Gly Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln
    50                  55                  60

<210> SEQ ID NO 125
<211> LENGTH: 52
<212> TYPE: PRT
<213> ORGANISM: Artificial Sequence
<220> FEATURE:
<223> OTHER INFORMATION: NRG1(S177-S228) (NRGE1D)

<400> SEQUENCE: 125

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser
    50

<210> SEQ ID NO 126
<211> LENGTH: 53
<212> TYPE: PRT
<213> ORGANISM: Artificial Sequence
<220> FEATURE:
<223> OTHER INFORMATION: NRG1(S177-F229) (NRGE1D)

<400> SEQUENCE: 126

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe
    50

<210> SEQ ID NO 127
<211> LENGTH: 53
```

```
<212> TYPE: PRT
<213> ORGANISM: Artificial Sequence
<220> FEATURE:
<223> OTHER INFORMATION: NRG1(S177-F229) (NRGE1D KLDI)

<400> SEQUENCE: 127

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Lys Leu
        35                  40                  45

Asp Ile Ala Ser Phe
    50

<210> SEQ ID NO 128
<211> LENGTH: 53
<212> TYPE: PRT
<213> ORGANISM: Artificial Sequence
<220> FEATURE:
<223> OTHER INFORMATION: NRG1(S177-F229) (NRGE1D SSEL)

<400> SEQUENCE: 128

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Ser Ser
        35                  40                  45

Glu Leu Ala Ser Phe
    50

<210> SEQ ID NO 129
<211> LENGTH: 53
<212> TYPE: PRT
<213> ORGANISM: Artificial Sequence
<220> FEATURE:
<223> OTHER INFORMATION: NRG1(S177-F229) (NRGE1D TSLL)

<400> SEQUENCE: 129

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Thr Ser
        35                  40                  45

Leu Leu Ala Ser Phe
    50

<210> SEQ ID NO 130
<211> LENGTH: 53
<212> TYPE: PRT
<213> ORGANISM: Artificial Sequence
<220> FEATURE:
<223> OTHER INFORMATION: NRG1(S177-F229) (NRGE1D VTRL)

<400> SEQUENCE: 130

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30
```

```
Leu Cys Lys Cys Pro Asn Glu Phe Thr Gly Asp Arg Cys Gln Val Thr
        35                  40                  45

Arg Leu Ala Ser Phe
    50
```

<210> SEQ ID NO 131
<211> LENGTH: 61
<212> TYPE: PRT
<213> ORGANISM: Artificial Sequence
<220> FEATURE:
<223> OTHER INFORMATION: NRG1(S177-Q237) (NRGE1D)

<400> SEQUENCE: 131

```
Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
        20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln
    50                  55                  60
```

<210> SEQ ID NO 132
<211> LENGTH: 61
<212> TYPE: PRT
<213> ORGANISM: Artificial Sequence
<220> FEATURE:
<223> OTHER INFORMATION: NRG1(S177-Q237) (NRGE1E)

<400> SEQUENCE: 132

```
Ser His Leu Val Lys Cys Gly Glu Asn Asp Lys Ser Phe Cys Val Asn
1               5                   10                  15

Gly Gly Glu Cys Phe Met Ile Glu Gly Pro Ser Asn Pro Ser Arg Tyr
        20                  25                  30

Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln
    50                  55                  60
```

<210> SEQ ID NO 133
<211> LENGTH: 61
<212> TYPE: PRT
<213> ORGANISM: Artificial Sequence
<220> FEATURE:
<223> OTHER INFORMATION: NRG1(S177-Q237) (NRGE1F)

<400> SEQUENCE: 133

```
Ser His Leu Val Lys Cys Ala Glu Asn Asp Lys Ser Phe Cys Val Asn
1               5                   10                  15

Gly Gly Glu Cys Tyr Met Val Glu Gly Ser Ser Ile Pro Ser Arg Tyr
        20                  25                  30

Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln
    50                  55                  60
```

<210> SEQ ID NO 134
<211> LENGTH: 61
<212> TYPE: PRT
<213> ORGANISM: Artificial Sequence
<220> FEATURE:
<223> OTHER INFORMATION: NRG1(S177-Q237) (NRGE1G)

<400> SEQUENCE: 134

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln
    50                  55                  60

<210> SEQ ID NO 135
<211> LENGTH: 61
<212> TYPE: PRT
<213> ORGANISM: Artificial Sequence
<220> FEATURE:
<223> OTHER INFORMATION: NRG1(S177-Q237) (NRGE1H)

<400> SEQUENCE: 135

Ser His Leu Val Lys Cys Gly Glu Ser His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asn Asp
        35                  40                  45

Phe Met Ala Ser Phe Tyr Lys Ala Glu Glu Leu Tyr Gln
    50                  55                  60

<210> SEQ ID NO 136
<211> LENGTH: 61
<212> TYPE: PRT
<213> ORGANISM: Artificial Sequence
<220> FEATURE:
<223> OTHER INFORMATION: NRG1(S177-Q237) (NRGE1I)

<400> SEQUENCE: 136

Ser His Leu Val Lys Cys Gly Glu Asn Asp Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln
    50                  55                  60

<210> SEQ ID NO 137
<211> LENGTH: 61
<212> TYPE: PRT
<213> ORGANISM: Artificial Sequence
<220> FEATURE:
<223> OTHER INFORMATION: NRG1(S177-Q237) (NRGE1J)

<400> SEQUENCE: 137

Ser His Leu Val Lys Cys Gly Glu Asn Asp Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln

-continued

```
        50              55              60

<210> SEQ ID NO 138
<211> LENGTH: 61
<212> TYPE: PRT
<213> ORGANISM: Artificial Sequence
<220> FEATURE:
<223> OTHER INFORMATION: NRG1(S177-Q237) (NRGE1K)

<400> SEQUENCE: 138

Ser His Leu Val Lys Cys Ala Glu Lys His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln
        50                  55                  60

<210> SEQ ID NO 139
<211> LENGTH: 61
<212> TYPE: PRT
<213> ORGANISM: Artificial Sequence
<220> FEATURE:
<223> OTHER INFORMATION: NRG1(S177-Q237) (NRGE1L)

<400> SEQUENCE: 139

Ser His Leu Val Lys Cys Gly Glu Ser His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln
        50                  55                  60

<210> SEQ ID NO 140
<211> LENGTH: 61
<212> TYPE: PRT
<213> ORGANISM: Artificial Sequence
<220> FEATURE:
<223> OTHER INFORMATION: NRG1(S177-Q237) (NRGE1M)

<400> SEQUENCE: 140

Ser His Leu Val Lys Cys Gly Glu Asn Asp Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Phe
        35                  40                  45

Phe Met Ala Ser Phe Tyr Lys Ala Glu Glu Leu Tyr Gln
        50                  55                  60

<210> SEQ ID NO 141
<211> LENGTH: 61
<212> TYPE: PRT
<213> ORGANISM: Artificial Sequence
<220> FEATURE:
<223> OTHER INFORMATION: NRG1(S177-Q237) (NRGE1N)

<400> SEQUENCE: 141

Ser His Leu Val Lys Cys Gly Glu Asn Asp Lys Ser Phe Cys Val Asn
```

-continued

```
1             5              10             15

Gly Gly Glu Cys Tyr Met Val Glu Gly Ser Ser Ile Pro Ser Arg Tyr
            20             25             30

Leu Cys Lys Cys Pro Asn Glu Phe Thr Gly Asp Arg Cys Gln Asp Phe
        35             40             45

Phe Met Ala Ser Phe Tyr Lys Ala Glu Glu Leu Tyr Gln
    50             55             60
```

```
<210> SEQ ID NO 142
<211> LENGTH: 61
<212> TYPE: PRT
<213> ORGANISM: Artificial Sequence
<220> FEATURE:
<223> OTHER INFORMATION: NRG1(S177-Q237) (NRGE1O)

<400> SEQUENCE: 142

Ser His Leu Val Lys Cys Gly Glu Lys His Lys Ser Phe Cys Val Asn
1             5              10             15

Gly Gly Glu Cys Tyr Met Val Glu Gly Ser Ser Ile Pro Ser Arg Tyr
            20             25             30

Leu Cys Lys Cys Pro Asn Glu Phe Thr Gly Asp Arg Cys Gln Asp Phe
        35             40             45

Phe Met Ala Ser Phe Tyr Lys Ala Glu Glu Leu Tyr Gln
    50             55             60
```

```
<210> SEQ ID NO 143
<211> LENGTH: 61
<212> TYPE: PRT
<213> ORGANISM: Artificial Sequence
<220> FEATURE:
<223> OTHER INFORMATION: NRG1(S177-Q237) (NRGE1P)

<400> SEQUENCE: 143

Ser His Leu Val Lys Cys Ala Glu Ser His Lys Ser Phe Cys Val Asn
1             5              10             15

Gly Gly Glu Cys Phe Met Ile Glu Gly Pro Ser Asn Pro Ser Arg Tyr
            20             25             30

Leu Cys Lys Cys Pro Asn Glu Phe Thr Gly Asp Arg Cys Gln Asp Phe
        35             40             45

Phe Met Ala Ser Phe Tyr Lys Ala Glu Glu Leu Tyr Gln
    50             55             60
```

```
<210> SEQ ID NO 144
<211> LENGTH: 61
<212> TYPE: PRT
<213> ORGANISM: Artificial Sequence
<220> FEATURE:
<223> OTHER INFORMATION: NRG1(S177-Q237) (1A1)

<400> SEQUENCE: 144

Ser His Leu Val Lys Cys Gly Glu Ser Glu Lys Ser Phe Cys Val Asn
1             5              10             15

Gly Gly Glu Cys Tyr Val Ile Glu Asp Ser Ser Ile Pro Ser Arg Phe
            20             25             30

Leu Cys Lys Cys Pro Asn Glu Phe Thr Gly Asp Arg Cys Gln Asn Val
        35             40             45

Phe Leu Ala Ser Phe Tyr Lys Ala Glu Glu Leu Tyr Gln
    50             55             60
```

```
<210> SEQ ID NO 145
```

```
<211> LENGTH: 61
<212> TYPE: PRT
<213> ORGANISM: Artificial Sequence
<220> FEATURE:
<223> OTHER INFORMATION: NRG1(S177-Q237) (1A12)

<400> SEQUENCE: 145

Ser His Leu Val Lys Cys Ala Glu Lys His Lys Ser Phe Cys Val Asn
1               5                   10                  15

Gly Gly Glu Cys Tyr Val Val Glu Arg Pro Ser Ile Pro Ser Arg Tyr
            20                  25                  30

Leu Cys Lys Cys Pro Asn Glu Phe Thr Gly Asp Arg Cys Gln Lys Phe
        35                  40                  45

Phe Met Ala Ser Phe Tyr Lys Ala Glu Glu Leu Tyr Gln
    50                  55                  60

<210> SEQ ID NO 146
<211> LENGTH: 61
<212> TYPE: PRT
<213> ORGANISM: Artificial Sequence
<220> FEATURE:
<223> OTHER INFORMATION: NRG1(S177-Q237)  (1A7)

<400> SEQUENCE: 146

Ser His Leu Val Lys Cys Ala Glu Arg Asp Lys Ser Phe Cys Val Asn
1               5                   10                  15

Gly Gly Glu Cys Tyr Val Ile Glu His Leu Ser Asn Pro Ser Arg Phe
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln
    50                  55                  60

<210> SEQ ID NO 147
<211> LENGTH: 61
<212> TYPE: PRT
<213> ORGANISM: Artificial Sequence
<220> FEATURE:
<223> OTHER INFORMATION: NRG1(S177-Q237) (1B4)

<400> SEQUENCE: 147

Ser His Leu Val Lys Cys Gly Glu Arg Asp Lys Thr Phe Cys Val Asn
1               5                   10                  15

Gly Gly Glu Cys Phe Met Ile Glu Asp Ser Ser Asn Pro Ser Arg Tyr
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln
    50                  55                  60

<210> SEQ ID NO 148
<211> LENGTH: 61
<212> TYPE: PRT
<213> ORGANISM: Artificial Sequence
<220> FEATURE:
<223> OTHER INFORMATION: NRG1(S177-Q237) (1B9)

<400> SEQUENCE: 148

Ser His Leu Val Lys Cys Ala Glu Lys His Lys Ser Phe Cys Val Asn
1               5                   10                  15

Gly Gly Glu Cys Phe Met Val Glu Asp Leu Ser Ile Pro Ser Arg Tyr
            20                  25                  30
```

-continued

```
Leu Cys Lys Cys Pro Asn Glu Phe Thr Gly Asp Arg Cys Gln Asp Val
        35                  40                  45

Phe Met Ala Ser Phe Tyr Lys Ala Glu Glu Leu Tyr Gln
    50                  55                  60

<210> SEQ ID NO 149
<211> LENGTH: 61
<212> TYPE: PRT
<213> ORGANISM: Artificial Sequence
<220> FEATURE:
<223> OTHER INFORMATION: NRG1(S177-Q237) (1C11)

<400> SEQUENCE: 149

Ser His Leu Val Lys Cys Gly Glu Lys Glu Lys Thr Phe Cys Val Asn
1               5                   10                  15

Gly Gly Glu Cys Tyr Met Val Glu Arg Pro Ser Ile Pro Ser Arg Phe
            20                  25                  30

Leu Cys Lys Cys Pro Asn Glu Phe Thr Gly Asp Arg Cys Gln Lys Phe
        35                  40                  45

Phe Met Ala Ser Phe Tyr Lys Ala Glu Glu Leu Tyr Gln
    50                  55                  60

<210> SEQ ID NO 150
<211> LENGTH: 61
<212> TYPE: PRT
<213> ORGANISM: Artificial Sequence
<220> FEATURE:
<223> OTHER INFORMATION: NRG1(S177-Q237)    (1D10)

<400> SEQUENCE: 150

Ser His Leu Val Lys Cys Ala Glu Arg Asp Lys Thr Phe Cys Val Asn
1               5                   10                  15

Gly Gly Glu Cys Tyr Met Ile Glu Asp Leu Ser Ile Pro Ser Arg Tyr
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln
    50                  55                  60

<210> SEQ ID NO 151
<211> LENGTH: 61
<212> TYPE: PRT
<213> ORGANISM: Artificial Sequence
<220> FEATURE:
<223> OTHER INFORMATION: NRG1(S177-Q237) (1D3)

<400> SEQUENCE: 151

Ser His Leu Val Lys Cys Gly Glu Asn Asp Lys Ser Phe Cys Val Asn
1               5                   10                  15

Gly Gly Glu Cys Phe Val Ile Glu Asp Pro Ser Ile Pro Ser Arg Tyr
            20                  25                  30

Leu Cys Lys Cys Pro Asn Glu Phe Thr Gly Asp Arg Cys Gln Asn Asp
        35                  40                  45

Phe Leu Ala Ser Phe Tyr Lys Ala Glu Glu Leu Tyr Gln
    50                  55                  60

<210> SEQ ID NO 152
<211> LENGTH: 61
<212> TYPE: PRT
<213> ORGANISM: Artificial Sequence
<220> FEATURE:
```

<223> OTHER INFORMATION: NRG1(S177-Q237) (1D4)

<400> SEQUENCE: 152

```
Ser His Leu Val Lys Cys Gly Glu Arg Asp Lys Thr Phe Cys Val Asn
1               5                   10                  15

Gly Gly Glu Cys Tyr Val Val Glu His Ser Ser Asn Pro Ser Arg Tyr
            20                  25                  30

Leu Cys Lys Cys Pro Asn Glu Phe Thr Gly Asp Arg Cys Gln Lys Phe
        35                  40                  45

Phe Leu Ala Ser Phe Tyr Lys Ala Glu Glu Leu Tyr Gln
    50                  55                  60
```

<210> SEQ ID NO 153
<211> LENGTH: 61
<212> TYPE: PRT
<213> ORGANISM: Artificial Sequence
<220> FEATURE:
<223> OTHER INFORMATION: NRG1(S177-Q237)(2E3)

<400> SEQUENCE: 153

```
Ser His Leu Val Lys Cys Gly Glu Lys Glu Lys Ser Phe Cys Val Asn
1               5                   10                  15

Gly Gly Glu Cys Tyr Met Ile Glu Gly Leu Ser Ile Pro Ser Arg Phe
            20                  25                  30

Leu Cys Lys Cys Pro Asn Glu Phe Thr Gly Asp Arg Cys Gln Asp Val
        35                  40                  45

Phe Met Ala Ser Phe Tyr Lys Ala Glu Glu Leu Tyr Gln
    50                  55                  60
```

<210> SEQ ID NO 154
<211> LENGTH: 61
<212> TYPE: PRT
<213> ORGANISM: Artificial Sequence
<220> FEATURE:
<223> OTHER INFORMATION: NRG1(S177-Q237) (2E4)

<400> SEQUENCE: 154

```
Ser His Leu Val Lys Cys Gly Glu Ser Asp Lys Ser Phe Cys Val Asn
1               5                   10                  15

Gly Gly Glu Cys Phe Met Val Lys Arg Pro Ser Asn Pro Ser Arg Tyr
            20                  25                  30

Leu Cys Lys Cys Pro Asn Glu Phe Thr Gly Asp Arg Cys Gln Lys Val
        35                  40                  45

Phe Leu Ala Ser Phe Tyr Lys Ala Glu Glu Leu Tyr Gln
    50                  55                  60
```

<210> SEQ ID NO 155
<211> LENGTH: 61
<212> TYPE: PRT
<213> ORGANISM: Artificial Sequence
<220> FEATURE:
<223> OTHER INFORMATION: NRG1(S177-Q237) (2F2)

<400> SEQUENCE: 155

```
Ser His Leu Val Lys Cys Ala Glu Ser Glu Lys Thr Phe Cys Val Asn
1               5                   10                  15

Gly Gly Glu Cys Tyr Met Ile Glu His Pro Ser Asn Pro Ser Arg Phe
            20                  25                  30

Leu Cys Lys Cys Pro Asn Glu Phe Thr Gly Asp Arg Cys Gln Asn Val
        35                  40                  45
```

```
Phe Met Ala Ser Phe Tyr Lys Ala Glu Glu Leu Tyr Gln
    50                  55                  60

<210> SEQ ID NO 156
<211> LENGTH: 61
<212> TYPE: PRT
<213> ORGANISM: Artificial Sequence
<220> FEATURE:
<223> OTHER INFORMATION: NRG1(S177-Q237) (2G3)

<400> SEQUENCE: 156

Ser His Leu Val Lys Cys Gly Glu Arg Gln Lys Ser Phe Cys Val Asn
1               5                   10                  15

Gly Gly Glu Cys Tyr Met Val Glu Asp Leu Ser Ile Pro Ser Arg Tyr
            20                  25                  30

Leu Cys Lys Cys Pro Asn Glu Phe Thr Gly Asp Arg Cys Gln Lys Val
        35                  40                  45

Phe Met Ala Ser Phe Tyr Lys Ala Glu Glu Leu Tyr Gln
    50                  55                  60

<210> SEQ ID NO 157
<211> LENGTH: 61
<212> TYPE: PRT
<213> ORGANISM: Artificial Sequence
<220> FEATURE:
<223> OTHER INFORMATION: NRG1(S177-Q237) (2G4)

<400> SEQUENCE: 157

Ser His Leu Val Lys Cys Ala Glu Asn Glu Lys Thr Phe Cys Val Asn
1               5                   10                  15

Gly Gly Glu Cys Phe Val Val Glu Gly Leu Ser Ile Pro Ser Arg Tyr
            20                  25                  30

Leu Cys Lys Cys Pro Asn Glu Phe Thr Gly Asp Arg Cys Gln Asp Val
        35                  40                  45

Phe Met Ala Ser Phe Tyr Lys Ala Glu Glu Leu Tyr Gln
    50                  55                  60

<210> SEQ ID NO 158
<211> LENGTH: 61
<212> TYPE: PRT
<213> ORGANISM: Artificial Sequence
<220> FEATURE:
<223> OTHER INFORMATION: NRG1(S177-Q237) (2H7)

<400> SEQUENCE: 158

Ser His Leu Val Lys Cys Gly Glu Lys Glu Lys Ser Phe Cys Val Asn
1               5                   10                  15

Gly Gly Glu Cys Tyr Val Val Glu Asp Leu Ser Ile Pro Ser Arg Phe
            20                  25                  30

Leu Cys Lys Cys Pro Asn Glu Phe Thr Gly Asp Arg Cys Gln Lys Val
        35                  40                  45

Val Met Ala Ser Phe Tyr Lys Ala Glu Glu Leu Tyr Gln
    50                  55                  60

<210> SEQ ID NO 159
<211> LENGTH: 61
<212> TYPE: PRT
<213> ORGANISM: Artificial Sequence
<220> FEATURE:
<223> OTHER INFORMATION: NRG1(S177-Q237) (3A7)

<400> SEQUENCE: 159
```

-continued

```
Ser His Leu Val Lys Cys Ala Glu Lys Glu Lys Ser Phe Cys Val Asn
1               5                   10                  15

Gly Gly Glu Cys Phe Val Ile Glu Gly Ser Ser Ile Pro Ser Arg Phe
            20                  25                  30

Leu Cys Lys Cys Pro Asn Glu Phe Thr Gly Asp Arg Cys Gln Lys Val
        35                  40                  45

Val Met Ala Ser Phe Tyr Lys Ala Glu Glu Leu Tyr Gln
    50                  55                  60
```

<210> SEQ ID NO 160
<211> LENGTH: 61
<212> TYPE: PRT
<213> ORGANISM: Artificial Sequence
<220> FEATURE:
<223> OTHER INFORMATION: NRG1(S177-Q237) (3B8)

<400> SEQUENCE: 160

```
Ser His Leu Val Lys Cys Gly Glu Arg Asp Lys Ser Phe Cys Val Asn
1               5                   10                  15

Gly Gly Glu Cys Phe Met Val Glu Arg Ser Ser Ile Pro Ser Arg Tyr
            20                  25                  30

Leu Cys Lys Cys Pro Asn Glu Phe Thr Gly Asp Arg Cys Gln Asp Phe
        35                  40                  45

Phe Leu Ala Ser Phe Tyr Lys Ala Glu Glu Leu Tyr Gln
    50                  55                  60
```

<210> SEQ ID NO 161
<211> LENGTH: 61
<212> TYPE: PRT
<213> ORGANISM: Artificial Sequence
<220> FEATURE:
<223> OTHER INFORMATION: NRG1(S177-Q237) (3D6)

<400> SEQUENCE: 161

```
Ser His Leu Val Lys Cys Gly Glu Ser Asp Lys Ser Phe Cys Val Asn
1               5                   10                  15

Gly Gly Glu Cys Phe Val Ile Glu Gly Ser Ser Ile Pro Ser Arg Phe
            20                  25                  30

Leu Cys Lys Cys Pro Asn Glu Phe Thr Gly Asp Arg Cys Gln Asp Phe
        35                  40                  45

Phe Met Ala Ser Phe Tyr Lys Ala Glu Glu Leu Tyr Gln
    50                  55                  60
```

<210> SEQ ID NO 162
<211> LENGTH: 61
<212> TYPE: PRT
<213> ORGANISM: Artificial Sequence
<220> FEATURE:
<223> OTHER INFORMATION: NRG1(S177-Q237) (3D8)

<400> SEQUENCE: 162

```
Ser His Leu Val Lys Cys Gly Glu Lys Asp Lys Thr Phe Cys Val Asn
1               5                   10                  15

Gly Gly Glu Cys Phe Met Val Glu Asp Leu Ser Ile Pro Ser Arg Phe
            20                  25                  30

Leu Cys Lys Cys Pro Asn Glu Phe Thr Gly Asp Arg Cys Gln Asp Phe
        35                  40                  45

Phe Met Ala Ser Phe Tyr Lys Ala Glu Glu Leu Tyr Gln
    50                  55                  60
```

-continued

<210> SEQ ID NO 163
<211> LENGTH: 61
<212> TYPE: PRT
<213> ORGANISM: Artificial Sequence
<220> FEATURE:
<223> OTHER INFORMATION: NRG1(S177-Q237)(3E6)

<400> SEQUENCE: 163

Ser His Leu Val Lys Cys Ala Glu Lys His Lys Ser Phe Cys Val Asn
1               5                   10                  15

Gly Gly Glu Cys Tyr Val Ile Glu Gly Ser Ser Ile Pro Ser Arg Phe
            20                  25                  30

Leu Cys Lys Cys Pro Asn Glu Phe Thr Gly Asp Arg Cys Gln Lys Asp
        35                  40                  45

Phe Met Ala Ser Phe Tyr Lys Ala Glu Glu Leu Tyr Gln
    50                  55                  60

<210> SEQ ID NO 164
<211> LENGTH: 61
<212> TYPE: PRT
<213> ORGANISM: Artificial Sequence
<220> FEATURE:
<223> OTHER INFORMATION: NRG1(S177-Q237)(3E9)

<400> SEQUENCE: 164

Ser His Leu Val Lys Cys Ala Glu Asn His Lys Thr Phe Cys Val Asn
1               5                   10                  15

Gly Gly Glu Cys Phe Val Ile Glu Gly Ser Ser Asn Pro Ser Arg Tyr
            20                  25                  30

Leu Cys Lys Cys Pro Asn Glu Phe Thr Gly Asp Arg Cys Gln Asp Val
        35                  40                  45

Phe Leu Ala Ser Phe Tyr Lys Ala Glu Glu Leu Tyr Gln
    50                  55                  60

<210> SEQ ID NO 165
<211> LENGTH: 61
<212> TYPE: PRT
<213> ORGANISM: Artificial Sequence
<220> FEATURE:
<223> OTHER INFORMATION: NRG1(S177-Q237) (3F2)

<400> SEQUENCE: 165

Ser His Leu Val Lys Cys Gly Glu Ser His Lys Ser Phe Cys Val Asn
1               5                   10                  15

Gly Gly Glu Cys Phe Met Ile Glu Gly Pro Ser Asn Pro Ser Arg Tyr
            20                  25                  30

Leu Cys Lys Cys Pro Asn Glu Phe Thr Gly Asp Arg Cys Gln Asp Asp
        35                  40                  45

Phe Met Ala Ser Phe Tyr Lys Ala Glu Glu Leu Tyr Gln
    50                  55                  60

<210> SEQ ID NO 166
<211> LENGTH: 61
<212> TYPE: PRT
<213> ORGANISM: Artificial Sequence
<220> FEATURE:
<223> OTHER INFORMATION: NRG1(S177-Q237) (3G3)

<400> SEQUENCE: 166

Ser His Leu Val Lys Cys Gly Glu Arg Glu Lys Thr Phe Cys Val Asn
1               5                   10                  15

Gly Gly Glu Cys Phe Met Ile Glu His Leu Ser Ile Pro Ser Arg Phe

-continued

```
                  20                25                30
```

Leu Cys Lys Cys Pro Asn Glu Phe Thr Gly Asp Arg Cys Gln Glu Asp
        35                40                45

Phe Met Ala Ser Phe Tyr Lys Ala Glu Glu Leu Tyr Gln
    50                55                60

<210> SEQ ID NO 167
<211> LENGTH: 61
<212> TYPE: PRT
<213> ORGANISM: Artificial Sequence
<220> FEATURE:
<223> OTHER INFORMATION: NRG1(S177-Q237) (3G9)

<400> SEQUENCE: 167

Ser His Leu Val Lys Cys Gly Glu Ser His Lys Ser Phe Cys Val Asn
1               5                10                15

Gly Gly Glu Cys Phe Met Val Glu Asp Leu Ser Asn Pro Ser Arg Phe
                20                25                30

Leu Cys Lys Cys Pro Asn Glu Phe Thr Gly Asp Arg Cys Gln Lys Asp
        35                40                45

Phe Met Ala Ser Phe Tyr Lys Ala Glu Glu Leu Tyr Gln
    50                55                60

<210> SEQ ID NO 168
<211> LENGTH: 61
<212> TYPE: PRT
<213> ORGANISM: Artificial Sequence
<220> FEATURE:
<223> OTHER INFORMATION: NRG1(S177-Q237) (3H5)

<400> SEQUENCE: 168

Ser His Leu Val Lys Cys Gly Glu Arg His Lys Ser Phe Cys Val Asn
1               5                10                15

Gly Gly Glu Cys Tyr Val Val Glu Arg Pro Ser Ile Pro Ser Arg Phe
                20                25                30

Leu Cys Lys Cys Pro Asn Glu Phe Thr Gly Asp Arg Cys Gln Lys Asp
        35                40                45

Phe Leu Ala Ser Phe Tyr Lys Ala Glu Glu Leu Tyr Gln
    50                55                60

<210> SEQ ID NO 169
<211> LENGTH: 52
<212> TYPE: PRT
<213> ORGANISM: Artificial Sequence
<220> FEATURE:
<223> OTHER INFORMATION: NRG1(S177-S228) (3H8)

<400> SEQUENCE: 169

Ser His Leu Val Lys Cys Gly Glu Lys His Lys Ser Phe Cys Val Asn
1               5                10                15

Gly Gly Glu Cys Tyr Met Val Glu Gly Ser Ser Ile Pro Ser Arg Tyr
                20                25                30

Leu Cys Lys Cys Pro Asn Glu Phe Thr Gly Asp Arg Cys Gln Glu Asp
        35                40                45

Phe Met Ala Ser
    50

<210> SEQ ID NO 170
<211> LENGTH: 53
<212> TYPE: PRT
<213> ORGANISM: Artificial Sequence
```

-continued

```
<220> FEATURE:
<223> OTHER INFORMATION: NRG1(S177-F229) (3H8)

<400> SEQUENCE: 170

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe
    50

<210> SEQ ID NO 171
<211> LENGTH: 61
<212> TYPE: PRT
<213> ORGANISM: Artificial Sequence
<220> FEATURE:
<223> OTHER INFORMATION: NRG1(S177-Q237) (3H8)

<400> SEQUENCE: 171

Ser His Leu Val Lys Cys Gly Glu Lys His Lys Ser Phe Cys Val Asn
1               5                   10                  15

Gly Gly Glu Cys Tyr Met Val Glu Gly Ser Ser Ile Pro Ser Arg Tyr
            20                  25                  30

Leu Cys Lys Cys Pro Asn Glu Phe Thr Gly Asp Arg Cys Gln Glu Asp
        35                  40                  45

Phe Met Ala Ser Phe Tyr Lys Ala Glu Glu Leu Tyr Gln
    50                  55                  60

<210> SEQ ID NO 172
<211> LENGTH: 61
<212> TYPE: PRT
<213> ORGANISM: Artificial Sequence
<220> FEATURE:
<223> OTHER INFORMATION: NRG1(S177-Q237) (200E)

<400> SEQUENCE: 172

Ser His Leu Val Lys Cys Ala Glu Lys Glu Lys Thr Phe Cys Val Asn
1               5                   10                  15

Gly Gly Glu Cys Phe Met Val Glu Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 173
<211> LENGTH: 61
<212> TYPE: PRT
<213> ORGANISM: Artificial Sequence
<220> FEATURE:
<223> OTHER INFORMATION: NRG1(S177-Q237) (200E_KDF)

<400> SEQUENCE: 173

Ser His Leu Val Lys Cys Ala Glu Lys Glu Lys Thr Phe Cys Val Asn
1               5                   10                  15

Gly Gly Glu Cys Phe Met Val Glu Asp Leu Ser Asn Pro Ser Arg Tyr
            20                  25                  30

Leu Cys Lys Cys Pro Asn Glu Phe Thr Gly Asp Arg Cys Gln Lys Asp
        35                  40                  45
```

Phe Met Ala Ser Phe Tyr Lys Ala Glu Glu Leu Tyr Gln
    50                  55                  60

<210> SEQ ID NO 174
<211> LENGTH: 61
<212> TYPE: PRT
<213> ORGANISM: Artificial Sequence
<220> FEATURE:
<223> OTHER INFORMATION: NRG1(S177-Q237) (FVIEDPSI)

<400> SEQUENCE: 174

Ser His Leu Val Lys Cys Ala Glu Lys Glu Lys Thr Phe Cys Val Asn
1               5                   10                  15

Gly Gly Glu Cys Phe Val Ile Glu Asp Pro Ser Ile Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys Ala Glu Glu Leu Tyr Gln
    50                  55                  60

<210> SEQ ID NO 175
<211> LENGTH: 61
<212> TYPE: PRT
<213> ORGANISM: Artificial Sequence
<220> FEATURE:
<223> OTHER INFORMATION: NRG1(S177-Q237) (v80)

<400> SEQUENCE: 175

Ser His Leu Val Lys Cys Ala Glu Ser His Lys Ser Phe Cys Val Asn
1               5                   10                  15

Gly Gly Glu Cys Phe Val Ile Glu Gly Ser Ser Ile Pro Ser Arg Tyr
            20                  25                  30

Leu Cys Lys Cys Pro Asn Glu Phe Thr Gly Asp Arg Cys Gln Lys Asp
        35                  40                  45

Val Met Ala Ser Phe Tyr Lys Ala Glu Glu Leu Tyr Gln
    50                  55                  60

<210> SEQ ID NO 176
<211> LENGTH: 61
<212> TYPE: PRT
<213> ORGANISM: Artificial Sequence
<220> FEATURE:
<223> OTHER INFORMATION: NRG1(S177-Q237) (v80.3)

<400> SEQUENCE: 176

Ser His Leu Val Lys Cys Ala Glu Arg His Lys Ser Phe Cys Val Asn
1               5                   10                  15

Gly Gly Glu Cys Phe Val Ile Glu Gly Ser Ser Ile Pro Ser Arg Tyr
            20                  25                  30

Leu Cys Lys Cys Pro Asn Glu Phe Thr Gly Asp Arg Cys Glu Lys Asp
        35                  40                  45

Val Met Ala Ser Phe Tyr Lys Ala Glu Glu Leu Tyr Gln
    50                  55                  60

<210> SEQ ID NO 177
<211> LENGTH: 53
<212> TYPE: PRT
<213> ORGANISM: Artificial Sequence
<220> FEATURE:
<223> OTHER INFORMATION: Neuregulin variant
<220> FEATURE:
<221> NAME/KEY: misc_feature

```
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (21)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (46)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid

<400> SEQUENCE: 177

Ser His Leu Val Lys Cys Xaa Glu Xaa Xaa Lys Xaa Phe Cys Val Asn
1               5                   10                  15

Gly Gly Glu Cys Xaa Xaa Xaa Xaa Xaa Xaa Ser Xaa Pro Ser Arg Xaa
            20                  25                  30

Leu Cys Lys Cys Pro Asn Glu Phe Thr Gly Asp Arg Cys Xaa Xaa Xaa
        35                  40                  45

Xaa Xaa Ala Ser Xaa
    50

<210> SEQ ID NO 178
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 178

Phe Met Ile Glu Asp Ser
1               5

<210> SEQ ID NO 179
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 179

Phe Met Ile Glu Gly Pro
1               5

<210> SEQ ID NO 180
<211> LENGTH: 6
<212> TYPE: PRT
<213> ORGANISM: Artificial Sequence
<220> FEATURE:
<223> OTHER INFORMATION: Neuregulin variant motif 197-202
```

```
<400> SEQUENCE: 180

Phe Met Ile Glu His Leu
1               5

<210> SEQ ID NO 181
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 181

Phe Met Val Glu Asp Leu
1               5

<210> SEQ ID NO 182
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 182

Phe Met Val Glu Arg Ser
1               5

<210> SEQ ID NO 183
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 183

Phe Met Val Lys Arg Pro
1               5

<210> SEQ ID NO 184
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 184

Phe Val Ile Glu Asp Pro
1               5

<210> SEQ ID NO 185
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 185

Phe Val Ile Glu Gly Ser
1               5

<210> SEQ ID NO 186
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 186
```

-continued

```
Phe Val Val Glu Gly Leu
1               5

<210> SEQ ID NO 187
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 187

Tyr Met Ile Glu Asp Leu
1               5

<210> SEQ ID NO 188
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 188

Tyr Met Ile Glu Gly Leu
1               5

<210> SEQ ID NO 189
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 189

Tyr Met Ile Glu His Pro
1               5

<210> SEQ ID NO 190
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 190

Tyr Met Val Glu Asp Leu
1               5

<210> SEQ ID NO 191
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 191

Tyr Met Val Glu Gly Ser
1               5

<210> SEQ ID NO 192
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 192
```

```
Tyr Met Val Glu Arg Pro
1               5

<210> SEQ ID NO 193
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 193

Tyr Val Ile Glu Asp Ser
1               5

<210> SEQ ID NO 194
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 194

Tyr Val Ile Glu Gly Ser
1               5

<210> SEQ ID NO 195
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 195

Tyr Val Ile Glu His Leu
1               5

<210> SEQ ID NO 196
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 196

Tyr Val Val Glu Asp Leu
1               5

<210> SEQ ID NO 197
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 197

Tyr Val Val Glu His Ser
1               5

<210> SEQ ID NO 198
<211> LENGTH: 6
<212> TYPE: PRT
<213> ORGANISM: Artificial Sequence
<220> FEATURE:
<223> OTHER INFORMATION: Neuregulin variant motif 197-202

<400> SEQUENCE: 198

Tyr Val Val Glu Arg Pro
```

```
1               5

<210> SEQ ID NO 199
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 199

Glu Lys Asp Val Met
1               5

<210> SEQ ID NO 200
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 200

Gln Ala Pro His Ile
1               5

<210> SEQ ID NO 201
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 201

Gln Asp Asp Phe Met
1               5

<210> SEQ ID NO 202
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 202

Gln Asp Phe Phe Leu
1               5

<210> SEQ ID NO 203
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 203

Gln Asp Phe Phe Met
1               5

<210> SEQ ID NO 204
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 204

Gln Asp Val Phe Leu
1               5
```

```
<210> SEQ ID NO 205
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 205

Gln Asp Val Phe Met
1               5

<210> SEQ ID NO 206
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 206

Gln Glu Asp Phe Met
1               5

<210> SEQ ID NO 207
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 207

Gln Glu Thr Gln Ile
1               5

<210> SEQ ID NO 208
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 208

Gln Lys Asp Phe Leu
1               5

<210> SEQ ID NO 209
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 209

Gln Lys Asp Phe Met
1               5

<210> SEQ ID NO 210
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 210

Gln Lys Asp Val Met
1               5
```

```
<210> SEQ ID NO 211
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 211

Gln Lys Phe Phe Leu
1               5

<210> SEQ ID NO 212
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 212

Gln Lys Phe Phe Met
1               5

<210> SEQ ID NO 213
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 213

Gln Lys Leu Asp Ile
1               5

<210> SEQ ID NO 214
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 214

Gln Lys Thr Ser Leu
1               5

<210> SEQ ID NO 215
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 215

Gln Lys Val Phe Leu
1               5

<210> SEQ ID NO 216
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 216

Gln Lys Val Phe Met
1               5
```

-continued

```
<210> SEQ ID NO 217
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 217

Gln Lys Val Val Met
1               5

<210> SEQ ID NO 218
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 218

Gln Asn Asp Phe Leu
1               5

<210> SEQ ID NO 219
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 219

Gln Asn Asp Phe Met
1               5

<210> SEQ ID NO 220
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 220

Gln Asn Val Phe Leu
1               5

<210> SEQ ID NO 221
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 221

Gln Asn Val Phe Met
1               5

<210> SEQ ID NO 222
<211> LENGTH: 5
<212> TYPE: PRT
<213> ORGANISM: Homo sapiens

<400> SEQUENCE: 222

Gln Asn Tyr Val Met
1               5

<210> SEQ ID NO 223
<211> LENGTH: 5
<212> TYPE: PRT
```

-continued

```
<213> ORGANISM: Artificial Sequence
<220> FEATURE:
<223> OTHER INFORMATION: Neuregulin variant motif 222-226

<400> SEQUENCE: 223

Gln Gln Ser Phe Pro
1               5

<210> SEQ ID NO 224
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 224

Gln Ser Ala Leu Thr
1               5

<210> SEQ ID NO 225
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 225

Gln Ser Ser Glu Leu
1               5

<210> SEQ ID NO 226
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 226

Gln Ser Thr Arg Val
1               5

<210> SEQ ID NO 227
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 227

Gln Thr Ser Leu Leu
1               5

<210> SEQ ID NO 228
<211> LENGTH: 5
<212> TYPE: PRT
<213> ORGANISM: Artificial Sequence
<220> FEATURE:
<223> OTHER INFORMATION: Neuregulin variant motif 222-226

<400> SEQUENCE: 228

Gln Val Thr Arg Leu
1               5

<210> SEQ ID NO 229
<211> LENGTH: 9
<212> TYPE: PRT
<213> ORGANISM: Homo sapiens
```

<400> SEQUENCE: 229

Phe Tyr Lys Ala Glu Glu Leu Tyr Gln
1               5

<210> SEQ ID NO 230
<211> LENGTH: 52
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (21)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (46)..(50)
<223> OTHER INFORMATION: Xaa can be any naturally occurring amino acid

<400> SEQUENCE: 230

Ser His Leu Val Lys Cys Xaa Glu Xaa Xaa Lys Xaa Phe Cys Val Asn
1               5                   10                  15

Gly Gly Glu Cys Xaa Xaa Xaa Xaa Xaa Xaa Ser Xaa Pro Ser Arg Xaa
            20                  25                  30

Leu Cys Lys Cys Pro Asn Glu Phe Thr Gly Asp Arg Cys Xaa Xaa Xaa
            35                  40                  45

Xaa Xaa Ala Ser
        50

<210> SEQ ID NO 231
<211> LENGTH: 61
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (21)..(26)
<223> OTHER INFORMATION: Xaa can be any naturally occurring amino acid -continued

```
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (46)..(50)
<223> OTHER INFORMATION: Xaa can be any naturally occurring amino acid

<400> SEQUENCE: 231

Ser His Leu Val Lys Cys Xaa Glu Xaa Xaa Lys Xaa Phe Cys Val Asn
1               5                   10                  15

Gly Gly Glu Cys Xaa Xaa Xaa Xaa Xaa Xaa Ser Xaa Pro Ser Arg Xaa
            20                  25                  30

Leu Cys Lys Cys Pro Asn Glu Phe Thr Gly Asp Arg Cys Xaa Xaa Xaa
        35                  40                  45

Xaa Xaa Ala Ser Phe Tyr Lys Ala Glu Glu Leu Tyr Gln
    50                  55                  60
```

ENGINEERED NRG-1 VARIANTS WITH IMPROVED SELECTIVITY TOWARD ErbB4 BUT NOT AGAINST ErbB3

CROSS-REFERENCE TO RELATED APPLICATIONS

This application claims the benefit of U.S. Provisional Application No. 63/209,248 filed Jun. 10, 2021, which is-incorporated by reference herein in its entirety.

FIELD OF THE INVENTION

The present invention relates to engineered neuregulin-1 variants that selectively activate ErbB4 receptors but do not activate, or weakly activate, ErbB3 receptors. The invention also provides methods for using such neuregulin variants in the treatment of heart failure.

SEQUENCE LISTING

This application contains a sequence listing, as a separate part of the disclosure, in computer-readable form (Filename: A-2828-US02-SEC_SubSeqListing.txt, created Dec. 16, 2024, which is 336 KB in size), and which is incorporated by reference in its entirety.

BACKGROUND OF THE INVENTION

The epidermal growth factor receptor family, which comprises four members EGFR, ErbB2, ErbB3 and ErbB4, has been demonstrated to play an important role in multiple cellular functions, including cell growth, differentiation and survival. They are protein tyrosine kinase receptors, consisting of an extracellular ligand-binding domain, transmembrane domain and cytoplasmic tyrosine kinase domain. Multiple receptor ligands have been identified which mediate receptor homo- or hetero-dimerization upon binding. The specific receptor association results in different patterns of phosphorylation, complex signaling cascades and multiple biological functions, including cellular proliferation, prevention of apoptosis and promotion of tumor cell mobility, adhesion and invasion. Exemplary cells that express ErbB receptors include glial cells, glioblastoma cells, Schwann cells, hepatocytes, epithelial cells, and muscle cells. Glial cells are derived from the central nervous system and include oligodendrocytes and astrocytes. Muscle cells expressing ErbB receptors include muscle cell precursors (myoblasts) as well as the more specialized skeletal, cardiac, and smooth muscle cells.

Neuregulin, also known as heregulin, glial growth factor (GGF) and new differentiation factor (NDF), is an important growth factor, particularly for the heart and nervous system. Over 15 distinct isoforms of neuregulin-1 (NRG-1) have been identified and divided into two groups, known as alpha- and beta-types, on the basis of differences in the sequence of their essential EGF-like domains. Neuregulin-1 is a ligand of ErbB3 and ErbB4 receptors. It has been shown that the EGF-like domains of neuregulin-1, ranging in size from 50 to 64-amino acids, are sufficient to bind to and activate these receptors. See, e.g., Jones et al., 1999, FEBS Lett. 26:447: 227-231. Previous studies have shown that neuregulin-lp (NRG-1β) can bind directly to ErbB3 and ErbB4 with high affinity. The orphan receptor, ErbB2, holds a preactivated conformation to facilitate hetero-dimerization with ErbB3 or ErbB4 with approximately 100-fold higher affinity than ErbB3 and ErbB4 homodimers. The heterometric receptors act in distinct cell types: ErbB2/ErbB3 in the peripheral nervous system and ErbB2/ErbB4 in the heart. Research in neural development has indicated that the formation of the sympathetic nervous system requires an intact NRG-1β, ErbB2 and ErbB3 signaling system. ErbB2/ErbB4 receptor activation promotes myocardial cell growth and survival. Targeted disruption of the NRG-1β, or ErbB2 or ErbB4 led to embryonic lethality due to cardiac development defects. Recent studies also highlighted the roles of NRG-1β, ErbB2 and ErbB4 in the cardiovascular development as well as in the maintenance of adult normal heart function.

Activation of ErbB4 by recombinant NRG-1 is a potential treatment option for heart failure because neuregulin stimulated ErbB2/ErbB4 heterodimerization is critical for myocardium function in early heart development and also prevents severe dysfunction of the adult heart. The short-term administration of a recombinant NRG-1β EGF domain significantly improves or protects against deterioration in myocardial performance in three distinct animal models of heart failure. More importantly, NRG-1β significantly prolongs survival of heart failure animals. See, e.g., De Keulenaer et al., 2019, Circulation: Heart Failure 12:e006288. These effects make NRG-1P promising as a broad spectrum therapeutic or lead compound for heart failure due to a variety of common diseases.

There have been several drug candidates based on NRG-1 that have advanced in clinical trials for the treatment of heart disease through binding of ErbB4. However, binding through ErbB3 is thought to promote development or progression of certain cancers and also may cause gastrointestinal toxicity.

A 61-mer peptide (from S177 to Q237 of wild-type hNRG-1) has shown potent activity against both ErbB4 and ErbB3. See Liu et al., 2006, J Amer Coll Cardiol 48:1438-1447; and U.S. Pat. No. 7,226,907. See also International Patent Application Publication Nos. WO2010060265; WO2009007332; WO2009033373; WO2006030241; Jay et al., 2013; Circulation 128:152-161; and Wali et al., 2014, Mol Cancer Res 12:1140-1155. U.S. Pat. Nos. 7,115,554 and 7,063,961 describes heregulin β1 variants that show increased affinity for both ErbB3 and ErbB4 receptors. U.S. Patent Application Publication No. 2007/0213264 describes neuregulin-1β variants that show enhanced or decreased binding affinity to ErbB3 and/or ErbB4.

However, there is still a need for NRG-1 variants which show high selectivity for ErbB4 over ErbB3 for therapeutic use in heart failure.

SUMMARY OF THE INVENTION

The present disclosure provides polypeptide variants of neuregulin-1β that are selective against ErbB4 and not ErbB3 as compared to a wild-type sequence. In certain embodiments, the variant has increased binding affinity to ErbB4 and decreased binding affinity to ErbB3 compared to a wild type sequence. In certain embodiments, the variant has increased binding affinity to ErbB4 and similar binding affinity to ErbB3 compared to a wild type sequence. In certain embodiments, the variant has similar binding affinity to ErbB4 and decreased binding affinity to ErbB3 compared to a wild-type sequence.

The disclosure also includes NRG-1 variants that have greater specificity for the ErbB4 receptor, relative to the ErbB3 receptor, than the NRG-1 from which the NRG-1 variant is derived. In certain embodiments, the NRG-1 variant has a binding affinity for ErbB4 that is 2×, 3×, 4× greater than for ErbB3.

The disclosure also includes NRG-1 variants that have greater selectivity for the ErbB4 receptor compared to the ErbB3 receptor. In certain embodiments, the NRG-1 variant has a selectivity for ErbB4/ErbB3 greater than equal to 1000 or greater than equal to 10000.

In certain embodiments, the NRG-1 variant has agonist activity that is at least 50%, 60%, 70%, or 80% of the corresponding wild-type sequence.

In one embodiment, the disclosure provides a polypeptide variant comprising an amino acid sequence of the formula:

$$\text{(SEQ ID NO: 177)}$$
$$\text{SHLVKCX}_{183}\text{EX}_{185}\text{X}_{186}\text{KX}_{188}\text{FCVNGGECX}_{197}\text{X}_{198}\text{X}_{199}\text{X}_{200}$$
$$\text{X}_{201}\text{X}_{202}\text{SX}_{204}\text{PSRX}_{208}\text{LCKCPNEFTGDRCX}_{222}\text{X}_{223}\text{X}_{224}$$
$$\text{X}_{225}\text{X}_{226}\text{ASX}_{229}$$

wherein $X_{183}$ is A or G;

$X_{185}X_{186}$ is KD, KE, KH, ND, NE, NH, RD, RE, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMIEHL (SEQ ID NO:180), FMVEDL (SEQ ID NO:181), FMVERS (SEQ ID NO:182), FMVKRP (SEQ ID NO:183), FVIEDP (SEQ ID NO:184), FVIEGS (SEQ ID NO:185), FVVEGL (SEQ ID NO:186), YMIEDL (SEQ ID NO:187), YMIEGL (SEQ ID NO:188), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEDL (SEQ ID NO:196), YVVEHS (SEQ ID NO:197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QDDFM (SEQ ID NO:201), QDFFL (SEQ ID NO:202), QDFFM (SEQ ID NO:203), QDVFL (SEQ ID NO:204), QDVFM (SEQ ID NO:205), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215), QKVFM (SEQ ID NO:216), QKVVM (SEQ ID NO:217), QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is absent, F or FYKAEELYQ (SEQ ID NO:229).

When $X_{229}$ is absent, the formula can be represented by: SHLVKCX$_{183}$EX$_{185}$X$_{186}$KX$_{188}$FCVNGGECX$_{197}$X$_{198}$X$_{199}$ X$_{200}$X$_{201}$X$_{202}$SX$_{204}$PSRX$_{205}$ LCKCPNE FTGDRCX$_{222}$X$_{223}$X$_{224}$X$_{225}$X$_{226}$AS (SEQ ID NO:230).

When $X_{229}$ is FYKAEELYQ (SEQ ID NO:229), the formula can be represented by: SHLVKCX$_{183}$EX$_{185}$X$_{186}$KX$_{188}$FCVNGGECX$_{197}$X$_{198}$X$_{199}$ X$_{200}$X$_{201}$X$_{202}$SX$_{204}$PSRX$_{205}$ LCKCPNE FTGDRCX$_{222}$X$_{223}$X$_{224}$X$_{225}$X$_{226}$ASFYKAEELYQ (SEQ ID NO:231).

In an aspect of this embodiment, the polypeptide variant comprises an amino acid sequence of any of SEQ ID Nos: 114 to 176.

In one embodiment, the disclosure provides a polypeptide variant, wherein $X_{183}$ is A or G;

$X_{185}X_{186}$ is KD, KE, KH, ND, NH, RD, RE, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMIEHL (SEQ ID NO:180), FMVEDL (SEQ ID NO:181), FMVERS (SEQ ID NO:182), FMVKRP (SEQ ID NO:183), FVIEDP (SEQ ID NO:184), FVIEGS (SEQ ID NO:185), YMIEDL (SEQ ID NO:187), YMIEGL (SEQ ID NO:188), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEHS (SEQ ID NO:197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QDFFL (SEQ ID NO:202), QDFFM (SEQ ID NO:203), QDVFL (SEQ ID NO:204), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215), QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is F or FYKAEELYQ (SEQ ID NO:229).

In one aspect of this embodiment, the polypeptide variant comprises an amino acid sequence of any of SEQ ID Nos: 114, 115, 117 to 124, 126 to 135, 138, 139, 144 to 147, 149 to 156, 160 to 168, or 171 to 176.

In one embodiment, the disclosure provides a polypeptide variant, wherein $X_{183}$ is A or G;

$X_{185}$ is KE, KH, ND, RD, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMVEDL (SEQ ID NO:181), FMVKRP (SEQ ID NO:183), FVIEDP (SEQ ID NO:184), FVIEGS (SEQ ID NO:185), YMIEDL (SEQ ID NO:187), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEHS (SEQ ID NO: 197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215),

QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is F or FYKAEELYQ (SEQ ID NO:229).

In one aspect of this embodiment, the polypeptide variant comprises an amino acid sequence of any of SEQ ID Nos: 117 to 124, 126 to 135, 144 to 147, 149 to 152, 154 to 156, 163, 167, 168, or 171 to 176.

In one embodiment, the disclosure provides a polypeptide variant wherein $X_{183}$ is A or G;

$X_{185}X_{186}$ is KH, ND, RD, RH, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMVEDL (SEQ ID NO:181), FVIEDP (SEQ ID NO:184), YMIEDL (SEQ ID NO:187), YMVEGS (SEQ ID NO:191), YVIEGS (SEQ ID NO: 194), YVIEHL (SEQ ID NO:195), or YVVERP (SEQ ID NO:198);

$X_{204}$ is I or N;

$X_{205}$ is F or Y;

$X_{222}X_{223}X_{224}X_{225}X_{226}$ is QAPHI (SEQ ID NO:200), QEDFM (SEQ ID NO:206), QETQI (SEQ ID NO:207), QKDFL (SEQ ID NO:208), QKDFM (SEQ ID NO:209), QKTSL (SEQ ID NO:214), QNDFL (SEQ ID NO:218), QNDFM (SEQ ID NO:219), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is F or FYKAEELYQ (SEQ ID NO:229).

In one aspect of this embodiment, the polypeptide variant comprises an amino acid sequence of any of SEQ ID Nos: 117 to 124, 126, 128 to 135, 146, 147, 150, 151, 163, 167, 168, or 171.

In another aspect of this embodiment, the polypeptide variant comprises an amino acid sequence of any of SEQ ID Nos: 117, 118, 119, 120, 122, 123, 124, 126, 128, 129, 130, 131, 133, or 135.

In any of the embodiments, the polypeptide variant further comprises a second amino acid sequence to act as a signal sequence, increase the half-life, or aid in purification. In certain aspects, the polypeptide variant can be fused to an amino acid sequence to prolong its half-life. In one aspect, the amino acid sequence is an Fc region. In one aspect, the amino acid sequence is fused to the C-terminus of the polypeptide variant. In one aspect, the amino acid sequence is fused to the N-terminus of the polypeptide variant. In certain aspects, the amino acid sequence is fused to the polypeptide variant via a linker. In certain aspects, the polypeptide variant can be fused to His tag to aid in purification. In one aspect, the His tag is fused to the C-terminus of the polypeptide variant. In one aspect, the His tag is fused to the N-terminus of the polypeptide variant.

In other aspects, the polypeptide variant comprises an amino acid sequence of any of SEQ ID Nos: 1 to 24, 29 to 54, 56 to 67, 69 to 80, 82 to 111. In other aspects, the polypeptide variant comprises an amino acid sequence of any of SEQ ID Nos: 1 to 15, 19, 20, 22, 23, 29 to 34, 37, 38, 43 to 54, 56 to 59, 61 to 67, 69 to 80, 82 to 85, 87 to 93, or 97 to 111. In one aspect, the polypeptide variant comprises an amino acid sequence of any of SEQ ID Nos: 3, 4, 6, 9, 11 to 13, 19, 22, 31 to 34, 43 to 48, 52, 54, 56 to 59, 61 to 63, 65 to 67, 71, 72, 75 to 80, 84, 85, 88, 100, or 104 to 106. In one aspect, the polypeptide variant comprises an amino acid sequence of any of SEQ ID Nos: 3, 4, 6, 9, 11 to 13, 19, 22, 31 to 34, 43 to 48, 52, 54, 56 to 59, 61 to 63, 65 to 67, 71, 72, 75 to 80, 84, 85, 88, 100, or 104 to 106. In one aspect, the polypeptide variant comprises an amino acid sequence of SEQ ID NO:4, 11, 13, 32, 34, 45, 46, 48, 52, 72, 75, 76, 77, 78, 79, or 80. In one aspect, the polypeptide variant comprises an amino acid sequence of SEQ ID NO:56, 57, 58, 59, 61, 62, 63, 65, 66 or 67.

The disclosure also provides a pharmaceutical composition comprising the polypeptide variant described herein, and a pharmaceutically acceptable carrier.

The disclosure also provides a method of treating a cardiovascular disease or condition in a subject in need thereof, the method comprising administering a therapeutically effective amount of the polypeptide variant, or the pharmaceutical composition. In certain aspects of this embodiment, the cardiovascular disease or condition is heart failure, myocardial infarction, dilated cardiomyopathy, myocarditis, or cardiac toxicity. In certain aspects, the subject is a human.

The disclosure also provides the aforementioned polypeptide variants for use in treating a cardiovascular disease or condition or for the preparation of a medicament for treating a cardiovascular disease or condition. In one embodiment, the disclosure provides a neuregulin polypeptide variant for use in treating a cardiovascular disease or condition. In another embodiment, the disclosure provides the use of a neuregulin polypeptide for the preparation of a medicament for treating a cardiovascular disease or condition.

DETAILED DESCRIPTION OF THE INVENTION

Figure 1A:
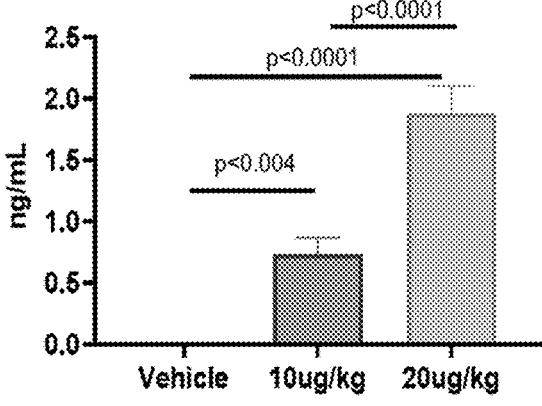
FIGS. 1A-C show cardiac function assessment 1-week after ErbB4 agonist dosing. GraphPad One-way ANOVA was used to assess the statistical significance among groups. A) Terminal serum exposures. B) Cardiac function by ejection fraction (EF). C) Heart rate (HR) during echocardiography.

The present invention is based in part on the discovery that neuregulin variants can be designed that are highly selective for ErbB4 while having reduced or no binding affinity for ErbB3. Such variants are candidates for therapeutics for heart related diseases while minimizing cross-reactivity against other cell types. This invention arose, in part, from an effort to improve the efficacy of heart failure drugs. Accordingly, the disclosure is also directed to treating subjects with or at risk for development of heart disease and related conditions, e.g., heart failure.

Definitions

While the terminology used in this application is standard within the art, definitions of certain terms are provided herein to assure clarity and definiteness in the meaning of the claims. Units, prefixes, and symbols may be denoted in their SI (International System of Units) accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990).

As used herein, the terms "a" and "an" mean one or more unless specifically indicated otherwise. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

All documents, or portions of documents, cited in this application, including but not limited to patents, patent applications, articles, books, and treatises, are hereby expressly incorporated by reference. What is described in an embodiment of the invention can be combined with other embodiments of the invention.

As used herein, the terms "neuregulin-1" or "NRG-1" or "neuregulin" refer to proteins or peptides that can bind and activate ErbB2/ErbB4 or ErbB2/ErbB3 heterodimers protein kinases, such as all neuregulin isoforms, neuregulin EGF domain alone, neuregulin mutants, and any kind of neuregulin-like gene products that also activate the above receptors. Neuregulin also includes NRG-1, NRG-2, NRG-3, and NRG-4. These proteins and polypeptides can activate the above ErbB receptors and modulate their biological reactions, e.g., stimulate breast cancer cell differentiation and milk protein secretion; induce the differentiation of neural crest cell into Schwann cell; stimulate acetylcholine synthesis in skeletal muscle cell; and improve cardiomyocyte survival and DNA synthesis. Neuregulin also includes those variants with conservative amino acid substitutions that do not substantially alter their biological activity. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987. The Benjamin/Cummings Pub. Co. p. 224). The phrase "neuregulin protein" encompasses the full-length neuregulin protein as well as a neuregulin peptide (e.g., a truncated form of the full-length neuregulin protein. Neuregulin nucleic acid encompasses neuregulin nucleic acid and neuregulin oligonucleotide.

As used herein, "neuregulin variant" refers to neuregulin that has a modified sequence that alters or improves the selectivity of the neuregulin to ErbB4 and/or reduces selectivity of the neuregulin to ErbB3.

As used herein, the terms, "epidermal growth factor-like domain" or "EGF-like domain refers to a polypeptide motif encoded by the neuregulin gene that binds to and activates ErbB2, ErbB3, ErbB4, or combinations thereof, and bears a structural similarity to the EGF receptor-binding domain as disclosed in International Patent Application Publication Nos. WO00/64400 and WO 97/09425, Holmes et al., 1992, Science, 256:1205-1210; U.S.

U.S. Pat. Nos. 5,530,109 and 5,716,930; Hijazi et al., 1998, Int. J. Oncol., 13:1061-1067; Chang et al., 1997, Nature, 387:509-512; Carraway et al., 1997, Nature, 387:512-516; Higashiyama et al., 1997, J. Bio Chem., 122:675-680. EGF-like domains may be derived from NRG-1, NRG-2, NRG-3, or NRF-4. EGF-like domains may be C or B subtype.

As used herein, the terms "ErbB2", "ErbB2 (HER2)", "HER2" refer to the same protein (or the same gene when in reference thereto) and are used interchangeably herein. ErbB2 (erb-b2 receptor tyrosine kinase 2) is also known in the art as NEU, NGL, TKR1, CD340, HER-2, MLN 19 and HER-2/neu.

As used herein, the terms "ErbB3", "ErbB3 (HER3)", "HER3" refer to the same protein (or the same gene when in reference thereto) and are used interchangeably herein. ErbB3 (erb-b2 receptor tyrosine kinase 3) is also known in the art as FERLK, LCCS2, ErbB-3, c-erbB3, erbB3-S, MDA-BF-1, c-erbB-3, $\beta$180-ErbB3, p45-sErbB3 and p85-sErbB3.

As used herein, the terms "ErbB4", "ErbB4 (HER4)", "HER4" refer to the same protein (or the same gene when in reference thereto) and are used interchangeably herein. ErbB4 (erb-b2 receptor tyrosine kinase 4) is also known in the art as ALS19 and $\beta$180erbB4.

As used herein, the term "effective amount" or "therapeutically effective amount" means a dosage or amount sufficient to produce a desired result. The desired result may comprise an objective or subjective improvement in the subject of the dosage or amount (e.g., long-term survival, improved cardiac function, effective prevention of a disease state, etc.).

As used herein, the term "ejection fraction" refers to ejection fraction (EF), a measurement, typically expressed as a percentage, of how much blood the left ventricle pumps out with each contraction. For example, an ejection fraction of 50 percent means that 50 percent of the total amount of blood in the left ventricle is pushed out with each heartbeat.

As used herein, the term "heart failure" is meant as an abnormality of cardiac function where the output of the heart does not meet the requirements of metabolizing tissues. Heart failure includes a wide range of disease states such as congestive heart failure, myocardial infarction, tachyarrhythmia, familial hypertrophic cardiomyopathy, ischaemic heart disease, idiopathic dilated cardiomyopathy, and myocarditis. The heart failure can be caused by any number of factors, including ischaemic, congenital, rheumatic, or idiopathic forms. Chronic cardiac hypertrophy is a significant disease state which is a precursor to congestive heart failure and cardiac arrest.

As used herein, the terms "polypeptide" and "protein" can be used interchangeably herein to refer to a polymer of amino acid residues. The terms also apply to amino acid polymers in which one or more amino acid residues is an analog or mimetic of a corresponding naturally occurring amino acid, as well as to naturally occurring amino acid polymers. The terms can also encompass amino acid polymers that have been modified, e.g., by the addition of carbohydrate residues to form glycoproteins, or phosphorylated.

Polypeptides and proteins can be produced by a naturally-occurring and non-recombinant cell, or polypeptides and proteins can be produced by a genetically-engineered or recombinant cell. Polypeptides and proteins can also be produced by synthetic means. Polypeptides and proteins can comprise molecules having the amino acid sequence of a native protein, or molecules having deletions from, additions to, and/or substitutions of one or more amino acids of the native sequence.

The terms "polypeptide" and "protein" encompass molecules comprising only naturally occurring amino acids, as well as molecules that comprise non-naturally occurring amino acids. Examples of non-naturally occurring amino acids (which can be substituted for naturally-occurring amino acids found in any sequence disclosed herein, as desired) include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

A non-limiting list of examples of non-naturally occurring amino acids that can be inserted into a protein or polypeptide sequence or substituted for a wild-type residue in a protein or polypeptide sequence include $-amino acids, homoamino acids, cyclic amino acids and amino acids with derivatized side chains. Examples include (in the L-form or D-form; abbreviated as in parentheses): citrulline (Cit), homocitrulline (hCit), Nα-methylcitrulline (NMeCit), Nα-methylhomocitrulline (Nα-MeHoCit), ornithine (Orn), Nα-Methylornithine (Nα-MeOrn or NMeOrn), sarcosine (Sar), homolysine (hLys or hK), homoarginine (hArg or hR), homoglutamine (hQ), Nα-methylarginine (NMeR), Nα-methylleucine (Nα-MeL or NMeL), N-methylhomolysine (NMeHoK), Nα-methylglutamine (NMeQ), norleucine (Nle), norvaline (Nva), 1,2,3,4-tetrahydroisoquinoline (Tic), Octahydroindole-2-carboxylic acid (Oic), 3-(1-naphthyl) alanine (1-Nal), 3-(2-naphthyl)alanine (2-Nal), 1,2,3,4-tetrahydroisoquinoline (Tic), 2-indanylglycine (IgI), para-iodophenylalanine (pI-Phe), para-aminophenylalanine (4AmP or 4-Amino-Phe), 4-guanidino phenylalanine (Guf), glycyllysine (abbreviated "K(Ne-glycyl)" or "K(glycyl)" or "K(gly)"), nitrophenylalanine (nitrophe), aminophenylalanine (aminophe or Amino-Phe), benzylphenylalanine (benzylphe), γ-carboxyglutamic acid (γ-carboxyglu), hydroxyproline (hydroxypro), p-carboxyl-phenylalanine (Cpa), α-aminoadipic acid (Aad), Nα-methyl valine (NMeVal), N-α-methyl leucine (NMeLeu), Nα-methylnorleucine (NMeNle), cyclopentylglycine (Cpg), cyclohexylglycine (Chg), acetylarginine (acetylarg), α,β-diaminopropionoic acid (Dpr), a, γ-diaminobutyric acid (Dab), diaminopropionic acid (Dap), cyclohexylalanine (Cha), 4-methyl-phenylalanine (MePhe), β,β-diphenyl-alanine (BiPhA), aminobutyric acid (Abu), 4-phenyl-phenylalanine (or biphenylalanine; 4Bip), α-amino-isobutyric acid (Aib), beta-alanine, beta-aminopropionic acid, piperidinic acid, aminocaprioic acid, aminoheptanoic acid, aminopimelic acid, desmosine, diaminopimelic acid, N-ethylglycine, N-ethylaspargine, hydroxylysine, allo-hydroxylysine, isodesmosine, allo-isoleucine, N-methylglycine, N-methylisoleucine, N-methylvaline, 4-hydroxyproline (Hyp), γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-methylarginine, 4-Amino-O-Phthalic Acid (4APA), and other similar amino acids, and derivatized forms of any of those specifically listed.

An "Fc" region, as the term is used herein, can comprise two heavy chain fragments comprising the $C_H2$ and $C_H3$ domains of an antibody. The two heavy chain fragments are held together by two or more disulfide bonds and by hydrophobic interactions of the $C_H3$ domains. Proteins of interest comprising an Fc region, including antigen binding proteins and Fc fusion proteins, form another aspect of the instant disclosure.

NRG-1β Variants

The present disclosure provides polypeptide variants of NRG-1 that are selective for ErbB4. A neuregulin variant as disclosed herein has an amino acid sequence not found in nature in which one or more wildtype amino acid residues in a native neuregulin is substituted with different amino acid residues. At least one substitution is non-conservative so as to alter function, e.g., improve selectivity to ErbB4.

A functional human NRG-1 fragment which corresponds to amino acids 177-237 of human NRG-1 and contains the EGF-like domain has the amino acid sequence

```
                                    (SEQ ID NO: 112)
SHLVKCAEKEKTFCVNGGECFMVKDLSNPSRYLCKCPNEFTG

DRCQNYVMASFYKAEELYQ
```

In some embodiments, a neuregulin fragment containing the EGF-like domain refers to amino acid residues 177-226, 177-228, 177-229, 177-237, or 177-240 of NRG-1 (SEQ ID NO: 112).

Representative neuregulin variants comprising a modified neuregulin sequence and one or more of linkers, Fc sequences and His tags are shown in Table 1 below.

TABLE 1

| Name | Sequences | SEQ ID NO |
|---|---|---|
| huNRG1 (S177-F229) (NRGE1 C):: 3x (G4Q):: huFcSEFL2 (Pb) | SHLVKCGEKHKSFCVNGGECFMIEG PSNPSRYLCKCPNEFTGDRCQEDFM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 1 |
| huNRG1 (S177-F229) (NRGE1 C):: 1KmodT482V, M493L):: huFcSEFL2 (Pb) | SHLVKCGEKHKSFCVNGGECFMIEG PSNPSRYLCKCPNEFTGDRCQEDFM ASFGSGSATGGSGSVASSGSGSATH LDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | 2 |
| huNRG1 (S177-F229) (NRGE1 C):: (G4A)2:G4:: huFcSEF L2 (Pb) | SHLVKCGEKHKSFCVNGGECFMIEG PSNPSRYLCKCPNEFTGDRCQEDFM ASFGGGGAGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 3 |

TABLE 1-continued

| Name | Sequences | SEQ ID NO |
|---|---|---|
| huNRG1 (S177-F229) (NRGE1 C) ((G4E)2):: G4:: huFCSE FL2 (Pb) | SHLVKCGEKHKSFCVNGGECFMIEG PSNPSRYLCKCPNEFTGDRCQEDFM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 4 |
| huNRG1 (S177-F229) (NRGE1 C):: (G4S)2:: G4:: huFCS EFL2 (Pb) | SHLVKCGEKHKSFCVNGGECFMIEG PSNPSRYLCKCPNEFTGDRCQEDFM ASFGGGGSGGGGSGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 5 |
| huNRG1 (S177-F229) (NRGE1 C) (G4E):: G4S:: G4:: huF cSEFL2 (Pb) | SHLVKCGEKHKSFCVNGGECFMIEG PSNPSRYLCKCPNEFTGDRCQEDFM ASFGGGGEGGGGSGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 6 |
| huNRG1 (S177-F229) (NRGE1 C) (NRGmod):: G4:: huFcSE FL2 (Pb) | SHLVKCGEKHKSFCVNGGECFMIEG PSNPSRYLCKCPNEFTGDRCQEDFM ASFTUXAEELYQGGGGDKTHTCPPC PAPELLGGPSVFLFPPKPKDTLMIS RTPEVTCVVVDVSHEDPEVKFNWYV DGVEVHNAKTKPCEEQYGSTYRCVS VLTVLHQDWLNGKEYKCKVSNKALP APIEKTISKAKGQPREPQVYTLPPS REEMTKNQVSLTCLVKGFYPSDIAV EWESNGQPENNYKTTPPVLDSDGSF FLYSKLTVDKSRWQQGNVFSCSVMH EALHNHYTQKSLSLSPGK | 7 |
| huNRG1 (S177-F229) (NRGE1 D):: 3x (G4Q):: huFcSEFL2(Pb) | SHLVKCGESHKSFCVNGGECYMVEG SSIPSRYLCKCPNEFTGDRCQEDFM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 8 |
| huNRG1 (S177-F229) (NRGE1 D):: 1KmodT482V, M493L):: huFcSEFL2 (Pb) | SHLVKCGESHKSFCVNGGECYMVEG SSIPSRYLCKCPNEFTGDRCQEDFM ASFGSGSATGGSGSVASSGSGSATH LDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT | 9 |

TABLE 1-continued

| Name | Sequences | SEQ ID NO |
|---|---|---|
|  | PPVLDSDGSFFLYSKLTVDKSRWQQ GNVFSCSVMHEALHNHYTQKSLSLS PGK |  |
| huNRG1 (S177-F229) (NRGE1 D):: (G4A)2:G4:: huFcSEF L2 (Pb) | SHLVKCGESHKSFCVNGGECYMVEG SSIPSRYLCKCPNEFTGDRCQEDFM ASFGGGGAGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 10 |
| huNRG1 (S177-F229) (NRGE1 D) ((G4E)2):: G4:: huFCSE FL2 (Pb) | SHLVKCGESHKSFCVNGGECYMVEG SSIPSRYLCKCPNEFTGDRCQEDFM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 11 |
| huNRG1 (S177-F229) (NRGE1 D):: (G4S)2:: G4:: huFCS EFL2 (Pb) | SHLVKCGESHKSFCVNGGECYMVEG SSIPSRYLCKCPNEFTGDRCQEDFM ASFGGGGSGGGGSGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 12 |
| huNRG1 (S177-F229) (NRGE1 D) (G4E):: G4S:: G4:: huF cSEFL2 (Pb) | SHLVKCGESHKSFCVNGGECYMVEG SSIPSRYLCKCPNEFTGDRCQEDFM ASFGGGGEGGGGSGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 13 |
| huNRG1 (S177-F229) (NRGE1 D) (NRGmod):: G4:: huFcSE FL2 (Pb) | SHLVKCGESHKSFCVNGGECYMVEG SSIPSRYLCKCPNEFTGDRCQEDFM ASFAAAEELYQGGGGDKTHTCPPCP APELLGGPSVFLFPPKPKDTLMISR TPEVTCVVVDVSHEDPEVKFNWYVD GVEVHNAKTKPCEEQYGSTYRCVSV LTVLHQDWLNGKEYKCKVSNKALPA PIEKTISKAKGQPREPQVYTLPPSR EEMTKNQVSLTCLVKGFYPSDIAVE WESNGQPENNYKTTPPVLDSDGSFF LYSKLTVDKSRWQQGNVFSCSVMHE ALHNHYTQKSLSLSPGK | 14 |
| huNRG1 (S177-Q237) (3H8) 3xG4S:: huFcSEFL2 (Pb) | SHLVKCGEKHKSFCVNGGECYMVEG SSIPSRYLCKCPNEFTGDRCQEDFM ASFYKAEELYQGGGGSGGGGSGGGG SDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY | 15 |

TABLE 1-continued

| Name | Sequences | SEQ ID NO |
|---|---|---|
| | KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | |
| huNRG1 (S177-F229) (3H8):: 3x (G4Q):: huFcSEFL2 (Pb) | SHLVKCGEKHKSFCVNGGECMVEG SSIPSRYLCKCPNEFTGDRCQEDFM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 16 |
| huNRG1 (S177-Q237) (3H8):: 3x (G4Q):: huFcSEFL2 (Pb) | SHLVKCGEKHKSFCVNGGECYMVEG SSIPSRYLCKCPNEFTGDRCQEDFM ASFYKAEELYQGGGGQGGGGQGGGG QDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | 17 |
| huNRG1 (S177-S228) (3H8):: 3x (G4Q):: huFcSEFL2 (Pb) | SHLVKCGEKHKSFCVNGGECYMVEG SSIPSRYLCKCPNEFTGDRCQEDFM ASGGGGGQGGGGQGGGGQDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 18 |
| huNRG1 (S177-Q237) (NRGE1 C):: GG:: huFcSEFL2 (Pb) | SHLVKCGEKHKSFCVNGGECFMIEG PSNPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 19 |
| huNRG1 (S177-F229) (NRGE1 C):: 3x (G4Q):: huFcSEFL2 (Pb) | SHLVKCGEKHKSFCVNGGECFMIEG PSNPSRYLCKCPNEFTGDRCQEDFM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 1 |
| huNRG1 (S177-Q237) (NRGE1 | SHLVKCGEKHKSFCVNGGECFMIEG PSNPSRYLCKCPNEFTGDRCQEDFM ASFYKAEELYQGGGGQGGGGQGGGG | 20 |

TABLE 1-continued

| Name | Sequences | SEQ ID NO |
|---|---|---|
| C):: 3x (G4Q):: huFcSEFL2(Pb) | QDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | |
| huNRG1 (S177-S228) (NRGE1 C):: 3x (G4Q):: huFcSEFL2(Pb) | SHLVKCGEKHKSFCVNGGECFMIEG PSNPSRYLCKCPNEFTGDRCQEDFM ASGGGGGQGGGGQGGGGQDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 21 |
| huNRG1 (S177-Q237) (NRGE1 D):: GG:: huFcSEFL2 (Pb) | SHLVKCGESHKSFCVNGGECYMVEG SSIPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 22 |
| huNRG1 (S177-F229) (NRGE1 D):: 3x (G4Q):: huFcSEFL2(Pb) | SHLVKCGESHKSFCVNGGECYMVEG SSIPSRYLCKCPNEFTGDRCQEDFM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 8 |
| huNRG1 (S177-Q237) (NRGE1 D):: 3x (G4Q):: huFcSEFL2(Pb) | SHLVKCGESHKSFCVNGGECYMVEG SSIPSRYLCKCPNEFTGDRCQEDFM ASFYKAEELYQGGGGQGGGGQGGGG QDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | 23 |
| huNRG1 (S177-S228) (NRGE1 D):: 3x (G4Q):: huFcSEFL2(Pb) | SHLVKCGESHKSFCVNGGECYMVEG SSIPSRYLCKCPNEFTGDRCQEDFM ASGGGGGQGGGGQGGGGQDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 24 |

TABLE 1-continued

| Name | Sequences | SEQ ID NO |
|---|---|---|
| huNRG1 (S177-Q237) (wt)::GG:: huFcSEFL2 (Pb) | SHLVKCAEKEKTFCVNGGECFMVKD LSNPSRYLCKCPNEFTGDRCQNYVM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 25 |
| huNRG1 (S177-F229) (wt)::3x (G4Q):: huFcSEFL2 *Pb) | SHLVKCAEKEKTFCVNGGECFMVKD LSNPSRYLCKCPNEFTGDRCQNYVM ASFGGGGQGGGGQGGGGQDKTHTCP PCPAPELLGGPSVFLFPPKPKDTLM ISRTPEVTCVVVDVSHEDPEVKFNW YVDGVEVHNAKTKPCEEQYGSTYRC VSVLTVLHQDWLNGKEYKCKVSNKA LPAPIEKTISKAKGQPREPQVYTLP PSREEMTKNQVSLTCLVKGFYPSDI AVEWESNGQPENNYKTTPPVLDSDG SFFLYSKLTVDKSRWQQGNVFSCSV MHEALHNHYTQKSLSLSPGK | 26 |
| huNRG1 (S177-Q237) (wt)::3x (G4Q):: huFcSEFL2 *Pb) | SHLVKCAEKEKTFCVNGGECFMVKD LSNPSRYLCKCPNEFTGDRCQNYVM ASFYKAEELYQGGGGQGGGGQGGGG QDKTHTCPPCPAPELLGGPSVFLFP PKPKDTLMISRTPEVTCVVVDVSHE DPEVKFNWYVDGVEVHNAKTKPCEE QYGSTYRCVSVLTVLHQDWLNGKEY KCKVSNKALPAPIEKTISKAKGQPR EPQVYTLPPSREEMTKNQVSLTCLV KGFYPSDIAVEWESNGQPENNYKTT PPVLDSDGSFFLYSKLTVDKSRWQQ GNVFSCSVMHEALHNHYTQKSLSLS PGK | 27 |
| huNRG1 (S177-S228) (wt)::3x (G4Q):: huFcSEFL2 *Pb) | SHLVKCAEKEKTFCVNGGECFMVKD LSNPSRYLCKCPNEFTGDRCQNYVM ASGGGGQGGGGQGGGGQDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 28 |
| huNRG1 (S177-Q237) (NRGE1 A):: GG:: huFcSEFL2 (Pb) | SHLVKCAENDKSFCVNGGECFMIEG PSNPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 29 |
| huNRG1 (S177-Q237) (NRGE1 B):: GG:: huFcSEFL2 (Pb) | SHLVKCGENDKSFCVNGGECYMVEG SSIPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE | 30 |

TABLE 1-continued

| Name | Sequences | SEQ ID NO |
|---|---|---|
| | SNGQPENNYKTTPPVLDSDGSFFLY SKLTVDKSRWQQGNVFSCSVMHEAL HNHYTQKSLSLSPGK | |
| huNRG1 (S177-Q237) (NRGE1 C):: GG:: huFcSEFL2 (Pb) | SHLVKCGEKHKSFCVNGGECFMIEG PSNPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 19 |
| huNRG1 (S177-Q237) (NRGE1 D):: GG:: huFcSEFL2 (Pb) | SHLVKCGESHKSFCVNGGECYMVEG SSIPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 22 |
| huNRG1 (S177-Q237) (NRGE1 E):: GG:: huFcSEFL2 (Pb) | SHLVKCGENDKSFCVNGGECFMIEG PSNPSRYLCKCPNEFTGDRCQNDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQK SLSLSPGK | 31 |
| huNRG1 (S177-Q237) (NRGE1 F):: GG:: huFcSEFL2 (Pb) | SHLVKCAENDKSFCVNGGECYMVEG SSIPSRYLCKCPNEFTGDRCQNDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 32 |
| huNRG1 (S177-Q237) (NRGE1 G):: GG:: huFcSEFL2 (Pb) | SHLVKCGEKHKSFCVNGGECYMVEG SSIPSRYLCKCPNEFTGDRCQNDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 33 |
| huNRG1 (S177-Q237) (NRGE1 H):: GG:: huFcSEFL2 | SHLVKCGESHKSFCVNGGECFMIEG PSNPSRYLCKCPNEFTGDRCQNDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT | 34 |

17

TABLE 1-continued

| Name | Sequences | SEQ ID NO |
|---|---|---|
| (Pb) | VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | |
| huNRG1 (S177-Q237) (NRGE1 I):: GG:: huFcSEFL2 (Pb) | SHLVKCGENDKSFCVNGGECFMIEG PSNPSRYLCKCPNEFTGDRCQDDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 35 |
| huNRG1 (S177-Q237) (NRGE1 J):: GG:: huFcSEFL2 (Pb) | SHLVKCGENDKSFCVNGGECYMVEG SSIPSRYLCKCPNEFTGDRCQDDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 36 |
| huNRG1 (S177-Q237) (NRGE1 K):: GG:: huFcSEFL2 (Pb) | SHLVKCAEKHKSFCVNGGECFMIEG PSNPSRYLCKCPNEFTGDRCQDDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 37 |
| huNRG1 (S177-Q237) (NRGE1 L):: GG:: huFcSEFL2 (Pb) | SHLVKCGESHKSFCVNGGECYMVEG SSIPSRYLCKCPNEFTGDRCQDDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 38 |
| huNRG1 (S177-Q237) (NRGE1 M):: GG:: huFcSEFL2 (Pb) | SHLVKCGENDKSFCVNGGECFMIEG PSNPSRYLCKCPNEFTGDRCQDFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 39 |
| huNRG1 (S177-Q237) (NRGE1 N):: | SHLVKCGENDKSFCVNGGECYMVEG SSIPSRYLCKCPNEFTGDRCQDFFM ASFYKAEELYQGGDKTHTCPPCPAP ELLGGPSVFLFPPKPKDTLMISRTP | 40 |

18

TABLE 1-continued

| Name | Sequences | SEQ ID NO |
|---|---|---|
| GG:: huFcSEFL2 (Pb) | EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | |
| huNRG1 (S177-Q237) (NRGE1 O):: GG:: huFcSEFL2 (Pb) | SHLVKCGEKHKSFCVNGGECYMVEG SSIPSRYLCKCPNEFTGDRCQDFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 41 |
| huNRG1 (S177-Q237) (NRGE1 P):: GG:: huFcSEFL2 (Pb) | SHLVKCAESHKSFCVNGGECFMIEG PSNPSRYLCKCPNEFTGDRCQDFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 42 |
| huNRG1 (S177-Q237) (1D3):: GG:: huFcSEFL2 (Pb) | SHLVKCGENDKSFCVNGGECFVIED PSIPSRYLCKCPNEFTGDRCQNDFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 43 |
| huNRG1 (S177-F229) (NRGE1 C) (D48T_F49Q_ M501)huIgG1 zSELF2Fc | SHLVKCGEKHKSFCVNGGECFMIEG PSNPSRYLCKCPNEFTGDRCQETQI ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 44 |
| huNRG1 (S177-F229) (NRGE1 C) (E47A_D48P_ F49H_M50I)h uIgG1zSELF2Fc | SHLVKCGEKHKSFCVNGGECFMIEG PSNPSRYLCKCPNEFTGDRCQAPHI ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 45 |

TABLE 1-continued

| Name | Sequences | SEQ ID NO |
|---|---|---|
| huNRG1 (S177-F229) (NRGEL C) (E47K_D48T_F49S_M50L)huIgG1zSELF2Fc | SHLVKCGEKHKSFCVNGGECFMIEG PSNPSRYLCKCPNEFTGDRCQKTSL ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 46 |
| huNRG1 (S177-F229) (NRGE1 C) (E47Q_D48S_ M50P)huIgG1 zSELF2Fc | SHLVKCGEKHKSFCVNGGECFMIEG PSNPSRYLCKCPNEFTGDRCQQSFP ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 47 |
| huNRG1 (S177-F229) (NRGE1 C) (E47S_D48A_ F49L_M50T)huIgG1zSELF2Fc | SHLVKCGEKHKSFCVNGGECFMIEG PSNPSRYLCKCPNEFTGDRCQSALT ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 48 |
| huNRG1 (S177-F229) (NRGE1 C) (E47S_D48T_ F49R_M50V)huIgG1zSELF2Fc | SHLVKCGEKHKSFCVNGGECFMIEG PSNPSRYLCKCPNEFTGDRCQSTRV ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 49 |
| huNRG1 (S177-F229) (NRGE1 C)huIgG1zSEL F2Fc | SHLVKCGEKHKSFCVNGGECFMIEG PSNPSRYLCKCPNEFTGDRCQEDFM ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 50 |
| huNRG1 (S177-F229) (NRGE1 D) (E47K_D48L_ F49D_M50I)huIgG1zSELF2Fc | SHLVKCGESHKSFCVNGGECYMVEG SSIPSRYLCKCPNEFTGDRCQKLDI ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS | 51 |

TABLE 1-continued

| Name | Sequences | SEQ ID NO |
|---|---|---|
| | FFLYSKLTVDKSRWQQGNVFSCSVM HEALHNHYTQKSLSLSPGK | |
| huNRG1 (S177-F229) (NRGE1 D) (E47S_D48S_ F49E_M50L)huIgG1zSELF2Fc | SHLVKCGESHKSFCVNGGECYMVEG SSIPSRYLCKCPNEFTGDRCQSSEL ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 52 |
| huNRG1 (S177-F229) (NRGE1 D) (E47T_D48S_ F49L_M50L)huIgG1zSELF2Fc | SHLVKCGESHKSFCVNGGECYMVEG SSIPSRYLCKCPNEFTGDRCQTSLL ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 53 |
| huNRG1 (S177-F229) (NRGE1 D)huIgG1zSEL F2Fc | SHLVKCGESHKSFCVNGGECYMVEG SSIPSRYLCKCPNEFTGDRCQEDFM ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 54 |
| huNRG1 (S177-F229) huIgG1z SELF2Fc | SHLVKCAEKEKTFCVNGGECFMVKD LSNPSRYLCKCPNEFTGDRCQNYVM ASFGGGGEGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 55 |
| huNRG1 (S177-F229) (NRGE1 C)6xHis | SHLVKCGEKHKSFCVNGGECFMIEG PSNPSRYLCKCPNEFTGDRCQEDFM ASFGGGGEGGGGAGGGGHHHHHH | 56 |
| huNRG1 (S177-F229) (NRGE1 C) (D48T_F49Q_ M50I)6xHis | SHLVKCGEKHKSFCVNGGECFMIEG PSNPSRYLCKCPNEFTGDRCQETQI ASFGGGGEGGGGAGGGGHHHHHH | 57 |
| huNRG1 (S177-F229) (NRGE1 C) (E47A_D48P_ F49HM50I)6x His | SHLVKCGEKHKSFCVNGGECFMIEG PSNPSRYLCKCPNEFTGDRCQAPHI ASFGGGGEGGGGAGGGGHHHHHH | 58 |

TABLE 1-continued

| Name | Sequences | SEQ ID NO |
|---|---|---|
| huNRG1 (S177-F229) (NRGE1 C) (E47K_D48T_ F49SM50L)6x His | SHLVKCGEKHKSFCVNGGECFMIEG PSNPSRYLCKCPNEFTGDRCQKTSL ASFGGGGEGGGGAGGGGHHHHHH | 59 |
| huNRG1 (S177-F229) (NRGE1 C) (E47Q_D48S_ M50P)6xHis | SHLVKCGEKHKSFCVNGGECFMIEG PSNPSRYLCKCPNEFTGDRCQQSFP ASFGGGGEGGGGAGGGGHHHHHH | 60 |
| huNRG1 (S177-F229) (NRGE1 C) (E47S_D48A_ F49LM50T)6x His | SHLVKCGEKHKSFCVNGGECFMIEG PSNPSRYLCKCPNEFTGDRCQSALT ASFGGGGEGGGGAGGGGHHHHHH | 61 |
| huNRG1 (S177-F229) (NRGE1 C) (E47S_D48T_ F49RM50V)6x His | SHLVKCGEKHKSFCVNGGECFMIEG PSNPSRYLCKCPNEFTGDRCQSTRV ASFGGGGEGGGGAGGGGHHHHHH | 62 |
| huNRG1 (S177-F229) (NRGE1 D)6xHis | SHLVKCGESHKSFCVNGGECYMVEG SSIPSRYLCKCPNEFTGDRCQEDFM ASFGGGGEGGGGAGGGGHHHHHH | 63 |
| huNRG1 (S177-F229) (NRGE1 D) (E47K_D48L_ F49DM50I)6x His | SHLVKCGESHKSFCVNGGECYMVEG SSIPSRYLCKCPNEFTGDRCQKLDI ASFGGGGEGGGGAGGGGHHHHHH | 64 |
| huNRG1 (S177-F229) (NRGE1 D) (E47S_D48S_ F49EM50L)6x His | SHLVKCGESHKSFCVNGGECYMVEG SSIPSRYLCKCPNEFTGDRCQSSEL ASFGGGGEGGGGAGGGGHHHHHH | 65 |
| huNRG1 (S177-F229) (NRGE1 D) (E47T_D48S_ F49LM50L)6x His | SHLVKCGESHKSFCVNGGECYMVEG SSIPSRYLCKCPNEFTGDRCQTSLL ASFGGGGEGGGGAGGGGHHHHHH | 66 |
| huNRG1 (S177-F229) (NRGE1 D) (E47V_D48T_ F49RM50L)6x His | SHLVKCGESHKSFCVNGGECYMVEG SSIPSRYLCKCPNEFTGDRCQVTRL ASFGGGGEGGGGAGGGGHHHHHH | 67 |
| huNRG1 (S177-F229) 6xHis | SHLVKCAEKEKTFCVNGGECFMVKD LSNPSRYLCKCPNEFTGDRCQNYVM ASFGGGGEGGGGAGGGGHHHHHH | 68 |
| :huFcSEFL2 (desK):G4SG4: huNRGI | DKTHTCPPCPAPELLGGPSVFLFPP KPKDTLMISRTPEVTCVVVDVSHED PEVKFNWYVDGVEVHNAKTKPCEEQ | 69 |

TABLE 1-continued

| Name | Sequences | SEQ ID NO |
|---|---|---|
| (S177-F229) (NRGE1C) | YGSTYRCVSVLTVLHQDWLNGKEYK CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GGGGGSGGGGSHLVKCGEKHKSFCV NGGECFMIEGPSNPSRYLCKCPNEF TGDRCQEDFMASFDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGGGGGSGGGGSH LVKCGEKHKSFCVNGGECFMIEGPS NPSRYLCKCPNEFTGDRCQEDFMAS F | |
| :huFcSEFL2 (desK):G4SG4:h uNRG1 (S177-F229) (NRGE1D) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GGGGGSGGGGSHLVKCGESHKSFCV NGGECYMVEGSSIPSRYLCKCPNEF TGDRCQEDFMASFDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGGGGGSGGGGSH LVKCGESHKSFCVNGGECYMVEGSS IPSRYLCKCPNEFTGDRCQEDFMAS F | 70 |
| :huFcSEFL2 (desK):G4SG4:h uNRG1 (S177-Q237) (NRGE1C) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GGGGGSGGGGSHLVKCGEKHKSFCV NGGECFMIEGPSNPSRYLCKCPNEF TGDRCQEDFMASFYKAEELYQDKTH TCPPCPAPELLGGPSVFLFPPKPKD TLMISRTPEVTCVVVDVSHEDPEVK FNWYVDGVEVHNAKTKPCEEQYGST YRCVSVLTVLHQDWLNGKEYKCKVS NKALPAPIEKTISKAKGQPREPQVY TLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGGGG GSGGGGSHLVKCGEKHKSFCVNGGE CFMIEGPSNPSRYLCKCPNEFTGDR CQEDFMASFYKAEELYQ | 71 |
| :huFcSEFL2 (desK):G4SG4:h uNRG1 (S177-Q237) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK | 72 |

TABLE 1-continued         TABLE 1-continued

| Name | Sequences | SEQ ID NO |
|---|---|---|
| (NRGE1D) | CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GGGGGSGGGGSHLVKCGESHKSFCV NGGECYMVEGSSIPSRYLCKCPNEF TGDRCQEDFMASFYKAEELYQDKTH TCPPCPAPELLGGPSVFLFPPKPKD TLMISRTPEVTCVVVDVSHEDPEVK FNWYVDGVEVHNAKTKPCEEQYGST YRCVSVLTVLHQDWLNGKEYKCKVS NKALPAPIEKTISKAKGQPREPQVY TLPPSREEMTKNQVSLTCLVKGFYP SDIAVEWESNGQPENNYKTTPPVLD SDGSFFLYSKLTVDKSRWQQGNVFS CSVMHEALHNHYTQKSLSLSPGGGG GSGGGGGSHLVKCGESHKSFCVNGGE CYMVEGSSIPSRYLCKCPNEFTGDR CQEDFMASFYKAEELYQ | |
| :huFcSEFL2 (desK)v131 (+) :G4SG4:huNRG1 (S177-F229) (NRGE1C) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREKMTKNQVSLTCLVK GFYPSDIAVEWESNGQPENNYKTTP PVLKSDGSFFLYSKLTVDKSRWQQG NVFSCSVMHEALHNHYTQKSLSLSP GGGGGSGGGGSHLVKCGEKHKSFCV NGGECFMIEGPSNPSRYLCKCPNEF TGDRCQEDFMASFDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTENQVSLTCLVEGFYPSDIAVEWE SNGQPENNYETTPPVLDSDGSFFLY SDLTVDKSRWQQGNVFSCSVMHEAL HNHYTQKSLSLSPGK | 73 |
| :huFcSEFL2 (desK)v131 (+) :G4SG4:huNRG1 (S177-F229) (NRGE1D) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREKMTKNQVSLTCLVK GFYPSDIAVEWESNGQPENNYKTTP PVLKSDGSFFLYSKLTVDKSRWQQG NVFSCSVMHEALHNHYTQKSLSLSP GGGGGSGGGGSHLVKCGESHKSFCV NGGECYMVEGSSIPSRYLCKCPNEF TGDRCQEDFMASFDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTENQVSLTCLVEGFYPSDIAVEWE SNGQPENNYETTPPVLDSDGSFFLY SDLTVDKSRWQQGNVFSCSVMHEAL HNHYTQKSLSLSPGK | 74 |
| :huFcSEFL2 (desK)v131 (+) :G4SG4:huNRG1 (S177-Q237) (NRGE1C) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREKMTKNQVSLTCLVK GFYPSDIAVEWESNGQPENNYKTTP PVLKSDGSFFLYSKLTVDKSRWQQG NVFSCSVMHEALHNHYTQKSLSLSP GGGGGSGGGGSHLVKCGEKHKSFCV NGGECFMIEGPSNPSRYLCKCPNEF | 75 |

| Name | Sequences | SEQ ID NO |
|---|---|---|
| | TGDRCQEDFMASFYKAEELYQDKTH TCPPCPAPELLGGPSVFLFPPKPKD TLMISRTPEVTCVVVDVSHEDPEVK FNWYVDGVEVHNAKTKPCEEQYGST YRCVSVLTVLHQDWLNGKEYKCKVS NKALPAPIEKTISKAKGQPREPQVY TLPPSREEMTENQVSLTCLVEGFYP SDIAVEWESNGQPENNYETTPPVLD SDGSFFLYSDLTVDKSRWQQGNVFS CSVMHEALHNHYTQKSLSLSPGK | |
| :huFcSEFL2 (desK)v131 (+) :G4SG4:huNRG1 (S177-Q237) (NRGE1D) | DKTHTCPPCPAPELLGGPSVFLFPP KPKDTLMISRTPEVTCVVVDVSHED PEVKFNWYVDGVEVHNAKTKPCEEQ YGSTYRCVSVLTVLHQDWLNGKEYK CKVSNKALPAPIEKTISKAKGQPRE PQVYTLPPSREKMTKNQVSLTCLVK GFYPSDIAVEWESNGQPENNYKTTP PVLKSDGSFFLYSKLTVDKSRWQQG NVFSCSVMHEALHNHYTQKSLSLSP GGGGGSGGGGSHLVKCGESHKSFCV NGGECYMVEGSSIPSRYLCKCPNEF TGDRCQEDFMASFYKAEELYQDKTH TCPPCPAPELLGGPSVFLFPPKPKD TLMISRTPEVTCVVVDVSHEDPEVK FNWYVDGVEVHNAKTKPCEEQYGST YRCVSVLTVLHQDWLNGKEYKCKVS NKALPAPIEKTISKAKGQPREPQVY TLPPSREEMTENQVSLTCLVEGFYP SDIAVEWESNGQPENNYETTPPVLD SDGSFFLYSDLTVDKSRWQQGNVFS CSVMHEALHNHYTQKSLSLSPGK | 76 |
| :huNRG1 (S177-F229) (NRGE 1C):: 2X (G4A)G4:: huFcSE FL2v131 (+) | SHLVKCGEKHKSFCVNGGECFMIEG PSNPSRYLCKCPNEFTGDRCQEDFM ASFGGGGAGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREKMTKNQVSLTCLVKGFYPSDIA VEWESNGQPENNYKTTPPVLKSDGS FFLYSKLTVDKSRWQQGNVFSCSVM HEALHNHYTQKSLSLSPGKDKTHTC PPCPAPELLGGPSVFLFPPKPKDTL MISRTPEVTCVVVDVSHEDPEVKFN WYVDGVEVHNAKTKPCEEQYGSTYR CVSVLTVLHQDWLNGKEYKCKVSNK ALPAPIEKTISKAKGQPREPQVYTL PPSREEMTENQVSLTCLVEGFYPSD IAVEWESNGQPENNYETTPPVLDSD GSFFLYSDLTVDKSRWQQGNVFSCS VMHEALHNHYTQKSLSLSPGK | 77 |
| :huNRG1 (S177-F229) (NRGE 1C):: 2X (G4E)G4:: huFcSE FL2v131 (+) | SHLVKCGEKHKSFCVNGGECFMIEG PSNPSRYLCKCPNEFTGDRCQEDFM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREKMTKNQVSLTCLVKGFYPSDIA VEWESNGQPENNYKTTPPVLKSDGS FFLYSKLTVDKSRWQQGNVFSCSVM HEALHNHYTQKSLSLSPGKDKTHTC PPCPAPELLGGPSVFLFPPKPKDTL MISRTPEVTCVVVDVSHEDPEVKFN WYVDGVEVHNAKTKPCEEQYGSTYR CVSVLTVLHQDWLNGKEYKCKVSNK ALPAPIEKTISKAKGQPREPQVYTL PPSREEMTENQVSLTCLVEGFYPSD IAVEWESNGQPENNYETTPPVLDSD GSFFLYSDLTVDKSRWQQGNVFSCS VMHEALHNHYTQKSLSLSPGK | 78 |

TABLE 1-continued

| Name | Sequences | SEQ ID NO |
|------|-----------|-----------|
| :huNRGI (S177-F229) (NRGE ID):: 2X (G4A)G4:: huFcSE FL2v131 (+) | SHLVKCGESHKSFCVNGGECYMVEG SSIPSRYLCKCPNEFTGDRCQEDFM ASFGGGGAGGGGAGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREKMTKNQVSLTCLVKGFYPSDIA VEWESNGQPENNYKTTPPVLKSDGS FFLYSKLTVDKSRWQQGNVFSCSVM HEALHNHYTQKSLSLSPGKDKTHTC PPCPAPELLGGPSVFLFPPKPKDTL MISRTPEVTCVVVDVSHEDPEVKFN WYVDGVEVHNAKTKPCEEQYGSTYR CVSVLTVLHQDWLNGKEYKCKVSNK ALPAPIEKTISKAKGQPREPQVYTL PPSREEMTENQVSLTCLVEGFYPSD IAVEWESNGQPENNYETTPPVLDSD GSFFLYSDLTVDKSRWQQGNVFSCS VMHEALHNHYTQKSLSLSPGK | 79 |
| :huNRGI (S177-F229) (NRGE ID):: 2X (G4E)G4:: huFcSE FL2v131 (+) | SHLVKCGESHKSFCVNGGECYMVEG SSIPSRYLCKCPNEFTGDRCQEDFM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREKMTKNQVSLTCLVKGFYPSDIA VEWESNGQPENNYKTTPPVLKSDGS FFLYSKLTVDKSRWQQGNVFSCSVM HEALHNHYTQKSLSLSPGKDKTHTC PPCPAPELLGGPSVFLFPPKPKDTL MISRTPEVTCVVVDVSHEDPEVKFN WYVDGVEVHNAKTKPCEEQYGSTYR CVSVLTVLHQDWLNGKEYKCKVSNK ALPAPIEKTISKAKGQPREPQVYTL PPSREEMTENQVSLTCLVEGFYPSD IAVEWESNGQPENNYETTPPVLDSD GSFFLYSDLTVDKSRWQQGNVFSCS VMHEALHNHYTQKSLSLSPGK | 80 |
| huNRG1 (S177-S228) (wt) ((G4E)2:G4):: huFcSEFL2 (Pb) | SHLVKCAEKEKTFCVNGGECFMVKD LSNPSRYLCKCPNEFTGDRCQNYVM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 81 |
| huNRG1 (S177-F229) (NRGE1C) ((G4E)2, G GT->GGCsilent mutation before terminal lysine):: G4:: huFcSEFL2 | SHLVKCGEKHKSFCVNGGECFMIEG PSNPSRYLCKCPNEFTGDRCQEDFM ASFGGGGEGGGGEGGGGDKTHTCPP CPAPELLGGPSVFLFPPKPKDTLMI SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | 4 |
| huNRG1 (S177-F229) (NRGE1D) ((G4E)2:G4):: | SHLVKCGESHKSFCVNGGECYMVEG SSIPSRYLCKCPNEFTGDRCQEDFM ASFGGGGEGGGGEGGGGDKTHTCPP CPAPELLGGPSVFLFPPKPKDTLMI | 11 |

TABLE 1-continued

| Name | Sequences | SEQ ID NO |
|------|-----------|-----------|
| huFcSEFL 2 (Pb) | SRTPEVTCVVVDVSHEDPEVKFNWY VDGVEVHNAKTKPCEEQYGSTYRCV SVLTVLHQDWLNGKEYKCKVSNKAL PAPIEKTISKAKGQPREPQVYTLPP SREEMTKNQVSLTCLVKGFYPSDIA VEWESNGQPENNYKTTPPVLDSDGS FFLYSKLTVDKSRWQQGNVFSCSVM HEALHNHYTQKSLSLSPGK | |
| huNRG1 (S177-Q237) (1A1):: GG:: huFcSEFL2 (Pb) | SHLVKCGESEKSFCVNGGECYVIED SSIPSRFLCKCPNEFTGDRCQNVFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 82 |
| huNRG1 (S177-Q237) (1A12):: GG:: huFcSEFL2 (Pb) | SHLVKCAEKHKSFCVNGGECYVVER PSIPSRYLCKCPNEFTGDRCQKFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 83 |
| huNRG1 (S177-Q237) (1A7):: GG:: huFcSEFL2 (Pb) | SHLVKCAERDKSFCVNGGECYVIEH LSNPSRFLCKCPNEFTGDRCQKDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 84 |
| huNRG1 (S177-Q237) (1B4):: GG:: huFcSEFL2 (Pb) | SHLVKCGERDKTFCVNGGECFMIED SSNPSRYLCKCPNEFTGDRCQKDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 85 |
| huNRG1 (S177-Q237) (1B9):: GG:: huFcSEFL2 (Pb) | SHLVKCAEKHKSFCVNGGECFMVED LSIPSRYLCKCPNEFTGDRCQDVFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQK SLSLSPGK | 86 |

TABLE 1-continued

| Name | Sequences | SEQ ID NO |
|---|---|---|
| huNRG1 (S177-Q237) (1C11) :: GG:: huFcSEFL2 (Pb) | SHLVKCGEKEKTFCVNGGECYMVER PSIPSRFLCKCPNEFTGDRCQKFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 87 |
| huNRG1 (S177-Q237) (1D10) :: GG:: huFcSEFL2 (Pb) | SHLVKCAERDKTFCVNGGECYMIED LSIPSRYLCKCPNEFTGDRCQKDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 88 |
| huNRG1 (S177-Q237) (1D3) :: GG:: huFcSEFL2 (Pb) | SHLVKCGENDKSFCVNGGECFVIED PSIPSRYLCKCPNEFTGDRCQNDFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 43 |
| huNRG1 (S177-Q237) (1D4) :: GG:: huFcSEFL2 (Pb) | SHLVKCGERDKTFCVNGGECYVVEH SSNPSRYLCKCPNEFTGDRCQKFFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 89 |
| huNRG1 (S177-Q237) (1D4) :: GG:: huFcSEFL2 (Pb) | SHLVKCGERDKTFCVNGGECYVVEH SSNPSRYLCKCPNEFTGDRCQKFFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 89 |
| huNRG1 (S177-Q237) (2E3) :: GG:: huFcSEFL2 (Pb) | SHLVKCGEKEKSFCVNGGECYMIEG LSIPSRFLCKCPNEFTGDRCQDVFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY | 90 |

| Name | Sequences | SEQ ID NO |
|---|---|---|
| | SKLTVDKSRWQQGNVFSCSVMHEAL HNHYTQKSLSLSPGK | |
| huNRG1 (S177-Q237) (2E4) :: GG:: huFcSEFL2 (Pb) | SHLVKCGESDKSFCVNGGECFMVKR PSNPSRYLCKCPNEFTGDRCQKVFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 91 |
| huNRG1 (S177-Q237) (2F2) :: GG:: huFcSEFL2 (Pb) | SHLVKCAESEKTFCVNGGECYMIEH PSNPSRFLCKCPNEFTGDRCQNVFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQK SLSLSPGK | 92 |
| huNRG1 (S177-Q237) (2G3) :: GG:: huFcSEFL2 (Pb) | SHLVKCGERQKSFCVNGGECYMVED LSIPSRYLCKCPNEFTGDRCQKVFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 93 |
| huNRG1 (S177-Q237) (2G4) :: GG:: huFcSEFL2 (Pb) | SHLVKCAENEKTFCVNGGECFVVEG LSIPSRYLCKCPNEFTGDRCQDVFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 94 |
| huNRG1 (S177-Q237) (2H7) :: GG:: huFcSEFL2 (Pb) | SHLVKCGEKEKSFCVNGGECYWEDL SIPSRFLCKCPNEFTGDRCQKWMAS FYKAEELYQGGDKTHTCPPCPAPEL LGGPSVFLFPPKPKDTLMISRTPEV TCVVVDVSHEDPEVKFNWYVDGVEV HNAKTKPCEEQYGSTYRCVSVLTVL HQDWLNGKEYKCKVSNKALPAPIEK TISKAKGQPREPQVYTLPPSREEMT KNQVSLTCLVKGFYPSDIAVEWESN GQPENNYKTTPPVLDSDGSFFLYSK LTVDKSRWQQGNVFSCSVMHEALHN HYTQKSLSLSPGK | 95 |
| huNRG1 (S177-Q237) (3A7) :: GG:: huFcSEFL2 (Pb) | SHLVKCAEKEKSFCVNGGECFVIEG SSIPSRFLCKCPNEFTGDRCQKVVM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI | 96 |

TABLE 1-continued

TABLE 1-continued

| Name | Sequences | SEQ ID NO |
|------|-----------|-----------|
| | EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | |
| huNRG1 (S177-Q237) (3B8):: huFcSEFL2 (Pb) | SHLVKCGERDKSFCVNGGECFMVER SSIPSRYLCKCPNEFTGDRCQDFFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 97 |
| huNRG1 (S177-Q237) (3D6):: huFcSEFL2 (Pb) | SHLVKCGESDKSFCVNGGECFVIEG SSIPSRFLCKCPNEFTGDRCQDFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 98 |
| huNRG1 (S177-Q237) (3D8):: huFcSEFL2 (Pb) | SHLVKCGEKDKTFCVNGGECFMVED LSIPSRFLCKCPNEFTGDRCQDFFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 99 |
| huNRG1 (S177-Q237) (3E6):: huFcSEFL2 (Pb) | SHLVKCAEKHKSFCVNGGECFVIEG SSIPSRFLCKCPNEFTGDRCQKDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 100 |
| huNRG1 (S177-Q237) (3E9):: huFcSEFL2 (Pb) | SHLVKCAENHKTFCVNGGECFVIEG SSNPSRYLCKCPNEFTGDRCQDVFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 101 |
| huNRG1 (S177-Q237) (3F2):: huFcSEFL2 | SHLVKCGESHKSFCVNGGECFMIEG PSNPSRYLCKCPNEFTGDRCQDDFM ASFYKAEELYQGGDKTHTCPPCPAP ELLGGPSVFLFPPKPKDTLMISRTP EVTCVVVDVSHEDPEVKFNWYVDGV | 102 |

| Name | Sequences | SEQ ID NO |
|------|-----------|-----------|
| (Pb) | EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | |
| huNRG1 (S177-Q237) (3G3):: huFcSEFL2 (Pb) | SHLVKCGEREKTFCVNGGECFMIEH LSIPSRFLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 103 |
| huNRG1 (S177-Q237) (3G9):: huFcSEFL2 (Pb) | SHLVKCGESHKSFCVNGGECFMVED LSNPSRFLCKCPNEFTGDRCQKDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 104 |
| huNRG1 (S177-Q237) (3H5):: huFcSEFL2 (Pb) | SHLVKCGERHKSFCVNGGECYVVER PSIPSRFLCKCPNEFTGDRCQKDFL ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 105 |
| huNRG1 (S177-Q237) (3H8):: huFcSEFL2 (Pb) | SHLVKCGEKHKSFCVNGGECYMVEG SSIPSRYLCKCPNEFTGDRCQEDFM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 106 |
| huNRG1 (S177-Q237) (_200E):: huFcSEFL2 (Pb) | SHLVKCAEKEKTFCVNGGECFMVED LSNPSRYLCKCPNEFTGDRCQNYVM ASFYKAEELYQGGDKTHTCPPCPAP ELLGGPSVFLFPPKPKDTLMISRTP EVTCVVVDVSHEDPEVKFNWYVDGV EVHNAKTKPCEEQYGSTYRCVSVLT VLHQDWLNGKEYKCKVSNKALPAPI EKTISKAKGQPREPQVYTLPPSREE MTKNQVSLTCLVKGFYPSDIAVEWE SNGQPENNYKTTPPVLDSDGSFFLY SKLTVDKSRWQQGNVFSCSVMHEAL HNHYTQKSLSLSPGK | 107 |
| huNRG1 (S177-Q237) (200EK | SHLVKCAEKEKTFCVNGGECFMVED LSNPSRYLCKCPNEFTGDRCQKDFM ASFYKAEELYQGGDKTHTCPPCPAP | 108 |

TABLE 1-continued

| Name | Sequences | SEQ ID NO |
|------|-----------|-----------|
| DF)::<br>GG::<br>huFcSEFL2<br>(Pb) | ELLGGPSVFLFPPKPKDTLMISRTP<br>EVTCVVVDVSHEDPEVKFNWYVDGV<br>EVHNAKTKPCEEQYGSTYRCVSVLT<br>VLHQDWLNGKEYKCKVSNKALPAPI<br>EKTISKAKGQPREPQVYTLPPSREE<br>MTKNQVSLTCLVKGFYPSDIAVEWE<br>SNGQPENNYKTTPPVLDSDGSFFLY<br>SKLTVDKSRWQQGNVFSCSVMHEAL<br>HNHYTQKSLSLSPGK | |
| huNRG1<br>(S177-Q237)<br>(FVIED<br>PSI)::<br>GG::<br>huFcSEFL2<br>(Pb) | SHLVKCAEKEKTFCVNGGECFVIED<br>PSIPSRYLCKCPNEFTGDRCQNYVM<br>ASFYKAEELYQGGDKTHTCPPCPAP<br>ELLGGPSVFLFPPKPKDTLMISRTP<br>EVTCVVVDVSHEDPEVKFNWYVDGV<br>EVHNAKTKPCEEQYGSTYRCVSVLT<br>VLHQDWLNGKEYKCKVSNKALPAPI<br>EKTISKAKGQPREPQVYTLPPSREE<br>MTKNQVSLTCLVKGFYPSDIAVEWE<br>SNGQPENNYKTTPPVLDSDGSFFLY<br>SKLTVDKSRWQQGNVFSCSVMHEAL<br>HNHYTQKSLSLSPGK | 109 |
| huNRG1<br>(S177-<br>huFcSEFL2<br>(Pb)Q237)<br>(wt)::<br>GG:: | SHLVKCAEKEKTFCVNGGECFMVKD<br>LSNPSRYLCKCPNEFTGDRCQNYVM<br>ASFYKAEELYQGGDKTHTCPPCPAP<br>ELLGGPSVFLFPPKPKDTLMISRTP<br>EVTCVVVDVSHEDPEVKFNWYVDGV<br>EVHNAKTKPCEEQYGSTYRCVSVLT<br>VLHQDWLNGKEYKCKVSNKALPAPI<br>EKTISKAKGQPREPQVYTLPPSREE<br>MTKNQVSLTCLVKGFYPSDIAVEWE<br>SNGQPENNYKTTPPVLDSDGSFFLY | 25 |

TABLE 1-continued

| Name | Sequences | SEQ ID NO |
|------|-----------|-----------|
| | SKLTVDKSRWQQGNVFSCSVMHEAL<br>HNHYTQKSLSLSPGK | |
| huNRG1<br>(S177-Q237)<br>(v80)::<br>GG::<br>huFcSEFL2<br>(Pb) | SHLVKCAESHKSFCVNGGECFVIEG<br>SSIPSRYLCKCPNEFTGDRCQKDVM<br>ASFYKAEELYQGGDKTHTCPPCPAP<br>ELLGGPSVFLFPPKPKDTLMISRTP<br>EVTCVVVDVSHEDPEVKFNWYVDGV<br>EVHNAKTKPCEEQYGSTYRCVSVLT<br>VLHQDWLNGKEYKCKVSNKALPAPI<br>EKTISKAKGQPREPQVYTLPPSREE<br>MTKNQVSLTCLVKGFYPSDIAVEWE<br>SNGQPENNYKTTPPVLDSDGSFFLY<br>SKLTVDKSRWQQGNVFSCSVMHEAL<br>HNHYTQKSLSLSPGK | 110 |
| huNRG1<br>(S177-Q237)<br>(v80.3)::<br>GG::<br>huFcSEFL2<br>(Pb) | SHLVKCAERHKSFCVNGGECFVIEG<br>SSIPSRYLCKCPNEFTGDRCEKDVM<br>ASFYKAEELYQGGDKTHTCPPCPAP<br>ELLGGPSVFLFPPKPKDTLMISRTP<br>EVTCVVVDVSHEDPEVKFNWYVDGV<br>EVHNAKTKPCEEQYGSTYRCVSVLT<br>VLHQDWLNGKEYKCKVSNKALPAPI<br>EKTISKAKGQPREPQVYTLPPSREE<br>MTKNQVSLTCLVKGFYPSDIAVEWE<br>SNGQPENNYKTTPPVLDSDGSFFLY<br>SKLTVDKSRWQQGNVFSCSVMHEAL<br>HNHYTQKSLSLSPGK | 111 |

Neuregulin variant ssequences are in bold.

The human neuregulin variant sequences (without linkers, Fc sequences or His tags) are presented in Table 2 below.

TABLE 2

| Variant name | HuNRG1 variant sequence | SEQ ID NO: |
|--------------|-------------------------|------------|
| NRG1(S177-Q237)<br>(NRGE1A) | SHLVKCAENDKSFCVNGGECFMIEGPSNPSRYLCKCPNEFTGDRCQEDFMASFYKAEELYQ | 114 |
| NRG1(S177-Q237)<br>(NRGE1B) | SHLVKCGENDKSFCVNGGECYMVEGSSIPSRYLCKCPNEFTGDRCQEDFMASFYKAEELYQ | 115 |
| NRG1(S177-S228)<br>(NRGE1C) | SHLVKCGEKHKSFCVNGGECFMIEGPSNPSRYLCKCPNEFTGDRCQEDFMAS | 116 |
| NRG1(S177-F229)<br>(NRGE1C) | SHLVKCGEKHKSFCVNGGECFMIEGPSNPSRYLCKCPNEFTGDRCQEDFMASF | 117 |
| NRG1(S177-F229)<br>(NRGEIC TQI) | SHLVKCGEKHKSFCVNGGECFMIEGPSNPSRYLCKCPNEFTGDRCQETQIASF | 118 |
| NRG1(S177-F229)<br>(NRGEIC APHI) | SHLVKCGEKHKSFCVNGGECFMIEGPSNPSRYLCKCPNEFTGDRCQAPHIASF | 119 |
| NRG1(S177-F229)<br>(NRGEIC KTSL) | SHLVKCGEKHKSFCVNGGECFMIEGPSNPSRYLCKCPNEFTGDRCQKTSLASF | 120 |

TABLE 2-continued

| Variant name | HuNRG1 variant sequence | SEQ ID NO: |
|---|---|---|
| NRG1(S177-F229) (NRGEIC QSP) | SHLVKCGEKHKSFCVNGGECFMIEGPSNPSRYLCKCPNEFTGDRCQQSFPASF | 121 |
| NRG1(S177-F229) (NRGEIC SALT) | SHLVKCGEKHKSFCVNGGECFMIEGPSNPSRYLCKCPNEFTGDRCQSALTASF | 122 |
| NRG1(S177-F229) (NRGEIC STRV) | SHLVKCGEKHKSFCVNGGECFMIEGPSNPSRYLCKCPNEFTGDRCQSTRVASF | 123 |
| NRG1(S177-Q237) (NRGEIC) | SHLVKCGEKHKSFCVNGGECFMIEGPSNPSRYLCKCPNEFTGDRCQEDFMASF YKAEELYQ | 124 |
| NRG1(S177-S228) (NRGEID) | SHLVKCGESHKSFCVNGGECYMVEGSSIPSRYLCKCPNEFTGDRCQEDFMAS | 125 |
| NRG1(S177-F229) (NRGEID) | SHLVKCGESHKSFCVNGGECYMVEGSSIPSRYLCKCPNEFTGDRCQEDFMASF | 126 |
| NRG1(S177-F229) (NRGEID KLDI) | SHLVKCGESHKSFCVNGGECYMVEGSSIPSRYLCKCPNEFTGDRCQKLDIASF | 127 |
| NRG1(S177-F229) (NRGEID SSEL) | SHLVKCGESHKSFCVNGGECYMVEGSSIPSRYLCKCPNEFTGDRCQSSELASF | 128 |
| NRG1(S177-F229) (NRGEID TSLL) | SHLVKCGESHKSFCVNGGECYMVEGSSIPSRYLCKCPNEFTGDRCQTSLLASF | 129 |
| NRG1(S177 - F229) (NRGE1D VTRL) | SHLVKCGESHKSFCVNGGECYMVEGSSIPSRYLCKCPNEFTGDRCQVTRLASF | 130 |
| NRG1(S177-Q237) (NRGE1D) | SHLVKCGESHKSFCVNGGECYMVEGSSIPSRYLCKCPNEFTGDRCQEDFMASFY KAEELYQ | 131 |
| NRG1(S177-Q237) (NRGE1E) | SHLVKCGENDKSFCVNGGECFMIEGPSNPSRYLCKCPNEFTGDRCQNDFMASFY KAEELYQ | 132 |
| NRG1(S177-Q237) (NRGEIF) | SHLVKCAENDKSFCVNGGECYMVEGSSIPSRYLCKCPNEFTGDRCQNDFMASFY KAEELYQ | 133 |
| NRG1(S177-Q237) (NRGEIG) | SHLVKCGEKHKSFCVNGGECYMVEGSSIPSRYLCKCPNEFTGDRCQNDFMASFY KAEELYQ | 134 |
| NRG1(S177-Q237) (NRGEIH) | SHLVKCGESHKSFCVNGGECFMIEGPSNPSRYLCKCPNEFTGDRCQNDFMASFY KAEELYQ | 135 |
| NRG1(S177-Q237) (NRGEII) | SHLVKCGENDKSFCVNGGECFMIEGPSNPSRYLCKCPNEFTGDRCQDDFMASFY KAEELYQ | 136 |
| NRG1(S177-Q237) (NRGE1J) | SHLVKCGENDKSFCVNGGECYMVEGSSIPSRYLCKCPNEFTGDRCQDDFMASFY KAEELYQ | 137 |

TABLE 2-continued

| Variant name | HuNRG1 variant sequence | SEQ ID NO: |
|---|---|---|
| NRG1(S177-Q237) (NRGEIK) | SHLVKCAEKHKSFCVNGGECFMIEGPSNPSRYLCKCPNEFTGDRCQDDFMASFY KAEELYQ | 138 |
| NRG1(S177-Q237) (NRGEIL) | SHLVKCGESHKSFCVNGGECYMVEGSSIPSRYLCKCPNEFTGDRCQDDFMASFY KAEELYQ | 139 |
| NRG1(S177-Q237) (NRGE1M) | SHLVKCGENDKSFCVNGGECFMIEGPSNPSRYLCKCPNEFTGDRCQDFFMASFY KAEELYQ | 140 |
| NRG1(S177-Q237) (NRGEIN) | SHLVKCGENDKSFCVNGGECYMVEGSSIPSRYLCKCPNEFTGDRCQDFFMASFY KAEELYQ | 141 |
| NRG1(S177-Q237) (NRGE1O) | SHLVKCGEKHKSFCVNGGECYMVEGSSIPSRYLCKCPNEFTGDRCQDFFMASFY KAEELYQ | 142 |
| NRG1(S177-Q237) (NRGEIP) | SHLVKCAESHKSFCVNGGECFMIEGPSNPSRYLCKCPNEFTGDRCQDFFMASF YKAEELYQ | 143 |
| NRG1(S177-Q237) (1A1) | SHLVKCGESEKSFCVNGGECYVIEDSSIPSRFLCKCPNEFTGDRCQNVFLASF YKAEELYQ | 144 |
| NRG1(S177-Q237) (1A12) | SHLVKCAEKHKSFCVNGGECYVVERPSIPSRYLCKCPNEFTGDRCQKFFMASFY KAEELYQ | 145 |
| NRG1(S177-Q237) (1A7) | SHLVKCAERDKSFCVNGGECYVIEHLSNPSRFLCKCPNEFTGDRCQKDFMASFY KAEELYQ | 146 |
| NRG1(S177-Q237) (1B4) | SHLVKCGERDKTFCVNGGECFMIEDSSNPSRYLCKCPNEFTGDRCQKDFMASFY KAEELYQ | 147 |
| NRG1(S177-Q237) (1B9) | SHLVKCAEKHKSFCVNGGECFMVEDLSIPSRYLCKCPNEFTGDRCQDVFMASFY KAEELYQ | 148 |
| NRG1(S177-Q237) (1C11) | SHLVKCGEKEKTFCVNGGECYMVERPSIPSRFLCKCPNEFTGDRCQKFFMASFY KAEELYQ | 149 |
| NRG1(S177-Q237) (1D10) | SHLVKCAERDKTFCVNGGECYMIEDLSIPSRYLCKCPNEFTGDRCQKDFMASFY KAEELYQ | 150 |
| NRG1(S177-Q237) (1D3) | SHLVKCGENDKSFCVNGGECFVIEDPSIPSRYLCKCPNEFTGDRCQNDFLASFY KAEELYQ | 151 |
| NRG1(S177-Q237) (1D4) | SHLVKCGERDKTFCVNGGECYVVEHSSNPSRYLCKCPNEFTGDRCQKFFLASFY KAEELYQ | 152 |
| NRG1(S177-Q237) (2E3) | SHLVKCGEKEKSFCVNGGECYMIEGLSIPSRFLCKCPNEFTGDRCQDVFMASFY KAEELYQ | 153 |
| NRG1(S177-Q237) (2E4) | SHLVKCGESDKSFCVNGGECFMVKRPSNPSRYLCKCPNEFTGDRCQKVFLASFY KAEELYQ | 154 |
| NRG1(S177-Q237) (2F2) | SHLVKCAESEKTFCVNGGECYMIEHPSNPSRFLCKCPNEFTGDRCQNVFMASFY KAEELYQ | 155 |
| NRG1(S177-Q237) (2G3) | SHLVKCGERQKSFCVNGGECYMVEDLSIPSRYLCKCPNEFTGDRCQKVFMASFY KAEELYQ | 156 |
| NRG1(S177-Q237) (2G4) | SHLVKCAENEKTFCVNGGECFVVEGLSIPSRYLCKCPNEFTGDRCQDVFMASFY KAEELYQ | 157 |
| NRG1(S177-Q237) (2H7) | SHLVKCGEKEKSFCVNGGECYVVEDLSIPSRFLCKCPNEFTGDRCQKVVMASFY KAEELYQ | 158 |
| NRG1(S177-Q237) (3A7) | SHLVKCAEKEKSFCVNGGECFVIEGSSIPSRFLCKCPNEFTGDRCQKVVMASFY KAEELYQ | 159 |

TABLE 2-continued

| Variant name | HuNRG1 variant sequence | SEQ ID NO: |
|---|---|---|
| NRG1(S177-Q237) (3B8) | SHLVKCGERDKSFCVNGGECFMVERSSIPSRYLCKCPNEFTGDRCQDFFLASFY KAEELYQ | 160 |
| NRG1(S177-Q237) (3D6) | SHLVKCGESDKSFCVNGGECFVIEGSSIPSRFLCKCPNEFTGDRCQDFFMASFY KAEELYQ | 161 |
| NRG1(S177-Q237) (3D8) | SHLVKCGEKDKTFCVNGGECFMVEDLSIPSRFLCKCPNEFTGDRCQDFFMASFY KAEELYQ | 162 |
| NRG1(S177-Q237) (3E6) | SHLVKCAEKHKSFCVNGGECYVIEGSSIPSRFLCKCPNEFTGDRCQKDFMASFY KAEELYQ | 163 |
| NRG1(S177-Q237) (3E9) | SHLVKCAENHKTFCVNGGECFVIEGSSNPSRYLCKCPNEFTGDRCQDVFLASFY KAEELYQ | 164 |
| NRG1(S177-Q237) (3F2) | SHLVKCGESHKSFCVNGGECFMIEGPSNPSRYLCKCPNEFTGDRCQDDFMASFY KAEELYQ | 165 |
| NRG1(S177-Q237) (3G3) | SHLVKCGEREKTFCVNGGECFMIEHLSIPSRFLCKCPNEFTGDRCQEDFMASFY KAEELYQ | 166 |
| NRG1(S177-Q237) (3G9) | SHLVKCGESHKSFCVNGGECFMVEDLSNPSRFLCKCPNEFTGDRCQKDFMASFY KAEELYQ | 167 |
| NRG1(S177-Q237) (3H5) | SHLVKCGERHKSFCVNGGECYVVERPSIPSRFLCKCPNEFTGDRCQKDFLASFY KAEELYQ | 168 |
| NRG1(S177-S228) (3H8) | SHLVKCGEKHKSFCVNGGECYMVEGSSIPSRYLCKCPNEFTGDRCQEDFMAS | 169 |
| NRG1(S177-F229) (3H8) | SHLVKCGEKHKSFCVNGGECYMVEGSSIPSRYLCKCPNEFTGDRCQEDFMASF | 170 |
| NRG1(S177-Q237) (3H8) | SHLVKCGEKHKSFCVNGGECYMVEGSSIPSRYLCKCPNEFTGDRCQEDFMASFY KAEELYQ | 171 |
| NRG1(S177-Q237) (200E) | SHLVKCAEKEKTFCVNGGECFMVEDLSNPSRYLCKCPNEFTGDRCQNYVMASFY KAEELYQ | 172 |
| NRG1(S177-Q237) (200E KDF) | SHLVKCAEKEKTFCVNGGECFMVEDLSNPSRYLCKCPNEFTGDRCQKDFMASFY KAEELYQ | 173 |
| NRG1(S177-Q237) (FVIEDPSI) | SHLVKCAEKEKTFCVNGGECFVIEDPSIPSRYLCKCPNEFTGDRCQNYVMASFY KAEELYQ | 174 |
| NRG1(S177-Q237) (v80) | SHLVKCAESHKSFCVNGGECFVIEGSSIPSRYLCKCPNEFTGDRCQKDVMASFY KAEELYQ | 175 |
| NRG1(S177-Q237) (v80.3) | SHLVKCAERHKSFCVNGGECFVIEGSSIPSRYLCKCPNEFTGDRCEKDVMASFY KAEELYQ | 176 |

In certain embodiments, the polypeptide variant comprises an amino acid sequence of the formula:

(SEQ ID NO: 177)

$$SHLVKCX_{183}EX_{185}X_{186}KX_{188}FCVNGGECX_{197}$$

$$X_{198}X_{199}X_{200}X_{201}X_{202}SX_{204}PSRX_{208}LCK$$

$$CPNEFTGDRCX_{222}X_{223}X_{224}X_{225}X_{226}ASX_{229}$$

wherein $X_{183}$ is A or G;

$X_{185}X_{186}$ is KD, KE, KH, ND, NE, NH, RD, RE, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMIEHL (SEQ ID NO:180), FMVEDL (SEQ ID NO:181), FMVERS (SEQ ID NO:182), FMVKRP (SEQ ID NO:183), FVIEDP (SEQ ID NO:184), FVIEGS (SEQ ID NO:185), FVVEGL (SEQ ID NO:186), YMIEDL (SEQ ID NO:187), YMIEGL (SEQ ID NO:188), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEDL (SEQ ID NO:196), YVVEHS (SEQ ID NO:197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QDDFM (SEQ ID NO:201), QDFFL (SEQ ID NO:202), QDFFM (SEQ ID NO:203), QDVFL (SEQ ID NO:204), QDVFM (SEQ ID NO:205), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215), QKVFM (SEQ ID NO:216), QKVVM (SEQ ID NO:217), QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is absent, F or FYKAEELYQ (SEQ ID NO:229).

In the above formula and formulae below, wild-type sequences are underlined.

When $X_{229}$ is absent, the formula can be represented by: SHLVKCX$_{183}$EX$_{185}$X$_{186}$KX$_{188}$FCVNGGECX$_{197}$X$_{198}$X$_{199}$X$_{200}$X$_{201}$X$_{202}$SX$_{204}$PSRX$_{205}$ LCKCPNE FTGDRCX$_{222}$X$_{223}$X$_{224}$X$_{225}$X$_{226}$AS (SEQ ID NO:230).

When $X_{229}$ is FYKAEELYQ (SEQ ID NO:229), the formula can be represented by: SHLVKCX$_{183}$EX$_{185}$X$_{186}$KX$_{188}$FCVNGGECX$_{197}$X$_{198}$X$_{199}$X$_{200}$X$_{201}$X$_{202}$SX$_{204}$PSRX$_{205}$ LCKCPNE FTGDRCX$_{222}$X$_{223}$X$_{224}$X$_{225}$X$_{226}$ASFYKAEELYQ (SEQ ID NO:231).

In certain embodiments, the polypeptide variant comprises an amino acid sequence of any of SEQ ID Nos: 114 to 176.

In certain embodiments, the polypeptide variant comprises an amino acid sequence of any of SEQ ID Nos: 1 to 24, 29 to 54, 56 to 67, 69 to 80, or 82 to 111.

In certain embodiments, the polypeptide variant comprises an amino acid sequence of the formula:

$$[\text{SEQ ID NO: 177}]$$
$$\text{SHLVKCX}_{183}\text{EX}_{185}\text{X}_{186}\text{KX}_{188}\text{FCVNGGECX}_{197}$$
$$\text{X}_{198}\text{X}_{199}\text{X}_{200}\text{X}_{201}\text{X}_{202}\text{SX}_{204}\text{PSRX}_{208}\text{LCKC}$$
$$\text{PNEFTGDRCX}_{222}\text{X}_{223}\text{X}_{224}\text{X}_{225}\text{X}_{226}\text{ASX}_{229}$$

wherein $X_{183}$ is A or G;

$X_{185}X_{186}$ is KD, KE, KH, ND, NH, RD, RE, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMIEHL (SEQ ID NO:180), FMVEDL (SEQ ID NO:181), FMVERS (SEQ ID NO:182), FMVKRP (SEQ ID NO:183), FVIEDP (SEQ ID NO:184), FVIEGS (SEQ ID NO:185), YMIEDL (SEQ ID NO:187), YMIEGL (SEQ ID NO:188), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEHS (SEQ ID NO:197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QDFFL (SEQ ID NO:202),

QDFFM (SEQ ID NO:203), QDVFL (SEQ ID NO:204), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215), QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_{229}$ is F or FYKAEELYQ (SEQ ID NO:229).

In certain embodiments, the polypeptide variant comprises an amino acid sequence of any of SEQ ID Nos: 114, 115, 117 to 124, 126 to 135, 138, 139, 144 to 147, 149 to 156, 160 to 168, or 171 to 176.

In certain embodiments, the polypeptide variant comprises an amino acid sequence of any of SEQ ID Nos: 1 to 15, 19, 20, 22, 23, 29 to 34, 37, 38, 43 to 54, 56 to 59, 61 to 67, 69 to 80, 82 to 85, 87 to 93, or 97 to 111.

In certain embodiments, the polypeptide variant comprises an amino acid sequence of the formula:

$$(\text{SEQ ID NO: 177})$$
$$\text{SHLVKCX}_{183}\text{EX}_{185}\text{X}_{186}\text{KX}_{188}\text{FCVNGGECX}_{197}$$
$$\text{X}_{198}\text{X}_{199}\text{X}_{200}\text{X}_{201}\text{X}_{202}\text{SX}_{204}\text{PSRX}_{208}\text{LCKC}$$
$$\text{PNEFTGDRCX}_{222}\text{X}_{223}\text{X}_{224}\text{X}_{225}\text{X}_{226}\text{ASX}_{229}$$

wherein $X_{183}$ is A or G;

$X_{185}$ is, KE, KH, ND, RD, RH, RQ, SD, SE, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMVEDL (SEQ ID NO:181), FMVKRP (SEQ ID NO:183), FVIEDP (SEQ ID NO:184), FVIEGS (SEQ ID NO:185), YMIEDL (SEQ ID NO:187), YMIEHP (SEQ ID NO:189), YMVEDL (SEQ ID NO:190), YMVEGS (SEQ ID NO:191), YMVERP (SEQ ID NO:192), YVIEDS (SEQ ID NO:193), YVIEGS (SEQ ID NO:194), YVIEHL (SEQ ID NO:195), YVVEHS (SEQ ID NO:197), or YVVERP (SEQ ID NO:198);

$X_{204}$ is I or N;

$X_{205}$ is F or Y;

$X_{222}X_{223}X_{224}X_{225}X_{226}$ is EKDVM (SEQ ID NO:199), QAPHI (SEQ ID NO:200), QEDFM (SEQ ID NO:206), QETQI (SEQ ID NO:207), QKDFL (SEQ ID NO:208), QKDFM (SEQ ID NO:209), QKDVM (SEQ ID NO:210), QKFFL (SEQ ID NO:211), QKFFM (SEQ ID NO:212), QKLDI (SEQ ID NO:213), QKTSL (SEQ ID NO:214), QKVFL (SEQ ID NO:215), QNDFL (SEQ ID NO:218), QNDFM (SEQ ID NO:219), QNVFL (SEQ ID NO:220), QNVFM (SEQ ID NO:221), QNYVM (SEQ ID NO:222), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and $X_8$ is F or FYKAEELYQ (SEQ ID NO:229).

In certain embodiments, the polypeptide variant comprises an amino acid sequence of any of SEQ ID Nos: 117 to 124, 126 to 135, 144 to 147, 149 to 152, 154 to 156, 163, 167, 168, or 171 to 176.

In certain embodiments, the polypeptide variant comprises an amino acid sequence of any of SEQ ID Nos: 3, 4, 6, 9, 11 to 13, 19, 22, 31 to 34, 43 to 48, 52, 54, 56 to 59, 61 to 63, 65 to 67, 71, 72, 75 to 80, 84, 85, 88, 100, or 104 to 106.

In certain embodiments, the polypeptide variant comprises an amino acid sequence of the formula:

[SEQ ID NO: 177]

$$SHLVKCX_{183}EX_{185}X_{186}KX_{188}FCVNGGECX_{197}$$

$$X_{198}X_{199}X_{200}X_{201}X_{202}SX_{204}PSRX_{208}LCKC$$

$$PNEFTGDRCX_{222}X_{223}X_{224}X_{225}X_{226}ASX_{229}$$

wherein $X_{183}$ is A or G;

$X_{185}X_{186}$ is KH, ND, RD, RH, or SH;

$X_{188}$ is S or T;

$X_{197}X_{198}X_{199}X_{200}X_{201}X_{202}$ is FMIEDS (SEQ ID NO:178), FMIEGP (SEQ ID NO:179), FMVEDL (SEQ ID NO:181), FVIEDP (SEQ ID NO:184), YMIEDL (SEQ ID NO:187), YMVEGS (SEQ ID NO:191), YVIEGS (SEQ ID NO:194), YVIEHL (SEQ ID NO:195), or YVVERP (SEQ ID NO:198);

$X_{204}$ is I or N;

$X_{208}$ is F or Y;

$X_{222}X_{223}X_{224}X_{225}X_{226}$ is QAPHI (SEQ ID NO:200), QEDFM (SEQ ID NO:206), QETQI (SEQ ID NO:207), QKDFL (SEQ ID NO:208), QKDFM (SEQ ID NO:209), QKTSL (SEQ ID NO:214), QNDFL (SEQ ID NO:218), QNDFM (SEQ ID NO:219), QQSFP (SEQ ID NO:223), QSALT (SEQ ID NO:224), QSSEL (SEQ ID NO:225), QSTRV (SEQ ID NO:226), QTSLL (SEQ ID NO:227), or QVTRL (SEQ ID NO:228); and;

$X_{229}$ is F or FYKAEELYQ (SEQ D NO:229).

In certain embodiments, the polypeptide variant comprises an amino acid sequence of any of SEQ ID Nos: 117 to 124, 126, 128 to 135, 146, 147, 150, 151, 163, 167, 168, or 171.

In certain embodiments, the polypeptide variant comprises an amino acid sequence of any of SEQ ID Nos: 3, 4, 6, 9, 11 to 13, 19, 22, 31 to 34, 43 to 48, 52, 54, 56 to 59, 61 to 63, 65 to 67, 71, 72, 75 to 80, 84, 85, 88, 100, or 104 to 106.

In certain embodiments, the polypeptide variant has enhanced binding affinity to ErbB4 compared to the polypeptide of SEQ ID NO: 112.

In certain embodiments, the polypeptide variant has decreased binding affinity for ErbB3 compared to the polypeptide of SEQ ID NO:112.

In certain embodiments, the polypeptide variant has increased binding affinity for ErbB4 while having similar binding affinity to ErbB3 compared to the polypeptide of SEQ ID NO:112.

In certain embodiments, the polypeptide variant has increased binding affinity for ErbB4 while having decreased binding affinity for ErbB3 compared to the polypeptide of SEQ ID NO: 112.

In certain embodiments, the polypeptide variant has similar binding for ErbB4 while having decreased binding for ErbB3 compared to the polypeptide of SEQ ID NO: 124.

In certain embodiments, the polypeptide variant has a selectivity for ErbB4/ErbB3 that is at least 500, at least 1000, at least 5000, or at least 10,000. Selectivity for ErbB4/ErbB3 can be measured by methods known to those skilled in the art such as the Akt assay described in Example 1. For example, selectivity can be expressed at the ratio of EC50s in Schwann cells/cardiomyocytes. This ratio provides the activity in neural cells compared to heart cells.

In certain embodiments, the polypeptide variants have agonist activity that is at least 50%, 60%, 70%, or 80% of the activity against the wild-type sequence. This can be measured by phosphorylation of Akt.

Any of the above-described neuregulin variants can be modified by fusion to a heterologous polypeptide to produce a "chimeric neuregulin variant" or fusion protein. Typically, the heterologous polypeptide is fused at the N- or C terminus of the neuregulin variant to preserve the biological activity of the neuregulin variant. However, the heterologous polypeptide can also be introduced into regions of the neuregulin variant that are not critical for biological activity. Generally, chimeric neuregulin variants are produced by recombinant techniques or chemical synthesis. Examples of chimeric neuregulin variants include a neuregulin variant fused to a "signal sequence", a "purification handle", an immunoglobulin sequence or any combination thereof. Linkers may be used to connect the neuregulin polypeptide to a heterologous polypeptide.

A "signal sequence" is an amino acid sequence that directs the secretion of a polypeptide fused thereto from a cell expressing the chimeric protein. Thus, fusion of a neuregulin variant to a signal sequence facilitates recombinant production of the neuregulin variant because the chimeric neuregulin variant is secreted into the host cell culture medium, from which the chimeric neuregulin variant can be recovered with relative ease. A suitable signal sequence can be obtained from any protein that has a signal sequence and is typically (but not always) fused to the N-terminus of the neuregulin variant. DNA encoding prokaryotic signal sequences can be obtained, for example, from lamB or ompF, MalE, PhoA, and other genes. Another suitable prokaryotic signal sequence is the *E. coli* heat-stable enterotoxin II (STII) signal sequence. Mammalian signal sequences are discussed below.

A "purification handle" is a portion of a polypeptide or a polypeptide sequence that binds another polypeptide, termed a "binding partner." The fusion of a purification handle to a neuregulin variant confers on the variant the ability to bind the binding partner, which facilitates purification of the resultant chimeric neuregulin variant. Generally, the purification handle is selected so that the binding partner does not substantially cross-react with other components present in the mixture from which the chimeric neuregulin variant is to be purified. An exemplary "purification handle" is a His tag sequence. As used herein, the term "does not substantially cross-react" means that the affinity of the binding partner for the purification handle is at least about 20-fold, usually at least about 100-fold, more usually at least about 1000-fold, any affinity for any other components present in the mixture.

A chimeric neuregulin variant includes a neuregulin variant fused to an immunoglobulin sequence. In one embodiment, the immunoglobulin sequence is a Fc region of an IgG molecule (e.g., IgG1, IgG2, IgG3, or IgG4) that increases the in vivo serum half-life of the IgG. See, e.g., U.S. Patent Application Publication No. US2006/0140934.

In one embodiment, a neuregulin variant is attached to a linker via the first (1st) amino acid on the N-terminus of the neuregulin variant, which in one embodiment is a Serine (S or Ser) amino acid.

In certain embodiments, the Fc region has at least one mutation, preferably to reduce effector function and/or extend the half-life of the molecule. In certain aspects, the Fc region comprises at least one mutation in amino acids 234, 239, 434, or a combination thereof (numbered according to EU numbering), where in certain aspects, the amino acid mutations comprise at least one of the following substitution mutations: L234F, S239A, N434A or a combination thereof. Mutations to amino acids 234 and/or 239 knock down effector functions of the Fc region. Mutation to amino acid 434 extends the half-life of the fusion protein in a subject. Other mutations are known in the art such as the SEFL2.0 and SEFL2.2 mutations. See, e.g., Jacobsen et al., 2017, J Biol Chem 292:1865-1875 and Yang et al., 2018, Front Immunol Vol. 8, Art. 1860.

In certain embodiments, the one or more mutations in the Fc region reduce effector function. In some embodiments, the reduced effector function comprises a reduced affinity of the fusion protein for one or more Fe Receptors. The FcRs can be FcγRI, FcγRIIa, FcγRIib, FcγRIIIa (158F), FcγRIIIa (158V) and Clq.

In one embodiment, a fusion protein comprises a neuregulin variant fused to or operably linked to the C-terminus of an Fc region via a GGGGSGGGGS (G4S) linker (SEQ ID NO: 113). In some embodiments, one or more copies of the linker may be used. In other embodiments, 2, 3, 4, or 5 copies of the G4S linker or any other linker known in the art and/or as described herein as being suitable for the composition disclosed herein may be used herein.

The term "linker" is art-recognized and refers to a molecule (including but not limited to unmodified or modified nucleotides or amino acids) or group of molecules (for example, 2 or more, e.g., 2, 3, 4, 5, 6, 7, 8, 9, 10, 15, 20, 25, 30, 35, 40, 45, 50, 55, 60, 65, 70, 75, 80, 85, 90, 95, 100 or more) connecting two compounds, such as two polypeptides. The linker may be comprised of a single linking molecule or may comprise a linking molecule and at least one spacer molecule, intended to separate the linking molecule and a compound by a specific distance.

Preparation of Neuregulin Variants

The polypeptides of the invention may be produced by chemical synthesis or recombinant methods. Methods of chemically synthesizing polypeptides are well known in the art. Synthesizing polypeptides using recombinant methods are also well known in the art and are further described herein.

Methods and vectors for genetically engineering cells and/or cell lines to express, for example, a polypeptide, are well known to those of skill in the art; for example, various techniques are illustrated in *Current Protocols in Molecular Biology*, Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69. The polypeptides generated may be tested for their binding affinity to the receptor and activation of the receptor using methods known in the art.

A vector may be any molecule or entity (e.g., nucleic acid, plasmid, bacteriophage, transposon, cosmid, chromosome, virus, virus capsid, virion, naked DNA, complexed DNA and the like) suitable for use to transfer and/or transport protein encoding information into a host cell and/or to a specific location and/or compartment within a host cell. Vectors can include viral and non-viral vectors, non-episomal mammalian vectors. Vectors are often referred to as expression vectors, for example, recombinant expression vectors and cloning vectors. The vector may be introduced into a host cell to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art.

Vectors are useful for transformation of a host cell and contain nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto. "Operably linked" means that the components to which the term is applied are in a relationship that allows them to carry out their inherent functions. For example, a control sequence, e.g., a promoter, in a vector that is "operably linked" to a protein coding sequence are arranged such that normal activity of the control sequence leads to transcription of the protein coding sequence resulting in recombinant expression of the encoded protein.

Vectors may be selected to be functional in the particular host cell employed (i.e., the vector is compatible with the host cell machinery, permitting amplification and/or expression of the gene can occur). In some embodiments, vectors are used that employ protein-fragment complementation assays using protein reporters, such as dihydrofolate reductase (see, for example, U.S. Pat. No. 6,270,964). Suitable expression vectors are known in the art and are also commercially available.

Typically, vectors used in host cells will contain sequences for plasmid maintenance and for cloning and expression of exogenous nucleotide sequences. Such sequences will typically include one or more of the following nucleotide sequences: a promoter, one or more enhancer sequences, an origin of replication, transcriptional and translational control sequences, a transcriptional termination sequence, a complete intron sequence containing a donor and acceptor splice site, various pre- or pro-sequences to improve glycosylation or yield, a native or heterologous signal sequence (leader sequence or signal peptide) for polypeptide secretion, a ribosome binding site, a polyadenylation sequence, internal ribosome entry site (IRES) sequences, an expression augmenting sequence element (EASE), tripartite leader (TPA) and VA gene RNAs from Adenovirus 2, a polylinker region for inserting the polynucleotide encoding the polypeptide to be expressed, and a selectable marker element. Vectors may be constructed from a starting vector such as a commercially available vector, additional elements may be individually obtained and ligated into the vector. Methods used for obtaining each of the components are well known to one skilled in the art.

Vector components may be homologous (i.e., from the same species and/or strain as the host cell), heterologous (e.g., from a species other than the host cell species or strain), hybrid (i.e., a combination of flanking sequences from more than one source), synthetic or native. The sequences of components useful in the vectors may be obtained by methods well known in the art, such as those previously identified by mapping and/or by restriction endonuclease. In addition, they can be obtained by polymerase chain reaction (PCR) and/or by screening a genomic library with suitable probes.

A ribosome-binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the polypeptide to be expressed.

An origin of replication aids in the amplification of the vector in a host cell. They may be included as part of commercially available prokaryotic vectors and may also be chemically synthesized based on a known sequence and ligated into the vector. Various viral origins (e.g., SV40, polyoma, adenovirus, vesicular stomatitus virus (VSV), or papillomaviruses such as HPV or BPV) are useful for cloning vectors in mammalian cells.

Transcriptional and translational control sequences for mammalian host cell expression vectors can be excised from viral genomes. Commonly used promoter and enhancer sequences are derived from polyoma virus, adenovirus 2, simian virus 40 (SV40), and human cytomegalovirus (CMV). For example, the human CMV promoter/enhancer of immediate early gene 1 may be used. See, e.g., Patterson et al., 1994, Applied Microbiol. Biotechnol. 40:691-98. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., 1978, Nature 273:113; Kaufman, 1990, Meth. in Enzymol. 185:487-511). Smaller or larger SV40 fragments can also be used, provided the approximately 250 bp sequence extending from the Hind III site toward the BgII site located in the SV40 viral origin of replication site is included.

A transcription termination sequence is typically located 3' to the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis known to those of skill in the art.

A selectable marker gene encoding a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex or defined media. Specific selectable markers are the kanamycin resistance gene, the ampicillin resistance gene, and the tetracycline resistance gene. Advantageously, a neomycin resistance gene may also be used for selection in both prokaryotic and eukaryotic host cells.

Other selectable genes may be used to amplify the gene that will be expressed. Amplification is the process wherein genes that are required for production of a protein critical for growth or cell survival are reiterated in tandem within the chromosomes of successive generations of recombinant cells. Examples of suitable selectable markers for mammalian cells include glutamine synthase (GS)/methionine sulfoximine (MSX) system, dihydrofolate reductase (DHFR), and promoterless thymidine kinase genes. Mammalian cell transformants are placed under selection pressure wherein only the transformants are uniquely adapted to survive by virtue of the selectable gene present in the vector. Selection pressure is imposed by culturing the transformed cells under conditions in which the concentration of selection agent in the medium is successively increased, thereby leading to the amplification of both the selectable gene and the DNA that encodes a protein of interest. As a result, increased quantities of a polypeptide of interest are synthesized from the amplified DNA.

In some cases, such as where glycosylation is desired in a eukaryotic host cell expression system, one may manipulate the various pre- or pro-sequences to improve glycosylation or yield. For example, one may alter the peptidase cleavage site of a particular signal peptide, or add prosequences, which also may affect glycosylation. The final protein product may have, in the −1 position (relative to the first amino acid of the mature protein), one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired polypeptide if the enzyme cuts at such area within the mature polypeptide.

Expression and cloning will typically contain a promoter that is recognized by the host organism and operably linked to the molecule encoding a protein of interest. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, uniformly transcribe a gene to which they are operably linked, that is, with little or no control over gene expression. A large number of promoters, recognized by a variety of potential host cells, are well known.

Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus, and Simian Virus 40 (SV40). Other suitable mammalian promoters include heterologous mammalian promoters, for example, heat-shock promoters and the actin promoter.

Additional promoters which may be of interest include, but are not limited to: SV40 early promoter (Benoist and Chambon, 1981, Nature 290:304-310); CMV promoter (Thomsen et al., 1984, Proc. Natl. Acad. U.S.A. 81:659-663); the promoter contained in the 3' long terminal repeat of Rous sarcoma virus (Yamamoto et al., 1980, Cell 22:787-797); herpes thymidine kinase promoter (Wagner et al., 1981, Proc. Natl. Acad. Sci. U.S.A. 78:1444-1445); glyceraldehyde-3-phosphate dehydrogenase (GAPDH); promoter and regulatory sequences from the metallothionine gene (Prinster et al., 1982, Nature 296:39-42); and prokaryotic promoters such as the beta-lactamase promoter (Villa-Kamaroff et al., 1978, Proc. Natl. Acad. Sci. U.S.A. 75:3727-3731); or the tac promoter (DeBoer et al., 1983, Proc. Natl. Acad. Sci. U.S.A. 80:21-25). Also of interest are the following animal transcriptional control regions, which exhibit tissue specificity and have been utilized in transgenic animals: the elastase I gene control region that is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); the insulin gene control region that is active in pancreatic beta cells (Hanahan, 1985, Nature 315:115-122); the immuno-globulin gene control region that is active in lymphoid cells (Grosschedl et al., 1984, Cell 38:647-658; Adames et al., 1985, Nature 318:533-538; Alexander et al., 1987, Mol. Cell. Biol. 7:1436-1444); the mouse mammary tumor virus control region that is active in testicular, breast, lymphoid and mast cells (Leder et al., 1986, Cell 45:485-495); the albumin gene control region that is active in liver (Pinkert et al., 1987, Genes and Devel. 1:268-276); the alpha-feto-protein gene control region that is active in liver (Krumlauf et al., 1985, Mol. Cell. Biol. 5:1639-1648; Hammer et al., 1987, Science 253:53-58); the alpha 1-antitrypsin gene control region that is active in liver (Kelsey et al., 1987, Genes and Devel. 1:161-171); the beta-globin gene control region that is active in myeloid cells (Mogram et al., 1985, Nature 315:338-340; Kollias et al., 1986, Cell 46:89-94); the myelin basic protein gene control region that is active in oligodendrocyte cells in the brain (Readhead et al., 1987, Cell 48:703-712); the myosin light chain-2 gene control region that is active in skeletal muscle (Sani, 1985, Nature 314:283-286); and the gonadotropic releasing hormone gene control region that is active in the hypothalamus (Mason et al., 1986, Science 234:1372-1378).

An enhancer sequence may be inserted into the vector to increase transcription by higher eukaryotes. Enhancers are cis-acting elements of DNA, usually about 10-300 bp in length, that act on the promoter to increase transcription. Enhancers are relatively orientation and position indepen-dent, having been found at positions both 5' and 3' to the transcription unit. Several enhancer sequences available from mammalian genes are known (e.g., globin, elastase, albumin, alpha-feto-protein and insulin). Typically, how-ever, an enhancer from a virus is used. The SV40 enhancer, the cytomegalovirus early promoter enhancer, the polyoma enhancer, and adenovirus enhancers known in the art are exemplary enhancing elements for the activation of eukary-otic promoters. While an enhancer may be positioned in the vector either 5' or 3' to a coding sequence, it is typically located at a site 5' from the promoter.

A sequence encoding an appropriate native or heterolo-gous signal sequence (leader sequence or signal peptide) can be incorporated into an expression vector, to promote extra-cellular secretion of the protein of interest. The choice of signal peptide or leader depends on the type of host cells in which the protein of interest to be produced, and a heter-ologous signal sequence can replace the native signal sequence. Examples of signal peptides that are functional in mammalian host cells include the following: the signal sequence for interleukin-7 described in U.S. Pat. No. 4,965, 195; the signal sequence for interleukin-2 receptor described in Cosman et al., 1984, Nature 312:768; the interleukin-4 receptor signal peptide described in EP Patent No. 0367 566; the type I interleukin-1 receptor signal peptide described in U.S. Pat. No. 4,968,607; the type II interleukin-1 receptor signal peptide described in EP Patent No. 0 460 846.

Additional control sequences shown to improve expres-sion of heterologous genes from mammalian expression vectors include such elements as the expression augmenting sequence element (EASE) derived from CHO cells (Morris et al., in Animal Cell Technology, pp. 529-534 (1997); U.S. Pat. Nos. 6,312,951 B1, 6,027,915, and 6,309,841 B1) and the tripartite leader (TPL) and VA gene RNAs from Adeno-virus 2 (Gingeras et al., 1982, J. Biol. Chem. 257:13475-13491). The internal ribosome entry site (IRES) sequences of viral origin allows dicistronic mRNAs to be translated efficiently (Oh and Sarnow, 1993, Current Opinion in Genet-ics and Development 3:295-300; Ramesh et al., 1996, Nucleic Acids Research 24:2697-2700).

Following construction, one or more vectors may be inserted into a suitable cell for amplification and/or poly-peptide expression. The transformation of an expression vector into a selected cell may be accomplished by well-known methods including transfection, infection, calcium phosphate co-precipitation, electroporation, nucleofection, microinjection, DEAE-dextran mediated transfection, cat-ionic lipids mediated delivery, liposome mediated transfec-tion, microprojectile bombardment, receptor-mediated gene delivery, delivery mediated by polylysine, histone, chitosan, and peptides. The method selected will in part be a function of the type of host cell to be used. These methods and other suitable methods are well known to the skilled artisan and are set forth in manuals and other technical publications, for example, in Sambrook et al., Molecular Cloning: A Labo-ratory Manual, 3rd ed., Cold Spring Harbor Laboratory Press, Cold Spring Harbor, N.Y. (2001).

The term "transformation" refers to a change in a cell's genetic characteristics, and a cell has been transformed when it has been modified to contain new DNA or RNA. For example, a cell is transformed where it is genetically modi-fied from its native state by introducing new genetic material via transfection, transduction, or other techniques.

Following transfection or transduction, the transforming DNA can recombine with that of the cell by physically integrating into a chromosome of the cell or can be main-tained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous DNA by a cell. A number of transfection tech-niques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197.

The term "transduction" refers to the process whereby foreign DNA is introduced into a cell via viral vector. See Jones et al., (1998). Genetics: principles and analysis. Bos-ton: Jones & Bartlett Publ.

A wide variety of mammalian cell lines suitable for growth in culture are available from the American Type Culture Collection (Manassas, Va.) and commercial ven-dors. Examples of cell lines commonly used in the industry include monkey kidney CV1 line transformed by SV40 (COS-7, ATCC CRL 1651); human embryonic kidney line (293 or 293 cells subcloned for growth in suspension culture, (Graham et al, 1977, J. Gen Virol. 36:59); baby hamster kidney cells (BHK, ATCC CCL 10); mouse Sertoli cells (TM4, Mather, 1980, Biol. Reprod. 23:243-251); mon-key kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., 1982, Annals N.Y Acad. Sci. 383:44-68); MRC 5 cells or FS4 cells; mammalian myeloma cells, and a number of other cell lines and Chinese hamster ovary (CHO) cells.

Large-scale production of proteins for commercial appli-cations is typically carried out in suspension culture. Therefore, mammalian host cells used to generate the recombinant mammalian cells described herein can, but need not be, adapted to growth in suspension culture. A variety of host cells adapted to growth in suspension culture are known, including mouse myeloma NS0 cells and CHO cells from CHO-S, DG44, and DXB11 cell lines. Other suitable cell lines include mouse myeloma SP2/0 cells, baby hamster kidney BF1K-21 cells, human PER.C6® cells, human embryonic kidney F1EK-293 cells, and cell lines derived or engineered from any of the cell lines disclosed herein.

CHO cells are widely used to produce complex recombinant proteins, including CHOK1 cells (ATCC CCL61). The dihydrofolate reductase (DHFR)-deficient mutant cell lines (Urlaub et al., 1980, Proc Natl Acad Sci USA 77: 4216-4220), DXB11 and DG-44, are desirable CHO host cell lines because the efficient DHFR selectable and amplifiable gene expression system allows high level recombinant protein expression in these cells (Kaufman R. J., 1990, Meth Enzymol 185:537-566). Also included are the glutamine synthase (GS)-knockout CHOK1SV cell lines, making use of glutamine synthetase (GS)-based methionine sulfoximine (MSX) selection. Other suitable CHO host cells could include, but are not limited to, the following (ECACC accession numbers in brackets): CHO (85050302), CHO (PROTEIN FREE) (00102307), CHO-K1 (85051005), CHO-K1/SF (93061607), CHO/dhfr-(94060607), CHO/dhfr-AC-free (05011002), RR-CHOK1 (92052129).

The production of a recombinant protein begins with establishing a mammalian cell production culture of cells that express the protein, in a culture plate, flask, tube, bioreactor or other suitable vessel. Smaller production bioreactors are typically used, in one embodiment the bioreactors are 500 L to 2000 L. In another embodiment, 1000 L-2000 L bioreactors are used. The seed cell density used to inoculate the bioreactor can have a positive impact on the level of recombinant protein produced. In one embodiment the bioreactor is inoculated with at least $0.5\times10^6$ up to and beyond $3.0\times10^6$ viable cells/mL in a serum-free culture medium. In another embodiment the inoculation is $1.0\times10^6$ viable cells/mL.

The mammalian cells then undergo an exponential growth phase. The cell culture can be maintained without supplemental feeding until a desired cell density is achieved. In one embodiment the cell culture is maintained for up to three days with or without supplemental feeding. In another embodiment the culture can be inoculated at a desired cell density to begin the production phase without a brief growth phase. In any of the embodiments herein the switch from the growth phase to production phase can also be initiated by any of the aforementioned methods.

At the transition between the growth phase and the production phase, and during the production phase, the percent packed cell volume (% PCV) is equal to or less than 35%. The desired packed cell volume maintained during the production phase is equal to or less than 35%. In one embodiment the packed cell volume is equal to or less than 30%. In another embodiment the packed cell volume is equal to or less than 20%. In yet another embodiment the packed cell volume is equal to or less than 15%. In a further embodiment the packed cell volume is equal to or less than 10%.

Three methods are typically used in commercial processes for the production of recombinant proteins by mammalian cell culture: batch culture, fed-batch culture, and perfusion culture. Batch culture is a discontinuous method where cells are grown in a fixed volume of culture media for a short period of time followed by a full harvest. Cultures grown using the batch method experience an increase in cell density until a maximum cell density is reached, followed by a decline in viable cell density as the media components are consumed and levels of metabolic by-products (such as lactate and ammonia) accumulate. Harvest typically occurs at the point when the maximum cell density is achieved (e.g., $5\times10^6$ cells/mL or greater, depending on media formulation, cell line, etc.). The batch process is the simplest culture method, however viable cell density is limited by the nutrient availability and once the cells are at maximum density, the culture declines and production decreases. There is no ability to extend a production phase because the accumulation of waste products and nutrient depletion rapidly lead to culture decline, (typically around 3 to 7 days).

Fed-batch culture improves on the batch process by providing bolus or continuous media feeds to replenish those media components that have been consumed. Since fed-batch cultures receive additional nutrients throughout the run, they have the potential to achieve higher cell densities ($>10$ to $30\times10^6$ cells/ml, depending on media formulation, cell line, etc.) and increased product titers, when compared to the batch method. Unlike the batch process, a biphasic culture can be created and sustained by manipulating feeding strategies and media formulations to distinguish the period of cell proliferation to achieve a desired cell density (the growth phase) from the period of suspended or slow cell growth (the production phase). As such, fed batch cultures have the potential to achieve higher product titers compared to batch cultures. Typically, a batch method is used during the growth phase and a fed-batch method used during the production phase, but a fed-batch feeding strategy can be used throughout the entire process. However, unlike the batch process, bioreactor volume is a limiting factor which limits the amount of feed. Also, as with the batch method, metabolic by-product accumulation will lead to culture decline, which limits the duration of the production phase, about 10 to 21 days. Fed-batch cultures are discontinuous, and harvest typically occurs when metabolic by-product levels or culture viability reach predetermined levels. When compared to a batch culture, in which no feeding occurs, a fed batch culture can produce greater amounts of recombinant protein. See, e.g., U.S. Pat. No. 5,672,502.

Perfusion methods offer potential improvement over the batch and fed-batch methods by adding fresh media and simultaneously removing spent media. Typical large scale commercial cell culture strategies strive to reach high cell densities, $60-90(+)\times10^6$ cells/mL where almost a third to over one-half of the reactor volume is biomass. With perfusion culture, extreme cell densities of $>1\times10^8$ cells/mL have been achieved and even higher densities are predicted. Typical perfusion cultures begin with a batch culture start-up lasting for a day or two followed by continuous, step-wise and/or intermittent addition of fresh feed media to the culture and simultaneous removal of spent media with the retention of cells and additional high molecular weight compounds such as proteins (based on the filter molecular weight cutoff) throughout the growth and production phases of the culture. Various methods, such as sedimentation, centrifugation, or filtration, can be used to remove spent media, while maintaining cell density. Perfusion flow rates of a fraction of a working volume per day up to many multiple working volumes per day have been reported.

An advantage of the perfusion process is that the production culture can be maintained for longer periods than batch or fed-batch culture methods. However, increased media preparation, use, storage and disposal are necessary to support a long-term perfusion culture, particularly those with high cell densities, which also need even more nutrients, and all of this drives the production costs even higher, compared to batch and fed batch methods.

In addition, higher cell densities can cause problems during production, such as maintaining dissolved oxygen levels and problems with increased gassing including supplying more oxygen and removing more carbon dioxide, which would result in more foaming and the need for alterations to antifoam strategies; as well as during harvest and downstream processing where the efforts required to remove the excessive cell material can result in loss of product, negating the benefit of increased titer due to increased cell mass.

Also provided is a large-scale cell culture strategy that combines fed batch feeding during the growth phase followed by continuous perfusion during the production phase. The method targets a production phase where the cell culture is maintained at a packed cell volume of less than or equal to 35%.

In one embodiment, a fed-batch culture with bolus feeds is used to maintain a cell culture during the growth phase. Perfusion feeding can then be used during a production phase. In one embodiment, perfusion begins when the cells have reached a production phase.

In another embodiment, perfusion begins on or about day 3 to on or about day 9 of the cell culture. In another embodiment perfusion begins on or about day 5 to on or about day 7 of the cell culture.

Using bolus feeding during the growth phase allows the cells to transition into the production phase, resulting in less dependence on a temperature shift as a means of initiating and controlling the production phase, however a temperature shift of about 36° C. to about 31° C. can take place between the growth phase and production phase. In one embodiment the shift is from 36° C. to 32° C.

As described herein, the bioreactor can be inoculated with at least $0.5 \times 10^6$ up to and beyond $3.0 \times 10^6$ viable cells/mL in a serum-free culture medium, for example $1.0 \times 10^6$ viable cells/mL.

Perfusion culture is one in which the cell culture receives fresh perfusion feed medium while simultaneously removing spent medium. Perfusion can be continuous, stepwise, intermittent, or a combination of any or all of any of these. Perfusion rates can be less than a working volume to many working volumes per day. The cells are retained in the culture and the spent medium that is removed is substantially free of cells or has significantly fewer cells than the culture. Recombinant proteins expressed by the cell culture can also be retained in the culture. Perfusion can be accomplished by a number of means including centrifugation, sedimentation, or filtration, See, e.g., Voisard et al., 2003, Biotechnology and Bioengineering 82:751-65. An example of a filtration method is alternating tangential flow filtration. Alternating tangential flow is maintained by pumping medium through hollow-fiber filter modules. See, e.g., U.S. Pat. No. 6,544,424; Furey, 2002, Gen. Eng. News. 22 (7):62-63.

"Perfusion flow rate" is the amount of media that is passed through (added and removed) from a bioreactor, typically expressed as some portion or multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

Cell cultures can be supplemented with concentrated feed medium containing components, such as nutrients and amino acids, which are consumed during the course of the production phase of the cell culture.

Concentrated feed medium may be based on just about any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal amount. Concentrated feed media are often used in fed batch culture processes.

The method described herein may be used to improve the production of recombinant proteins in multiple phase culture processes. In a multiple stage process, cells are cultured in two or more distinct phases. For example, cells may be cultured first in one or more growth phases, under environmental conditions that maximize cell proliferation and viability, then transferred to a production phase, under conditions that maximize protein production. In a commercial process for production of a protein by mammalian cells, there are commonly multiple, for example, at least about 2, 3, 4, 5, 6, 7, 8, 9, or 10 growth phases that occur in different culture vessels preceding a final production culture.

The growth and production phases may be preceded by, or separated by, one or more transition phases. In multiple phase processes, the method according to the present invention can be employed at least during the growth and production phase of the final production phase of a commercial cell culture, although it may also be employed in a preceding growth phase. A production phase can be conducted at large scale. A large-scale process can be conducted in a volume of at least about 100, 500, 1000, 2000, 3000, 5000, 7000, 8000, 10,000, 15,000, 20,000 liters. In one embodiment production is conducted in 500 L, 1000 L and/or 2000 L bioreactors.

A growth phase may occur at a higher temperature than a production phase. For example, a growth phase may occur at a first temperature from about 35° C. to about 38° C., and a production phase may occur at a second temperature from about 29° C. to about 37° C., optionally from about 30° C. to about 36° C. or from about 30° C. to about 34° C. In addition, chemical inducers of protein production, such as, for example, caffeine, butyrate, and hexamethylene bisacetamide (HMBA), may be added at the same time as, before, and/or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Samples from the cell culture can be monitored and evaluated using any of the analytical techniques known in the art. A variety of parameters including recombinant protein and medium quality and characteristics can be monitored for the duration of the culture. Samples can be taken and monitored intermittently at a desirable frequency, including continuous monitoring, real time or near real time.

Typically, the cell cultures that precede the final production culture (N-x to N-1) are used to generate the seed cells that will be used to inoculate the production bioreactor, the N-1 culture. The seed cell density can have a positive impact on the level of recombinant protein produced. Product levels tend to increase with increasing seed density. Improvement in titer is tied not only to higher seed density, but is likely to be influenced by the metabolic and cell cycle state of the cells that are placed into production.

Seed cells can be produced by any culture method. One such method is a perfusion culture using alternating tangential flow filtration. An N-1 bioreactor can be run using alternating tangential flow filtration to provide cells at high density to inoculate a production bioreactor. The N-1 stage may be used to grow cells to densities of >90×10⁶ cells/mL. The N-1 bioreactor can be used to generate bolus seed cultures or can be used as a rolling seed stock culture that could be maintained to seed multiple production bioreactors at high seed cell density. The duration of the growth stage of production can range from 7 to 14 days and can be designed so as to maintain cells in exponential growth prior to inoculation of the production bioreactor. Perfusion rates, medium formulation and timing are optimized to grow cells and deliver them to the production bioreactor in a state that is most conducive to optimizing their production. Seed cell densities of >15×10⁶ cells/mL can be achieved for seeding production bioreactors. Higher seed cell densities at inoculation can decrease or even eliminate the time needed to reach a desired production density.

The invention also provides pharmaceutical compositions comprising any of the polypeptide variants of neuregulin or polynucleotides encoding the polypeptide variants described herein and a pharmaceutically acceptable excipient or carrier. As used herein, "pharmaceutically acceptable excipient or carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000). Typically, an appropriate amount of a pharmaceutically-acceptable salt is used in the formulation to render the formulation isotonic. Examples of the carrier include saline, Ringer's solution and dextrose solution. The pH of the solution is preferably from about 5 to about 8, and more preferably from about 7 to about 7.5. Further carriers include sustained release preparations such as semipermeable matrices of Solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of the polypeptide and the polynucleotide being administered.

Methods of Using Neuregulin Variants

The invention also provides methods for preventing, treating, or delaying development of diseases in an individual comprising administering to an individual a pharmaceutical composition comprising a polypeptide variant of neuregulin described herein via activating ErbB2/ErbB4 receptors.

A neuregulin variant according to the invention can also be used to treat muscle cells and medical conditions affecting muscle cells. In particular, such neuregulin variant can be useful for treating muscle damage, decreasing atrophy of muscle cells, and increasing muscle cell survival, proliferation and/or regeneration. Examples of pathophysiological conditions of the musculature amenable to treatment with a neuregulin variant include skeletal muscle diseases (e.g., myopathy or dystrophy), cardiac muscle disorders (including atrial cardiac arrhythmias, cardiomyopathy, ischemic damage, congenital disease, and cardiac trauma), and smooth muscle disorders (such as arterial sclerosis, vascular lesion, or congenital vascular disease). A neuregulin variant can also be employed to reduce hypertension and to increase functional acetylcholine receptors on muscle cells (e.g., in individuals having myasthenia gravis or tachycardia).

The term "treating cardiovascular disease" as used herein, unless otherwise indicated, means inhibiting, suppressing, delaying, reversing, or alleviating, either partially or completely, the onset of a cardiovascular disease or condition in a subject, or the progression of a pre-existing cardiovascular disease or condition, or a symptom thereof, in a subject. Non-limiting examples of cardiovascular diseases that can be treated by the methods of the disclosure include chronic heart failure, congestive heart failure (CHF), acute heart failure, myocardial infarction (MI), left ventricular systolic dysfunction, reperfusion injury associated with MI, chemotherapy-induced cardiotoxicity (adult or pediatric), radiation-induced cardiotoxicity, adjunct to surgical intervention in pediatric congenital heart disease. Non limiting examples of symptoms of cardiovascular disease include shortness of breath, cough, rapid weight gain, swelling in legs, ankles and abdomen, dizziness, fatigue, weakness, dizziness, chest pain, fainting (syncope), tachycardia and bradycardia. Methods of determining the progression of cardiovascular disease and the effectiveness of treatment will be readily apparent to one of ordinary skill in the art. For example, the progression of various cardiovascular diseases can be determined by ejection fraction/electrocardiogram (ECG), ECG/Holter monitoring, stress test, cardiac catheterization, cardiac computerized tomography (CT) scan and cardiac magnetic resonance imaging (MRI).

In certain embodiments, the cardiovascular diseases that can be prevented, treated, or delayed for development via preferentially activating ErbB2/ErbB4 receptors include, but are not limited to, heart failure, myocardial infarction, dilated or hypertrophic cardiomyopathy, and myocarditis (e.g., viral myocarditis), cardiac toxicity.

As used herein, an "individual" or "subject" is a mammal, more preferably a human. Mammals include, but are not limited to, farm animals (such as cows, pigs, sheep, goats), sport animals, pets (such as cats, dogs, horses), primates, mice and rats.

According to the present invention, a polypeptide variant of neuregulin-1 described herein, or a nucleic acid encoding a polypeptide variant, alone or in combination with other agents, carriers or excipients, may be formulated for any suitable administration route such as subcutaneous injection, intravenous injection, intramuscular injection, intradermal injection, oral or topical administration. The method may employ formulations for injectable administration in unit dosage form, in ampules or in multidose containers, with an added preservative. The formulations may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, sterile pyrogen-free water or other solvents, before use. Topical administration in the present invention may employ the use of a foam, gel, cream, ointment, transdermal patch, or paste.

The magnitude of a therapeutic dose in the treatment or prevention will vary with the type and severity of the condition to be treated and the route of administration. The dose, and perhaps dose frequency, will also vary according to age, body weight, condition and response of the individual patient. It should be noted that the attending physician would know how to and when to terminate, interrupt or adjust therapy to lower dosage due to toxicity, or adverse effects. Conversely, the physician would also know how to and when to adjust treatment to higher levels if the clinical response is not adequate (precluding toxic side effects).

The dosage of a neuregulin variant composition to be employed therapeutically depends, for example, upon the therapeutic objectives, the route of administration, and the condition of the patient. Accordingly, it is necessary for the clinician to titer the dosage and modify the route of administration as required to obtain the optimal therapeutic effect. A typical daily dosage can range from about 1 µg/kg to up to 100 mg/kg of body weight or more per day, but is typically between about 10 µg/kg/day to 10 mg/kg/day. Generally, the clinician begins with a low dosage of a pharmaceutical neuregulin variant composition and increases the dosage until the desired therapeutic effect is achieved.

In practical use, a polypeptide variant of neuregulin, a fusion protein comprising a polypeptide variant of neuregulin, or a nucleic acid encoding either of the foregoing, alone or in combination with other agents, may be combined as the active agent in intimate admixture with a pharmaceutical carrier or excipient, such as beta-cyclodextrin and 2-hydroxy-propyl-beta-cyclodextrin, according to conventional pharmaceutical compounding techniques. The carrier may take a wide form of preparation desired for administration, topical or parenteral.

In preparing compositions for parenteral dosage form, such as intravenous injection or infusion, similar pharmaceutical media may be employed, water, glycols, oils, buffers, sugar, preservatives, liposomes, and the like known to those of skill in the art. Examples of such parenteral compositions include, but are not limited to dextrose 5% w/v, normal saline or other solutions. The total dose of the polypeptide variant of neuregulin-1, or a nucleic acid encoding the polypeptide variant, alone or in combination with other agents to be administered may be administered in a vial of intravenous fluid, ranging from about 1 ml to 2000 ml. The volume of dilution fluid will vary according to the total dose administered.

Furthermore, a neuregulin variant can be capable of, enhancing the survival, proliferation, and or differentiation of cells having suitable ErbB receptors. The phrase "enhancing survival of cells" refers to increasing the period of existence of cells, either in vitro or in vivo, relative to the period of existence of cells that have not been exposed to the neuregulin variant ("untreated cells").

The expression "enhancing proliferation of cells" means increasing the rate or number of mitotic divisions, either in vitro or in vivo, relative to untreated cells. An increase in cell proliferation in cell culture can be detected by counting the number of cells before and after exposure to the neuregulin variant or by microscopic examination of the degree of confluency. Cell proliferation can also be quantified by measuring $^3$H-thymidine uptake by the cells.

The phrase "enhancing differentiation of cells" refers to increasing the extent of cell specialization. Cell specialization is characterized by the acquisition of one or more characteristics that differ from those of the original cells. Thus, the extent of cell specialization is typically determined by screening for a change in the phenotype of the cell (e.g., identifying a change in cellular morphology).

The present invention is not to be limited in scope by the specific embodiments described herein that are intended as single illustrations of individual aspects of the invention, and functionally equivalent methods and components are within the scope of the invention.

Indeed, various modifications of the invention, in addition to those shown and described herein will become apparent to those skilled in the art from the foregoing description and accompanying drawings. Such modifications are intended to fall within the scope of the appended claims.

EXAMPLES

Example 1: Yeast Display Engineering and Generation of NRG Variants

The neuregulin variant sequences were displayed on the surface of yeast through a fusion to alpha agglutinin. The degenerate codons were introduced at structurally identified positions to alternate between NRG1 and NRG4 sequences or full 20 amino acid randomization through use of an NNK codon. Three visualization markers were used for selection of binding competent/selective sequences. The first was an anti-HA antibody conjugated to Brilliant Violet 421 to measure surface display levels of neuregulin variants. The second was soluble recombinant ErbB3 receptor ECD conjugated to Alexafluor 488 for negative selection. The third was soluble recombinant ErbB4 receptor ECD conjugated to Alexafluor 647 for positive selection. Multiple rounds of positive sorting with constant ErbB4 concentrations (2.5 nM) and negative sorting against increasing ErbB3 concentrations (250, 500, 750 nM) resulted in obtaining selective neuregulin variants. Selected neuregulin variants were cloned into mammalian expression vectors using standard golden gate cloning methods from gblock DNAs. Final constructs incorporated various NRG domain truncation points, a variety of linkers, and different fusion domains and tags (Fc, scFc, 6×his) as shown in Table 1. Stable expression was done using standard lipofectamine methods into a suspension adapted CHO K1 cell line under puromycin selection. After a 7-day production, proteins from filtered condition media were purified through a triple tandem LFAS system (ProA, In Line Dilution, SEC) or a serial individual column method of ProA (or NiNTA for 6×his tagged proteins), Buffer exchange, CIEX, and/or HIC followed by a formulation into a 10 mM acetate 9% sucrose pH 5.2 buffer. Protein concentration was determined by A280.

In Vitro Phosphorylation of Akt in Neonatal Rat Cardiomyocytes and Rat Schwann Cells by Neuregulin Variants Specificity of neuregulin variants towards cardiomyocytes (ErbB4) versus Schwann cells (ErbB3) was tested by measuring Akt activity generated by formation of the ErbB2/ErbB4 and ErbB2/ErbB3 complexes. Upon activation by neuregulin, the ErbB4 and ErbB3 receptors dimerize preferentially with the ErbB2 co-receptor, forming the ErbB2/ErbB4 complex in cardiomyocytes and the ErbB2/ErbB3 complex in Schwann cells, both of which signal through the Akt pathway. Neonatal rat cardiomyocytes were isolated from hearts of Sprague Dawley rat pups at 0 to 4 days old according to manufacturer's protocol using the Neomyt kit and plated on Surecoat plates in NS media containing serum (all from Cellutron Life Technologies, Baltimore, MD). Rat Schwann cells were plated in Poly-D-Lysine coated plates with Dulbecco's modified Eagle's media (DMEM) supplemented with fetal bovine serum (Thermo Fisher) and forskolin (Millipore Sigma).

After a 24-hour incubation in a humidified incubator maintained at 37° C. and 5% $CO_2$, cardiomyocytes and Schwann cells were washed with serum free media and incubated an additional 16 hours in DMEM supplemented with bovine serum albumin (Sigma). Both cell lines were then treated with titrations of the neuregulin variant molecules for 15 minutes, upon which cells were lysed in lysis buffer (Meso Scale Discovery (MSD)). For detection of Akt phosphorylation, lysates were added to the Multi-Spot 96-Well 4-Spot Phospho (Serine 473)/Total Akt plates (MSD), incubated according to the manufacturer's protocol and read in the SECTOR Imager 6000 (MSD). For both cell assays, the percent phosphorylation of Akt was calculated by multiplying the phospho Akt signal by 2, then dividing by the phospho Akt signal added to the total Akt signal and then multiplying by 100. The phosphorylation of Akt data points were fitted using a log (agonist) versus response, variable slope (4 parameters) analysis in GraphPad Prism to generate $EC_{50}$ curves. The CM % agonism reflect the top value of the data points.

The results are presented in Table 3 below.

TABLE 3

| | Cardiomyocyte (CM) (ErbB4) Avg $EC_{50}$ (M) | Schwann cells (SC) (ErbB3) Avg $EC_{50}$ (M) | Selectivity SC/CM | CM % Agonism AVG | SEQ ID NO: |
|---|---|---|---|---|---|
| huNRG1(S177-F229)(NRGE1C)::3x(G4Q)::huFcSEFL2 (Pb) | 3.30E−10 | >1E−5 | >10000 | 77.3 | 1 |
| huNRG1(S177-F229)(NRGE1C)::1KmodT482V, M493L)::huFcSEFL2 (Pb) | 4.00E−10 | >1E−5 | >10000 | 75.8 | 2 |
| huNRG1(S177-F229)(NRGE1C): (G4A)2:G4::huFcSEFL2 (Pb) | 4.90E−10 | >1E−5 | >10000 | 82.7 | 3 |
| huNRG1(S177-F229)(NRGE1C)((G4E)2)::G4::huFcSEFL2 (Pb) | 3.60E−10 | >1E−5 | >10000 | 81.9 | 4 |
| huNRG1(S177-F229)(NRGE1C)::(G4S)2::G4::huFcSEFL2 (Pb) | 6.20E−10 | >1E−5 | >10000 | 79.4 | 5 |
| huNRG1(S177-F229)(NRGE1C)(G4E)::G4S::G4::huFcSEFL2 (Pb) | 4.20E−10 | >1E−5 | >10000 | 82.2 | 6 |
| huNRG1(S177-F229)(NRGE1C)(NRGmod)::G4::huFcSEFL2 (Pb) | 8.70E−10 | >1E−5 | >10000 | 75.5 | 7 |
| huNRG1(S177-F229)(NRGE1D)::3x(G4Q)::huFcSEFL2 (Pb) | 2.90E−10 | 4.10E−07 | 1401 | 74.4 | 8 |
| huNRG1(S177-F229)(NRGE1D)::1KmodT482V, M493L)::huFcSEFL2 (Pb) | 3.40E−10 | >1E−5 | >10000 | 83.4 | 9 |
| huNRG1(S177-F229)(NRGE1D)::(G4A)2:G4::huFcSEFL2 (Pb) | 3.20E−10 | >1E−5 | >10000 | 78.8 | 10 |
| huNRG1(S177-F229)(NRGE1D)((G4E)2)::G4::huFcSEFL2 (Pb) | 2.80E−10 | >1E−5 | >10000 | 84.6 | 11 |
| huNRG1(S177-F229)(NRGE1D)::(G4S)2::G4::huFcSEFL2 (Pb) | 4.60E−10 | >1E−5 | >10000 | 80.5 | 12 |
| huNRG1(S177-F229)(NRGE1D)(G4E)::G4S::G4::huFcSEFL2 (Pb) | 3.50E−10 | >1E−5 | >10000 | 85 | 13 |
| huNRG1(S177-F229)(NRGE1D)(NRGmod)::G4::huFcSEFL2 (Pb) | 5.40E−10 | >1E−5 | >10000 | 74.9 | 14 |
| Wild-type as control | 2.80E−10 | 2.70E−10 | 1 | 100 | |
| huNRG1(S177-Q237)(3H8)::3xG4S::huFcSEFL2 (Pb) | 2E−10 | >1E−5 | >10000 | | 15 |
| huNRG1(S177-F229)(3H8)::3x(G4Q)::huFcSEFL2 (Pb) | 2.8E−10 | 1.49E−7 | 527 | | 16 |
| huNRG1(S177-Q237)(3H8)::3x(G4Q)::huFcSEFL2 (Pb) | 2.4E−10 | 1E−7 | 414 | | 17 |
| huNRG1(S177-S228)(3H8)::3x(G4Q)::huFcSEFL2 (Pb) | 4.35E−08 | 2.77E−8 | 0.6 | | 18 |
| huNRG1(S177-Q237)(NRGE1C)::GG::huFcSEFL2 (Pb) | 4.1E−10 | >1E−5 | >10000 | | 19 |
| huNRG1(S177-F229)(NRGE1C)::3x(G4Q)::huFcSEFL2 (Pb) | 2.4E−10 | >1E−5 | >10000 | | 1 |
| huNRG1(S177-Q237)(NRGE1C)::3x(G4Q)::huFcSEFL2 (Pb) | 2.2E−10 | >1E−5 | >10000 | | 20 |
| huNRG1(S177-S228)(NRGE1C)::3x(G4Q)::huFcSEFL2 (Pb) | 1.48E−08 | 7.83E−7 | 53 | | 21 |
| huNRG1(S177-Q237)(NRGE1D)::GG::huFcSEFL2 (Pb) | 3.3E−10 | >1E−5 | >10000 | | 22 |
| huNRG1(S177-F229)(NRGE1D)::3x(G4Q)::huFcSEFL2 (Pb) | 3E−10 | 4.46E−7 | 1491 | | 8 |
| huNRG1(S177-Q237)(NRGE1D)::3x(G4Q)::huFcSEFL2 (Pb) | 2.1E−10 | >1E−5 | >10000 | | 23 |
| huNRG1(S177-S228)(NRGE1D)::3x(G4Q)::huFcSEFL2 (Pb) | 2.29E−07 | >1E−5 | >100 | | 24 |
| huNRG1(S177-Q237)(wt)::GG::huFcSEFL2 (Pb) | 6E−10 | 1.5E−10 | 0.3 | | 25 |
| huNRG1(S177-F229)(wt)::3x(G4Q)::huFcSEFL2 (Pb) | 3.4E−10 | 1E10 | 0.3 | | 26 |
| huNRG1(S177-Q237)(wt)::3x(G4Q)::huFcSEFL2 (Pb) | 2.1E−10 | 7E−11 | 0.3 | | 27 |
| huNRG1(S177-S228)(wt)::3x(G4Q)::huFcSEFL2 (Pb) | 2.6E−9 | 7E−11 | 0.03 | | 28 |
| huNRG1(S177-Q237)(NRGE1A)::GG::huFcSEFL2 (Pb) | 1.84E−09 | >1E−05 | >5500 | 72 | 29 |
| huNRG1(S177-Q237)(NRGE1B)::GG::huFcSEFL2 (Pb) | 1.48E−09 | >1E−05 | >6700 | 76 | 30 |
| huNRG1(S177-Q237)(NRGE1C)::GG::huFcSEFL2 (Pb) | 4.76E−10 | >1E−05 | >10000 | 82 | 19 |
| huNRG1(S177-Q237)(NRGE1D)::GG::huFcSEFL2 (Pb) | 3.03E−10 | >1E−05 | >10000 | 83 | 22 |
| huNRG1(S177-Q237)(NRGE1E)::GG::huFcSEFL2 (Pb) | 9.95E−10 | >1E−05 | >10000 | 83 | 31 |
| huNRG1(S177-Q237)(NRGE1F)::GG::huFcSEFL2 (Pb) | 6.50E−10 | >1E−05 | >10000 | 90 | 32 |
| huNRG1(S177-Q237)(NRGE1G)::GG::huFcSEFL2 (Pb) | 2.18E−10 | >1E−05 | >10000 | 84 | 33 |
| huNRG1(S177-Q237)(NRGE1H)::GG::huFcSEFL2 (Pb) | 2.86E−10 | >1E−05 | >10000 | 88 | 34 |
| huNRG1(S177-Q237)(NRGE1I)::GG::huFcSEFL2 (Pb) | 2.29E−08 | >1E−05 | 437 | 67 | 35 |
| huNRG1(S177-Q237)(NRGEU)::GG::huFcSEFL2 (Pb) | 1.41E−08 | >1E−05 | 710 | 68 | 36 |
| huNRG1(S177-Q237)(NRGE1K)::GG::huFcSEFL2 (Pb) | 7.54E−09 | >1E−05 | 1320 | 66 | 37 |
| huNRG1(S177-Q237)(NRGE1L)::GG::huFcSEFL2 (Pb) | 2.29E−09 | >1E−05 | >4370 | 74 | 38 |
| huNRG1(S177-Q237)(NRGE1M)::GG::huFcSEFL2 (Pb) | 2.56E−08 | 1.01E−06 | 39 | 30 | 39 |
| huNRG1(S177-Q237)(NRGE1N)::GG::huFcSEFL2 (Pb) | 1.73E−09 | 7.51E−07 | 435 | 26 | 40 |
| huNRG1(S177-Q237)(NRGE1O)::GG::huFcSEFL2 (Pb) | 1.04E−09 | 5.46E−07 | 526 | 27 | 41 |
| huNRG1(S177-Q237)(NRGE1P)::GG::huFcSEFL2 (Pb) | 2.22E−09 | 5.10E−07 | 229 | 28 | 42 |
| Wild-type as control | 2.53E−10 | 6.52E−10 | 2.6 | 100 | |
| huNRG1(S177-Q237)(1D3)::GG::huFcSEFL2 (Pb) | 1.62E−09 | >1E−5 | >6170 | 78 | 43 |
| huNRG1(S177-F229)(NRGE1C) (D48T_F49Q_M50I) huIgG1z SELF2 Fc | 2.4E−10 | 1E−5 | >10000 | 83.6 | 44 |
| huNRG1(S177-F229)(NRGE1C) (E47A_D48P_F49H_M50I) huIgG1z SELF2 Fc | 2.3E−10 | 1E−5 | >10000 | 85.8 | 45 |
| huNRG1(S177-F229)(NRGE1C) (E47K_48T_F49S_M50L) huIgG1z SELF2 Fc | 2.5E−10 | 1E−5 | >10000 | 92.9 | 46 |
| huNRG1(S177-F229)(NRGE1C) (E47Q_D48S_M50P) huIgG1z SELF2 Fc | 3E−10 | 1E−5 | >10000 | 83.2 | 47 |

TABLE 3-continued

| | Cardiomyocyte (CM) (ErbB4) Avg EC$_{50}$ (M) | Schwann cells (SC) (ErbB3) Avg EC$_{50}$ (M) | Selectivity SC/CM | CM % Agonism AVG | SEQ ID NO: |
|---|---|---|---|---|---|
| huNRG1(S177-F229)(NRGE1C) (E47S_D48A_F49L_M50T) huIgG1z SELF2 Fc | 4.8E−10 | 1E−5 | >10000 | 87.8 | 48 |
| huNRG1(S177-F229)(NRGE1C) (E47S_D48T_F49R_M50V) huIgG1z SELF2 Fc | 1.9E−10 | 1E−5 | >10000 | 76 | 49 |
| huNRG1(S177-F229)(NRGE1C) huIgG1z SELF2 Fc | 2.8E−10 | 1E−5 | >10000 | 77.2 | 50 |
| huNRG1(S177-F229)(NRGE1D) (E47K_D48L_F49D_M50I) huIgG1z SELF2 Fc | 1.5E−10 | 9.33E−09 | 62.2 | 88.5 | 51 |
| huNRG1(S177-F229)(NRGE1D) (E47S_D48S_F49E_M50L) huIgG1z SELF2 Fc | 3.7E−10 | 1E−5 | >10000 | 86.3 | 52 |
| huNRG1(S177-F229)(NRGE1D) (E47T_D48S_F49L_M50L) hnIgG1z SELF2 Fc | 3.9E−10 | 1E−5 | >10000 | 79.5 | 53 |
| huNRG1(S177-F229)(NRGE1D) huIgG1z SELF2 Fc | 4.8E−10 | 1E−5 | >10000 | 82.2 | 54 |
| huNRG1(S177-F229) huIgG1z SELF2 Fc | 3.1E−10 | 1.4E−10 | 0.45161 | 91.4 | 55 |
| huNRG1(S177-F229)(NRGE1C) 6xHis | 1.444E−09 | 1E−5 | >10000 | 106 | 56 |
| huNRG1(S177-F229)(NRGE1C) (D48T_F49Q_M50I) 6xHis | 7.123E−10 | 1E−5 | >10000 | 105.7 | 57 |
| huNRG1(S177-F229)(NRGE1C) (E47A_D48P_F49H_M50I) 6xHis | 1.104E−09 | 1E−5 | >10000 | 96.47 | 58 |
| huNRG1(S177-F229)(NRGE1C) (E47K_D48T_F49S_M50L) 6xHis | 8.251E−10 | 1E−5 | >10000 | 91.82 | 59 |
| huNRG1(S177-F229)(NRGE1C) (E47Q_D48S_M50P) 6xHis | #N/A | #N/A | #N/A | #N/A | 60 |
| huNRG1(S177-F229)(NRGE1C) (E47S_D48A_F49L_M50T) 6xHis | 6.948E−10 | 1E−5 | >10000 | 85.89 | 61 |
| huNRG1(S177-F229)(NRGE1C) (E47S_D48T_F49R_M50V) 6xHis | 5.795E−10 | 1E−5 | >10000 | 87.47 | 62 |
| huNRG1(S177-F229)(NRGE1D) 6xHis | 3.896E−10 | 1E−5 | >10000 | 90.65 | 63 |
| huNRG1(S177-F229)(NRGE1D) (E47K_D48L_F49D_M50I) 6xHis | 3.11E−10 | 1.723E−08 | 55.4019 | 91.65 | 64 |
| huNRG1(S177-F229)(NRGE1D) (E47S_D48S_F49E_M50L) 6xHis | 5.572E−10 | 1E−5 | >10000 | 96.05 | 65 |
| huNRG1(S177-F229)(NRGE1D) (E47T_D48S_F49L_M50L) 6xHis | 3.295E−10 | 1E−5 | >10000 | 99.83 | 66 |
| huNRG1(S177-F229)(NRGE1D) (E47V_D48T_F49R_M50L) 6xHis | 2.24E−10 | 1E−5 | >10000 | 97.95 | 67 |
| huNRG1(S177-F229) 6xHis | 5.865E−10 | 3.616E−9 | 6.16539 | 97.51 | 68 |
| :huFcSEFL2(desK):G4SG4:huNRG1(S177-F229)(NRGE1C) | 2.90E−10 | inactive | >10000 | 71.8 | 69 |
| :huFcSEFL2(desK):G4SG4:huNRG1(S177-F229)(NRGE1D) | 2.30E−10 | inactive | >10000 | 76.2 | 70 |
| :huFcSEFL2(desK):G4SG4:huNRG1(S177-Q237)(NRGEIC) | 1.10E−10 | inactive | >10000 | 84.9 | 71 |
| :huFcSEFL2(desK):G4SG4:huNRG1(S177-Q237)(NRGEID) | 1.00E−10 | inactive | >10000 | 90.5 | 72 |
| :huFcSEFL2(desK)vl31(+):G4SG4:huNRG1(S177-F229)(NRGE1C) | 6.40E−09 | inactive | >10000 | 62.7 | 73 |
| :huFcSEFL2(desK)vl31(+):G4SG4:huNRG1(S177-F229)(NRGE1D) | 4.30E−09 | inactive | >10000 | 72.3 | 74 |
| :huFcSEFL2(desK)vl31(+):G4SG4:huNRG1(S177-Q237)(NRGE1C) | 3.00E−10 | inactive | >10000 | 85.4 | 75 |
| :huFcSEFL2(desK)vl31(+):G4SG4:huNRG1(S177-Q237)(NRGE1D) | 2.30E−10 | inactive | >10000 | 88.7 | 76 |
| :huNRG1(S177-F229)(NRGE1C)::2X(G4A)G4::huFcSEFL2v131(+) | 3.40E−09 | inactive | >10000 | 91.6 | 77 |
| :huNRG1(S177-F229)(NRGE1C)::2X(G4E)G4::huFcSEFL2v131(+) | 2.90E−09 | inactive | >10000 | 94 | 78 |
| :huNRG1(S177-F229)(NRGE1D)::2X(G4A)G4::huFcSEFL2v131(+) | 2.00E−09 | inactive | >10000 | 87.1 | 79 |
| :huNRG1(S177-F229)(NRGE1D)::2X(G4E)G4::huFcSEFL2v131(+) | 1.90E−09 | inactive | >10000 | 91.9 | 80 |
| Wild-type as control | 1.50E−10 | 3.18E−10 | 2.12 | 100 | |
| huNRG1(S177-S228)(wt)((G4E)2:G4)::huFcSEFL2 (Pb) | 8.40E−11 | 2.22E−11 | 0.26429 | 92.6 | 81 |
| huNRG1(S177-F229)(NRGE1C)((G4E)2, GGT -> GGC silent mutation before terminal lysine)::G4::huFcSEFL2 | 7.30E−11 | inactive | >10000 | 88.7 | 4 |
| huNRG1(S177-F229)(NRGE1D)((G4E)2:G4)::huFcSEFL2 (Pb) | 7.90E−11 | inactive | >10000 | 88.2 | 11 |
| huNRG1(S177-Q237)(1A1)::GG::huFcSEFL2 (Pb) | 1.33E−10 | 9.11E−09 | 69 | Full | 82 |
| huNRG1(S177-Q237)(1A12)::GG::huFcSEFL2 (Pb) | 7.22E−10 | 4.79E−08 | 66 | Full | 83 |
| huNRG1(S177-Q237)(1A7)::GG::huFcSEFL2 (Pb) | 6.19E−10 | 1.00E−06 | 1616 | Full | 84 |
| huNRG1(S177-Q237)(1B4)::GG::huFcSEFL2 (Pb) | 9.96E−10 | 1.00E−05 | >10000 | Full | 85 |
| huNRG1(S177-Q237)(1B9)::GG::huFcSEFL2 (Pb) | 1.92E−09 | 1.00E−06 | 520 | Partial (<50%) | 86 |
| huNRG1(S177-Q237)(1C11)::GG::huFcSEFL2 (Pb) | 1.10E−09 | 8.70E−08 | 79 | Full | 87 |
| huNRG1(S177-Q237)(1D10)::GG::huFcSEFL2 (Pb) | 7.41E−10 | >3E−6 | >4000 | Full | 88 |
| huNRG1(S177-Q237)(1D3)::GG::huFcSEFL2 (Pb) | 7.72E−10 | 1.00E−05 | >10000 | Full | 43 |
| huNRG1(S177-Q237)(1D4)::GG::huFcSEFL2 (Pb) | 9.24E−10 | 2.26E−07 | 245 | Full | 89 |
| huNRG1(S177-Q237)(1D4)::GG::huFcSEFL2 (Pb) | 5.76E−10 | 3.23E−08 | 56 | Full | 89 |
| huNRG1(S177-Q237)(2E3)::GG::huFcSEFL2 (Pb) | 6.58E−10 | 1.00E−06 | 1521 | Partial (<50%) | 90 |
| huNRG1(S177-Q237)(2E4)::GG::huFcSEFL2 (Pb) | 4.29E−10 | 6.15E−08 | 143 | Full | 91 |
| huNRG1(S177-Q237)(2F2)::GG::huFcSEFL2 (Pb) | 2.44E−10 | 2.02E−07 | 826 | Full | 92 |
| huNRG1(S177-Q237)(2G3)::GG::huFcSEFL2 (Pb) | 2.08E−10 | 6.08E−08 | 292 | Full | 93 |
| huNRG1(S177-Q237)(2G4)::GG::huFcSEFL2 (Pb) | 2.42E−09 | 1.00E−06 | 414 | Partial (<50%) | 94 |
| huNRG1(S177-Q237)(2H7)::GG::huFcSEFL2 (Pb) | 3.00E−10 | 1.10E−07 | 368 | Partial (<50%) | 95 |
| huNRG1(S177-Q237)(3A7)::GG::huFcSEFL2 (Pb) | 3.66E−10 | 4.65E−08 | 127 | Partial (<50%) | 96 |
| huNRG1(S177-Q237)(3B8)::GG::huFcSEFL2 (Pb) | 1.40E−09 | 3.00E−06 | 2147 | Partial (<50%) | 97 |
| huNRG1(S177-Q237)(3D6)::GG::huFcSEFL2 (Pb) | 2.60E−09 | >1E−5 | >3800 | Partial (<50%) | 98 |
| huNRG1(S177-Q237)(3D8)::GG::huFcSEFL2 (Pb) | 5.10E−10 | >3E−6 | >5800 | Partial (<50%) | 99 |
| huNRG1(S177-Q237)(3E6)::GG::huFcSEFL2 (Pb) | 3.50E−10 | >1E−5 | >10000 | Full | 100 |

TABLE 3-continued

| | Cardiomyocyte (CM) (ErbB4) Avg EC$_{50}$ (M) | Schwann cells (SC) (ErbB3) Avg EC$_{50}$ (M) | Selectivity SC/CM | CM % Agonism AVG | SEQ ID NO: |
|---|---|---|---|---|---|
| huNRG1(S177-Q237)(3E9)::GG::huFcSEFL2 (Pb) | 2.68E–09 | >3E–6 | >8500 | Partial (70%) | 101 |
| huNRG1(S177-Q237)(3F2)::GG::huFcSEFL2 (Pb) | 7.38E–10 | >1E–5 | >10000 | Partial (70%) | 102 |
| huNRG1(S177-Q237)(3G3)::GG::huFcSEFL2 (Pb) | 1.84E–09 | >1E–5 | >5400 | Partial (70%) | 103 |
| huNRG1(S177-Q237)(3G9)::GG::huFcSEFL2 (Pb) | 5.81E–10 | >1E–5 | >10000 | Full | 104 |
| huNRG1(S177-Q237)(3H5)::GG::huFcSEFL2 (Pb) | 1.27E–09 | >1E–5 | >7800 | Full | 105 |
| huNRG1(S177-Q237)(3H8)::GG::huFcSEFL2 (Pb) | 2.76E–10 | >1E–5 | >10000 | Full | 106 |
| huNRG1(S177-Q237)(_200E)::GG::huFcSEFL2 (Pb) | 4.52E–10 | 4.82E–09 | 11 | Full | 107 |
| huNRG1(S177-Q237)()200E_KDF)::GG::huFcSEFL2 (Pb) | 2.00E–09 | 1.21E–07 | 60 | Full | 108 |
| huNRG1(S177-Q237)(_FVIEDPSI)::GG::huFcSEFL2 (Pb) | 1.77E–10 | 4.27E–09 | 24 | Full | 109 |
| huNRG1(S177-Q237)(wt)::GG::huFcSEFL2 (Pb) | 2.75E–10 | 1.12E–10 | 0.4 | Full | 25 |
| huNRG1(S177-Q237)(v80)::GG::huFcSEFL2 (Pb) | 9.98E–10 | 6.65E–09 | 7 | Full | 110 |
| huNRG1(S177-Q237)(v80.3)::GG::huFcSEFL2 (Pb) | 3.36E–08 | 3.00E–06 | 89 | Full | 111 |
| Wild-type as control | 1.54E–10 | 3.28E–10 | 2 | Full | |

The neuregulin variants tested generally showed improved selectivity toward Erbb4, with many having a selectivity greater than 1000 and even 10000 as expressed by the ratios of SM/CM. Many of the neuregulin variants also showed agonism against cardiomyocytes that was at least 80% compared to the wild-type sequence.

These results demonstrate that neuregulin variants can be designed to be selective against heart cells. This suggests that these neuregulin variants are candidates for treatment of heart diseases and may show lower side effects against neural cells.

Example 2: ErbB4 Selective Agonist Efficacy in Rat Myocardial Infarction (MI) Model An ErbB4 selective agonist (huNRG1(S177-F229) (NRGE1C)((G4E)2)::G4:: huFcSEFL2 (Pb)) was tested in a rat MI model to determine whether a benefit could be seen in improving cardiac function.

Surgically induced myocardial infarction (MI) Sprague Dawley (SD) rats (bodyweight 180-200 g) were purchased from ENVIGO (Indianapolis. Indiana, USA). 14 days before MI surgery, rats were subjected to echocardiography to assess the cardiac function by ejection fraction (EF %). Noninvasive parasternal long axis B mode cine loops were acquired using Vevo 2100 system (VisualSonics Inc., Toronto, Canada). EF was calculated using the manufacturer's recommended method. Rats were randomized into three groups based on the baseline ejection fraction numbers: 1. Vehicle; 2. ErbB4 agonist 10 µg/kg; 3. ErbB4 agonist 20 µg/kg. After randomization on week 2, 16 rats were dosed with a vehicle or 10 µg/kg or 20 µg/kg, ErbB4 agonist, subcutaneously (SC).

Anesthesia exposure is known to influence cardiac function so isoflurane was maintained at 2.5% during echocardiography to minimize its influence on cardiac function. Isoflurane exposure duration per animal was <10 min during echocardiography. Animals were closely monitored during the study. No adverse events (mortality/morbidity) were noticed throughout the study duration.

Figure 1B:
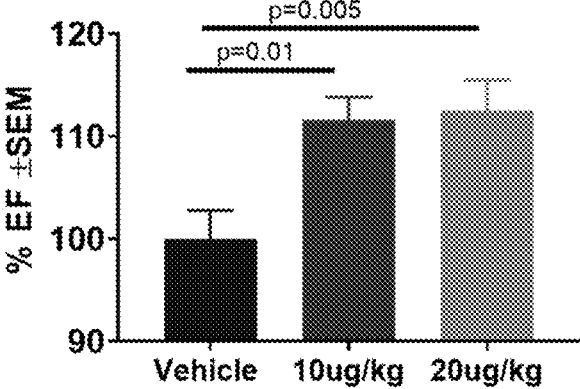
Figure 1C:
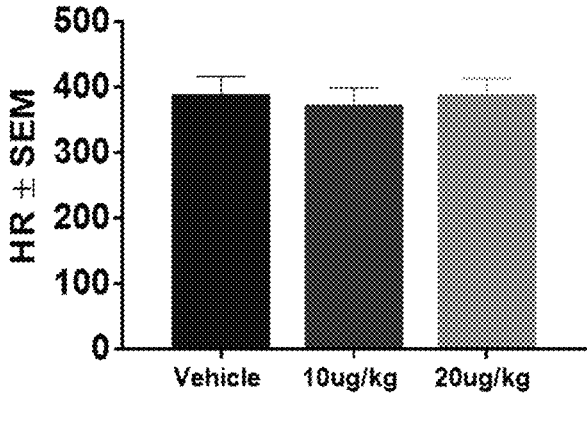

After randomization at week 2, all groups' baseline cardiac function and heart rates were similar. All the enrolled rats demonstrated heart failure condition. Terminal serum exposure was significantly higher in ErbB4 treated groups compared to the vehicle group (FIG. 1A). The plasma exposure levels of ErbB4 were markedly higher in the 20 µg/kg group than in the 10 µg/kg group (FIG. 2A). One week after subcutaneous (SC) dosing, the ErbB4 selective agonist improved cardiac function in ErbB4-selective agonist treated groups compared to the vehicle group (FIG. 1B). No statistically significant ErbB4-selective agonist effect was noticed on the heart rate (FIG. 1C), suggesting ErbB4-selective agonist mediated cardiac function improvement was not due to heart rate variability among the groups. Both treatment groups show similar cardiac functional improvements despite higher plasma exposure of the 20 µg/kg than 10 µg/kg. This suggests that higher plasma ErbB4-selective agonist exposure (>1.9 ng/mL) may be required to induce significantly higher cardiac function than observed with 10 µg/kg. No adverse events (mortality/morbidity) were not noticed after ErbB4-selective agonist treatment.

ErbB4 selective agonist treatment significantly improves cardiac function in rat myocardial infarction model. No significant impact was noticed on the heart rate after ErbB4-selective agonist treatment. ErbB4 treatment was not associated with mortality and morbidity in the myocardial infarction model

Example 3: ErbB4 Selective Agonist, without Fc, Efficacy in Rat Myocardial Infarction (MI) Model An ErbB4 selective agonist (huNRG1(S177-F229) (NRGE1C) (E47S_D48A_F49 L_M50T) 6xHis: SEQ ID NO: 61) was tested in the rat MI model to determine whether a benefit on cardiac function may be observed in response to treatment.

Sprague Dawley (Envigo, IN) rats (body weight 142-280 g) underwent surgery to induce an MI. At 7 days post-MI surgery, rats were subjected to echocardiography to assess baseline cardiac function by ejection fraction (EF %). Noninvasive parasternal long axis B mode cine loops were acquired using Vevo 3100 system (VisualSonics Inc., Toronto, Canada). EF % was calculated using the manufacturer's recommended method. Rats were randomized into groups based on the baseline EF %: [1. Vehicle]; [2. ErbB4 agonist 50 µg/kg]; [3. ErbB4 agonist 150 µg/kg]; [4. ErbB4 agonist 500 µg/kg]. After randomization at 8 days post-MI surgery, all enrolled rats demonstrated cardiac dysfunction and underwent jugular vein cannulation surgery for IV dose administration and dosing was initiated per the treatment group labels: vehicle or 50 µg/kg/day or 150 µg/kg/day or 500 µg/kg/day of ErbB4 agonist, by cannulated jugular vein, once daily for 10 days.

Serum exposure is determined on blood samples collected at 10 minutes on day 10 post treatment and data from echocardiography performed at day 11 and approx. 4 weeks post initiation of dosing is analyzed to evaluate effects on cardiac function, EF %.

What is claimed is:

1. A neuregulin variant is represented by an amino acid sequence of SEQ ID NO: 117 or 126.

2. The neuregulin variant of claim 1, further comprising a second amino acid sequence comprising a signal sequence, a half-life extension moiety, or purification tag.

3. The neuregulin variant of claim 2, wherein the second amino acid sequence comprises an Fc region or a His Tag.

4. A pharmaceutical composition comprising the neuregulin variant of any one of claims 1, 2, and 3, and a pharmaceutically acceptable carrier.

* * * * *